(12) United States Patent
Fearon et al.

(10) Patent No.: US 8,372,413 B2
(45) Date of Patent: Feb. 12, 2013

(54) IMMUNOMODULATORY POLYNUCLEOTIDES AND METHODS OF USING THE SAME

(75) Inventors: Karen L. Fearon, Lafayette, CA (US); Dino Dina, Oakland, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 402 days.

(21) Appl. No.: 11/963,663

(22) Filed: Dec. 21, 2007

(65) Prior Publication Data

US 2008/0207550 A1    Aug. 28, 2008

Related U.S. Application Data

(63) Continuation of application No. 10/033,243, filed on Dec. 27, 2001, now abandoned.

(60) Provisional application No. 60/258,675, filed on Dec. 27, 2000.

(51) Int. Cl.
*A61K 45/00* (2006.01)
*A61K 47/00* (2006.01)

(52) U.S. Cl. .................................................. 424/278.1

(58) Field of Classification Search .................. None
See application file for complete search history.

(56) References Cited

U.S. PATENT DOCUMENTS

| | | | |
|---|---|---|---|
| 4,458,066 A | 7/1984 | Caruthers et al. |
| 4,650,675 A | 3/1987 | Borel et al. |
| 4,849,513 A | 7/1989 | Smith et al. |
| 4,910,300 A | 3/1990 | Urdea et al. |
| 4,948,882 A | 8/1990 | Ruth |
| 5,015,733 A | 5/1991 | Smith et al. |
| 5,093,232 A | 3/1992 | Urdea et al. |
| 5,118,800 A | 6/1992 | Smith et al. |
| 5,118,802 A | 6/1992 | Smith et al. |
| 5,124,246 A | 6/1992 | Urdea et al. |
| 5,391,723 A | 2/1995 | Priest |
| 5,453,496 A | 9/1995 | Caruthers et al. |
| 5,460,831 A | 10/1995 | Kossovsky et al. |
| 5,484,596 A | 1/1996 | Hanna, Jr. et al. |
| 5,552,391 A | 9/1996 | Coutts et al. |
| 5,663,153 A | 9/1997 | Hutcherson et al. |
| 5,723,335 A | 3/1998 | Hutcherson et al. |
| 5,849,719 A | 12/1998 | Carson et al. |
| 5,879,906 A | 3/1999 | Jefferson et al. |
| 6,090,791 A | 7/2000 | Sato et al. |
| 6,174,872 B1 | 1/2001 | Carson et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,239,116 B1 | 5/2001 | Krieg et al. |
| 6,800,744 B1 | 10/2004 | Doucette-Stamm et al. |
| 2002/0137714 A1 | 9/2002 | Kandimalla et al. |
| 2003/0060440 A1 | 3/2003 | Klinman et al. |

FOREIGN PATENT DOCUMENTS

| | | |
|---|---|---|
| EP | 0 468 520 A2 | 1/1992 |
| EP | 0 468 520 A3 | 1/1992 |
| WO | WO-96/02555 A1 | 2/1996 |
| WO | WO-97/28259 A1 | 8/1997 |
| WO | WO-98/16247 A1 | 4/1998 |
| WO | WO-98/18810 A1 | 5/1998 |
| WO | WO-98/37919 A1 | 9/1998 |
| WO | WO-98/40100 A1 | 9/1998 |
| WO | WO-98/52581 A1 | 11/1998 |
| WO | WO-98/52581 C2 | 11/1998 |
| WO | WO-98/52962 A1 | 11/1998 |
| WO | WO-98/55495 A2 | 12/1998 |
| WO | WO-98/55495 A3 | 12/1998 |
| WO | WO-98/55495 B1 | 12/1998 |
| WO | WO-98/55609 A1 | 12/1998 |
| WO | WO-99/11275 A2 | 3/1999 |
| WO | WO-99/11275 A3 | 3/1999 |
| WO | WO-99/11275 C2 | 3/1999 |
| WO | WO-99/33488 A2 | 7/1999 |
| WO | WO-99/33488 A3 | 7/1999 |
| WO | WO-99/33868 A2 | 7/1999 |
| WO | WO-99/33868 A3 | 7/1999 |
| WO | WO-99/51259 A2 | 10/1999 |
| WO | WO-99/51259 A3 | 10/1999 |
| WO | WO-99/56755 A1 | 11/1999 |
| WO | WO-99/61056 A2 | 12/1999 |
| WO | WO-99/61056 A3 | 12/1999 |
| WO | WO-99/61056 C2 | 12/1999 |
| WO | WO-99/62923 A2 | 12/1999 |
| WO | WO-99/62923 A3 | 12/1999 |
| WO | WO-00/06588 A1 | 2/2000 |
| WO | WO-00/06588 B1 | 2/2000 |
| WO | WO-00/16804 A1 | 3/2000 |
| WO | WO-00/21556 A1 | 4/2000 |
| WO | WO-00/21556 C2 | 4/2000 |
| WO | WO-00/50006 A2 | 8/2000 |
| WO | WO-00/50006 A3 | 8/2000 |
| WO | WO-00/54803 A2 | 9/2000 |
| WO | WO-00/54803 A3 | 9/2000 |
| WO | WO-00/61151 A2 | 10/2000 |
| WO | WO-00/61151 A3 | 10/2000 |
| WO | WO-00/67023 A1 | 11/2000 |
| WO | WO-00/67787 A2 | 11/2000 |

(Continued)

OTHER PUBLICATIONS

Yamamoto et al (Antisense Research and Development 4:119-122, 1994.*

(Continued)

*Primary Examiner* — Patricia A Duffy

(74) *Attorney, Agent, or Firm* — Morrison & Foerster LLP

(57) ABSTRACT

The invention provides immunomodulatory polynucleotides and methods for immunomodulation of individuals using the immunomodulatory polynucleotides.

22 Claims, No Drawings

FOREIGN PATENT DOCUMENTS

| | | |
|---|---|---|
| WO | WO-00/67787 A3 | 11/2000 |
| WO | WO-01/12223 A2 | 2/2001 |
| WO | WO-01/12223 A3 | 2/2001 |
| WO | WO-01/15726 A2 | 3/2001 |
| WO | WO-01/15726 A3 | 3/2001 |
| WO | WO-01/22972 A2 | 4/2001 |
| WO | WO-01/22972 A3 | 4/2001 |
| WO | WO-01/22972 C2 | 4/2001 |
| WO | WO-01/22990 A2 | 4/2001 |
| WO | Wo-01/22990 A3 | 4/2001 |
| WO | WO-01/35991 A2 | 5/2001 |
| WO | WO-01/35991 A3 | 5/2001 |
| WO | WO-01/51500 A1 | 7/2001 |
| WO | WO-01/54720 A1 | 8/2001 |
| WO | WO-01/68103 A2 | 9/2001 |
| WO | WO-01/68103 A3 | 9/2001 |
| WO | WO-01/68103 C2 | 9/2001 |
| WO | WO-03/000922 A2 | 1/2003 |
| WO | WO-03/000922 A3 | 1/2003 |
| WO | WO-03/014316 A2 | 2/2003 |
| WO | WO-03/014316 A3 | 2/2003 |
| WO | WO-03/015711 A2 | 2/2003 |
| WO | WO-03/015711 A3 | 2/2003 |
| WO | WO-03/015711 C2 | 2/2003 |
| WO | WO-03/015816 A1 | 2/2003 |
| WO | WO-03/020884 A2 | 3/2003 |
| WO | WO-03/020884 A3 | 3/2003 |

OTHER PUBLICATIONS

Zhao et al (Biochemical Pharmacology, 51:173-182, 1996.*
Agarwal et al, Molecular Med, Today, 6:72-81, 2000.*
Weiner (J. Leukocyte Biology, 68:456-463, 2000.*
Kline et al J. Immunol, 160:2555-2559, 1998.*
Kline et al (Am J. Physiol. Lung Cell Mol. Physiol., 283:L170-L179, 2002.*
Wohlleben et al, TRENDS in Immunology 22(11):618-626, 2001.*
Krieg et al, Immunology Today 21(10):521-526, 2000,.*
McCluskie et al , Molecular Med, 5(5):287-300, 1999.*
The Merck Manual, Centennial Edition, 1999, pp. 556-567 and 1042-1058.*
Herbert et al, The Dictionary of Immunology, Academic Press, 1995, p. 93.*
Herbert et al, The Dictionary of Immunology, Academic Press, 1995, p. 88.*
Agrawal, S. et al. et al. (1986). "Efficient Methods for Attaching Non-Radioactive Labels to the 5' ends of Synthetic Oligodeoxyribonucleotides," *Nucleic Acids Res.* 14(15):6227-6245.
Agrawal, S. et al. (Feb. 2000). "Antisense Therapeutics: is It as Simple as Complementary Base Recognition?" *Molecular Med. Today* 6(2):72-81.
Ahmeida, E.T.S. Ben et al. (1993). "Immunopotentiation of Local and Systemic Humoral Immune Responses by ISCOMs, Liposomes and FCA: Role in Protection Against Influenza A in Mice," *Vaccine* 11(13):1302-1309.
Aramaki, Y. et al. (1995). "Interferon-γ Inductive Effect of Liposomes as an Immunoadjuvant," *Vaccine* 13(18):1809-1814.
Asanuma, H. et al. (1995). "Cross-Protection Against Influenza Virus Infection in Mice Vaccinated by Combined Nasal-Subcutaneous Administration," *Vaccine* 13(1):3-5.
Atherton, E. et al. (Jul. 1981). "Synthesis of a 21-Residue Fragment of Human Proinsulin by the Polyamide Solid Phase Method," *Hoppe-Seylers Z. Physiol. Chem.* 362:833-839.
Ausubel, F.M. et al., eds. (1995). *Current Protocols in Molecular Biology*, vol. 1, John Wiley & Sons, Inc.: pp. iii-xii (Table of Contents).
Ballas, Z. K. et al. (1996). "Induction of NK Activity in Murine and Human Cells by CpG Motifs in Oligodeoxynucleotides and Bacterial DNA," *J. Immunol.*, 157:1840-1845.
Beaucage, S. L. (1993). "Oligodeoxyribonucleotide Synthesis," Chapter 3 In *Protocols for Oligonucleotides and Analogs, Synthesis and Properties*, Sudhir Agrawal, ed., Humana Press, Totowa, NJ., 20:33-61.

Benoit, R. et al. (1987). "Peptides. Strategies for Antibody Production and Radioimmunoassays," In *Neuromethods*, Alan A. Boulton et al., eds., Humana Press, Clifton, NJ 6:43-72.
Bischoff, R. et al. (1987). "Introduction of 5'-Terminal Functional Groups into Synthetic Oligonucleotides for Selective Immobilization," *Anal. Bioch.* 164:336-344.
Blanks, R. et al. (1988). "An Oligodeoxynucleotide Affinity Column for the Isolation of Sequence Specific DNA Binding Proteins," *Nucleic Acids Res.* 16(21):10283-10299.
Bohle, B. et al. (1999). "Oligodeoxynucleotides Containing CpG Motifs Induce IL-12, IL-18, and IFN-γ Production in Cells from Allergic Individuals and Inhibit IgE Synthesis in Vitro," *Eur. J. Immunol.* 29:2344-2353.
Borel, H. et al. (1990). "A Novel Technique to Link Either Proteins or Peptides to Gammaglobulin to Construct Tolerogens," *Immunol. Methods* 126:159-168.
Borel, Y. et al. (1995). "Food Allergens Transformed Into Tolerogens," *Int. Arch. Allergy Immunol.* 107:264-267.
Borel, Y. et al. (1996). "Parenteral and Oral Administation of Tolerogens: Protein-IgG Conjugates," vol. 778 in *Oral Tolerance: Mechanisms and Applications* Ann. N.Y. Acad. Sci. pp. 80-87.
Boujrad, N. et al. (Jun. 1993). "Inhibition of Hormone-Stimulated Steroidogenesis in Cultured Leydig Tumor Cells by a Cholesterol-Linked Phosphorothioate Oligodeoxynucleotide Antisense to Diazepam-Binding Inhibitor," *P NAS USA* 90:5728-5731.
Bousquet, Y. et al. (1999). "Molecular Mechanisms of the Adsorption of a Model Protein (Human Serum Albumin) on Poly(Methylidene Malonate 2.1.2) Nanoparticles," *Pharm. Res.* 16(1):141-147.
Branda, R. F. et al. (1993). "Immune Stimulation by an Antisense Oligomer Complementary to the rev Gene of HIV-1," *Biochem. Pharmacol.* 45(10):2037-2043.
Branda, R. F. et al. (1996). "Amplification of Antibody Production by Phosphorothioate Oligodeoxynucleotides," *J. Lab. Clin. Med.* 128(3):329-338.
Braun, R. P. and Lee, J. S. (1988). "Immunogenic Duplex Nucleic Acids are Nuclease Resistant," *J. Immunol.* 141(6):2084-2089.
Brazolot-Milan, C. L. et al. (1998). "CpG DNA Can Induce Strong Th1 Humoral and Cell-Mediated Immune Responses Against Hepatitis B Surface Antigen in Young Mice," *P NAS USA* 95:15553-15558.
Breiteneder, H. et al. (1989). "The Gene Coding for the Major Birch Pollen Allergen *Betvl*, is Highly Homologous to a Pea Disease Resistance Response Gene," *EMBO J.* 8(7):1935-1938.
Broide, D. et al. (1998). "Immunostimulatory DNA Sequences Inhibit IL-5, Eosinophilic Inflammation, and Airway Hyper-responsiveness in Mice," *J. Immunol.* 161:7054-7062.
Broide, D. et al. (1999). "DNA-Based Immunization for Asthma," *Int. Arch. Allergy Immunol.* 118:453-456.
Carson, D. A. et al. (1997). "Oligonucleotide Adjuvants for T Helper 1 (Th1)-Specific Vaccination," *J. Exp. Med.* 186(10):1621-1622.
Chace, J. H. et al. (1997). "Bacterial DNA-Induced NK Cell IFN-γ Production is Dependent on Macrophage Secretion of IL-12," *Clin. Immunol. and Immunopathol.* 84(2):185-193.
Chaturvedi, S. et al. (1996). "Stabilization of Triple-Stranded Oligonucleotide Complexes: Use of Probes Containing Alternating Phosphodiester and Stereo-Uniform Cationic Phosphoramidate Linkages," *Nucleic Acids Res.* 24(12):2318-2323.
Chavany, C. et al. (1992). "Polyalkylcyanoacrylate Nanoparticles as Polymeric Carriers for Antisense Oligonucleotides," *Pharm. Res.* 9(4):441-449.
Chavany, C. et al. (1994). "Adsorption of Oligonucleotides onto Polyisohexylcyanoacrylate Nanoparticles Protects Them Against Nucleases and Increases Their Cellular Uptake," *Pharm. Res.* 11(9):1370-1378.
Chen, Z. et al. (1999). "Enhanced Protection Against a Lethal Influenza Virus Challenge by Immunization with Both Hemagglutinin- and Neuraminidase-Expressing DNAs," *Vaccine* 17:653-659.
Cho, H. J. et al. (May 2000). "Immunostimulatory DNA-Based Vaccines Induce Cytotoxic Lymphocyte Activity by a T-Helper Cell-Independent Mechanism," *Nature Biotechnol.* 18:509-514.
Chu, R. S. et al. (Nov. 1997). "CpG Oligodeoxynucleotides Act as Adjuvants that Switch on T Helper 1 (Th1) Immunity," *J. Exp. Med.* 186(10):1623-1631.

Chua, K.Y. et al. (Jan. 1, 1988). "Sequence Analysis of cDNA Coding for a Major House Dust Mite Allergen, Der p 1. Homology with Cysteine Proteases," *J. Exp. Med.* 167(1):175-182.

Chua, K.Y. et al. (1990). "Expression of *Dermatophagoides pteronyssinus* Allergen, Der p II, in *Escherichia coli* and the Binding Studies with Human IgE," *Int. Arch. Allergy Appl. Immunol.* 91:124-129.

Coligan, J. E. et al., eds. (1998). *Current Protocols in Immunology*, vol. 1, John Wiley &.Sons, Inc: pp. 1-9.

Connolly, B. A. (1985). "Chemical Synthesis of Oligonucleotides Containing a Free Sulphydryl Group and Subsequent Attachment of Thiol Specific Probes," *Nucleic Acids Res.* 13(12):4485-4502.

Connolly, B. A. (1987). "The Synthesis of Oligonucleotides Containing a Primary Amino Group at the 5'-Terminus," *Nucleic Acids Res.* 15(7):3131-3139.

Cooke, S.K. et al. (1997). "Allergenic Properties of Ovomucoid in Man," *J. Immunol.* 159:2026-2032.

Corey, D. R. et al. (Dec. 1987). "Generation of a Hybrid Sequence-Specific Single-Stranded Deoxyribonuclease," *Science* 238:1401-1403.

Cowdery, J. S. et al. (1996). "Bacterial DNA Induces NK Cells to Produce IFN-γ in Vivo and Increases the Toxicity of Lipopolysaccharides," *J. Immunol.* 156:4570-4575.

De Martino, M. et al. (Aug. 1999). "Low IgG3 and High IgG4 Subclass Levels in Children with Advanced Human Immunodeficiency Virus-Type 1 Infection and Elevated IgE Levels," *Annals of Allergy, Asthma & Immunol.* 83:160-164.

Douglas, S. J. et al. (1987). "Nanoparticles in Drug Delivery," *Crit. Rev. Ther. Drug. Carrier Syst.* 3(3):233-261.

Dumas, V. et al. (1995). "Induction of Tolerance by Administration of Hapten-Immunoglobulin Conjugates is Associated with Decreased IL-2 and IL-4 Production," *Arch. Dermatol. Res.* 287:123-128.

Elkins, K. L. et al. (1999). "Bacterial DNA Containing CpG Motifs Stimulates Lymphocyte-Dependent Protection of Mice Against Lethal Infection with Intracellular Bacteria," *J. Immunol.* 162:2291-2298.

Elsayed, S. et al. (1991). "The Structural Requirements of Epitopes with IgE Binding Capacity Demonstrated by Three Major Allergens from Fish, Egg and Tree Pollen," *Scand. J. Clin. Lab. Invest.* 51:Suppl. 204:17-31.

Fornadley, J. (1998). "Allergy Immunotherapy," *Otolaryngol. Clin. North Am.* 31(1):111-127.

Freshney, R.I., ed. (1987). *Animal Cell Culture: A Practical Approach*, IRL Press: pp. vii-xii (Table of Contents).

Gait, M.J., ed. (1984). *Oligonucleotide Synthesis: A Practical Approach*, IRL Press: pp. vii-xii (Table of Contens).

Galland, A.V. et al. (1998). "Purification of a 41 kDa Cod-Allergenic Protein," *J. Chromatogr. B.* 706:63-71.

Gao, H. et al. (1995). "Circularization of Oligonucleotides by Disulfide Bridge Formation," *Nucleic Acids Res.* 23(11):2025-2029.

Geoghegan, K. F. et al. (1992). "Site-Directed Conjugation of Nonpeptide Groups to Peptides and Proteins Via Periodate Oxidation of a 2-Amino Alcohol. Application to Modification at N-Terminal Serine," *Bioconjug. Chem.* 3(2):138-146.

Godard, G. et al. (1995). "Antisense Effects of Cholesterol-Oligodeoxynucleotide Conjugates Associated with Poly(Alkylcyanoacrylate) Nanoparticles," *Eur. J. Biochem.* 232:404-410.

Goodchild, J. (May/Jun. 1990). "Conjugates of Oligonucleotides and Modified Oligonucleotides: A Review of Their Synthesis and Properties," *Bioconjug. Chem.* 1(3):165-187.

Govorkova, E. A. et al. (1997). "Cross-Protection of Mice Immunized with Different Influenza A (H2) Strains and Challenged with Viruses of the Same HA Subtype," *Acta Virol.* 41:251-257.

Grabarek, Z. et al. (1990). "Zero-Length Crosslinking Procedure with the Use of Active Esters," *Anal. Biochem.* 185:131-135.

Gramzinski, R. A. et al. (Feb. 1998). "Immune Response to a Hepatitis B DNA Vaccine in *Aotus* Monkeys: A Comparison of Vaccine Formulation, Route, and Method of Administration," *Mol. Med.* 4:109-118.

Granoff, D. M. et al. (1993). "Effect of Immunity to the Carrier Protein on Antibody Responses to *Haemophilus Influenzae* Type B Conjugate Vaccines," *Vaccine* 11: Suppl.1:46-51.

Hagiwara, A. et al. (1987). "A New Drug-Delivery-System of Anticancer Agents: Activated Carbon Particles Adsorbing Anticancer Agents," In Vivo 1:241-252.

Hames, B.D. et al., eds. (1987). *Transcription and Translation: A Practical Approach*, IRL Press: pp. vii-xiv (Table of Contents).

Haralambidis, J. et al. (1990a). "The Synthesis of Polyamide-Oligonucleotide Conjugate Molecules," *Nucleic Acids Res.* 18(3):493-499.

Haralambidis, J. at al. (1990b). "The Preparation of Polyamide-Oligonucleotide Probes Containing Multiple Non-Radioactive Labels," *Nucleic Acids Res.* 18(3):501-505.

Herbert et al. (1995). *The Dictionary of Immunology*, Academic Press pp. 88 and 93.

Hermanson, G.T. (1996). *Bioconjugate Techniques*, Academic Press, Inc.: pp. ix-xx (Table of Contents).

Horner, A. A. et al. (1998). "Immunostimulatory DNA is a Potent Mucosal Adjuvant," *Cell. Immunol.* 190:77-82.

Jäger, A. et al. (1988). "Oligonucleotide N-Alkylphosphoramidates: Synthesis and Binding to Polynucleotides," *Biochem.* 27(19):7237-7246.

Jakob, T. et al. (1998). "Activation of Cutaneous Dendritic Cells by CpG-Containing Oligodeoxynucleotides: A Role for Dendritic Cells in the Augmentation of Th1 Responses by Immunostimulatory DNA," *J. Immunol.* 161:3042-3049.

Kataoka, T. et al. (1992). "Antitumor Activity of Synthetic Oligonucleotides with Sequences from cDNA Encoding Proteins of *Mycobacterium bovis* BCG," *Jpn. J. Cancer Res.* 83:244-247.

Kendrew, J., ed. (1994). *The Encyclopedia of Molecular Biology* (Table of Contents).

Kessler, C. (Dec. 1992). "Nonradioactive Labeling Methods for Nucleic Acids," Chapter 2 In *Nonisotopic DNA Probe Techniques*, Larry J. Kricka, ed., Academic Press, Inc.: pp. 29-92.

Kikuta, K. et al. (1990). "Cross-Protection Against Influenza B Type Virus Infection by Intranasal Inoculation of the HA Vaccines Combined with Cholera Toxin B Subunit," *Vaccine* 8:595-599.

Kimura, Y. et al. (1994). "Binding of Oligoguanylate to Scavenger Receptors is Required for Oligonucleotides to Augment NK Cell Activity and Induce IFN," *J. Biochem.* 116(5):991-994.

Kingetsu, I. et al. (2000). "Common Antigenicity between Japanese Cedar (*Cryptomeria japonica*) Pollen and Japanese Cypress (*Chamaecyparis obtusa*) Pollen, I. H-2 Complex Affects Cross Responsiveness to Cry j 1 and Cha o 1 at the T- and B-cell Level in Mice," *Immunol.* 99:625-629.

Kline, J. N. et al. (Mar. 1997). "Immune Redirection by CpG Oligonucleotides Conversion of a Th2 Response to a Th1 Response in a Murine Model of Asthma," *J. Invest. Med.* 45(3):282A.

Kline, J.N. et al. (Mar. 15, 1998). "Modulation of Airway Inflammation by CpG Oligodeoxynucleotides in a Murine Model of Asthma.," *J. Immunol.* 160(6):2555-2559.

Kline, J.N. et al. (Jul. 2002). "Treatment of Established Asthma in a Murine Model Using CpG Oligodeoxynucleotides," *Am. J. Physiol. Lung Cell Mol. Physiol.* 283(1):L170-L179.

Klinman, D. M. et al. (Apr. 1996). "CpG Motifs Present in Bacterial DNA Rapidly Induce Lymphocytes to Secrete Interleukin 6, Interleukin 12, and Interferon γ," *PNAS USA* 93:2879-2883.

Klinman, D. M. et al. (1997). "Contribution of CpG Motifs to the Immunogenicity of DNA Vaccines," *J. Immunol.* 158:3635-3639.

Kodihalli, S. et al. (May 1997). "Cross-Protection Among Lethal H5N2 Influenza Viruses Induced by DNA Vaccine to the Hemagglutinin," *J. Virol.* 71(5):3391-3396.

Kovarik, J. et al. (1999). "CpG Oligodeoxynucleotides Can Circumvent the Th2 Polarization of Neonatal Responses to Vaccines But May Fail to Fully Redirect Th2 Responses Established by Neonatal Priming," *J. Immunol.* 162:1611-1617.

Kremsky, J. N. et al. (1987). "Immobilization of DNA via Oligonucleotides Containing an Aldehyde or Carboxylic Acid Group at the 5' Terminus," *Nucleic Acids Res.* 15(7):2891-2909.

Krieg, A. M. (Feb. 1996). "Lymphocyte Activation by CpG Dinucleotide Motifs in Prokaryotic DNA," *Trends Microbiol.* 4(2):73-77.

Krieg, A. M. (1998). "Leukocyte Stimulation by Oligodeoxynucleotides," Chapter 24 in *Applied Antisense Oligonucleotide Technology*, C.A. Stein and Arthur M. Krieg, eds., Wiley-Liss, Inc.: pp. 431-448.

Krieg, A. M. (Feb. 1999). "CpG DNA: A Novel Immunomodulator," *Trends Microbiol.* 7(2):64-65.

Krieg, A. M. et al. (Oct. 1989). "A Role for Endogenous Retroviral Sequences in the Regulation of Lymphocyte Activation," *J. Immunol.* 143(6):2448-2451.

Krieg, A. M. et al. (Apr. 1995). "CpG Motifs in Bacterial DNA Trigger Direct B-Cell Activation," *Nature* 374:546-549.

Krieg, A. M. et al. (1996). "Oligodeoxynucleotide Modifications Determine the Magnitude of B Cell Stimulation by CpG Motifs," *Antisense Nucleic Acid Drug Dev.* 6:133-139.

Krieg, A. M. et al. (Jan. 1998a). "The Role of CpG Dinucleotides in DNA Vaccines," *Trends Microbiol.* 6(1):23-27.

Krieg, A. M. et al. (1998b). "CpG DNA Induces Sustained IL-12 Expression in Vivo and Resistance to *Listeria monocytogenes* Challenge," *J. Immunol.* 161:2428-2434.

Krieg, A. M. et al. (Oct. 1998c). "Sequence Motifs in Adenoviral DNA Block Immune Activation by Stimulatory CpG Motifs," *PNAS USA* 95:12631-12636.

Krieg, A.M. et al. (Oct. 2000). "Causing a Commotion in the Blood: Immunotherapy Progresses from Bacteria to Bacterial DNA.," *Immunology Today* 21(10):521-526.

Kullman, W. (1997). *Enzymatic Peptide Synthesis*, CRC Press, Inc. Boca Raton, FL: (Table of Contents).

Lambert, G. et al. (1998). "Effect of Polyisobutylcyanoacrylate Nanoparticles and Lipofectin® Loaded with Oligonucleotides on Cell Viability and PKCα Neosynthesis in HepG2 Cells," *Biochimie* 80:969-976.

Langenberg, A. G. M. (Jun. 1995). "A Recombinant Glycoprotein Vaccine for Herpes Simplex Type 2: Safety and Efficacy," *Ann. Intern. Med.* 122(12):889-898.

Lasic, D.D. (1993). *Liposomes: From Physics to Applications*, Elsevier, Amsterdam: pp. xi-xviii (Table of Contents).

Latimer, L. J. P. et al. (1995). "Specificity of Monoclonal Antibodies Produced Against Phosphorothioate and Ribo Modified DNAs," *Mol. Immunol.* 32(14/15):1057-1064.

Lea, I. A. et al., (1996). "Cloning and Sequencing of cDNAs Encoding the Human Sperm Protein, Sp17," *Biochim. et Biophys. Acta* 1307:263-266.

Leclerc, C. et al. (1997). "The Preferential Induction of a Th1 Immune Response by DNA-Based Immunization is Mediated by the Immunostimulatory Effect of Plasmid DNA," *Cell. Immunol.* 179:97-106.

Liang, H. et al. (1996). "Activation of Human B Cells by Phosphorothioate Oligodeoxynucleotides," *J. Clin. Invest.* 98(5):1119-1129.

Lipford, G. B. et al. (1997a). "CpG-Containing Synthetic Oligonucleotides Promote B and Cytotoxic T Cell Responses to Protein Antigen: A New Class of Vaccine Adjuvants," *Eur. J. Immunol.* 27:2340-2344.

Lipford, G. B. et al. (1997b). "Immunostimulatory DNA: Sequence-Dependent Production of Potentially Harmful or Useful Cytokines," *Eur. J. Immunol.* 27:3420-3426.

Liu, H-M. et al. (1998). "Immunostimulatory CpG Oligodeoxynucleotides Enhance the Immune Response to Vaccine Strategies Involving Granulocyte-Macrophage Colony-Stimulating Factor," *Blood* 92(10):3730-3736.

MacFarlane, D. E. et al. (1997). "Unmethylated CpG-Containing Oligodeoxynucleotides Inhibit Apoptosis in WEHI 231 B Lymphocytes Induced by Several Agents: Evidence for Blockade of Apoptosis at a Distal Signalling Step," *Immunology* 91:586-593.

Manzel, L. et al. (1999). "Lack of Immune Stimulation by Immobilized CpG-Oligodeoxynucleotide," *Antisense Nucl. Acid Drug Dev.* 9:459-464.

Martin-Orozco, E. et al. (1999). "Enhancement of Antigen-Presenting Cell Surface Molecules Involved in Cognate Interactions by Immunostimulatory DNA Sequences," *Int. Immunol.* 11 (7):1111-1118.

Masseyeff, R.F., ed. (1993). *Methods of Immunological Analysis. vol. 1: Fundamentals*, Verlagsgesellschaft mbH, D-6940, Weinheim, Germany: pp. xi-xxii (Table of Contents).

Matteucci, M. (1997). "Oligonucleotide Analogs: An Overview," In *Oligonucleotides as Therapeutic Agents*. D.J. Chadwick and G. Cardew, eds., John Wiley and Sons, New York, NY., pp. 5-18.

Mbawuike, I. N. et al. (1994). "Influenza: A Subtype Cross-Protection After Immunization of Outbred Mice with a Purified Chimeric $NS_1/HA_2$ Influenza Virus Protein," *Vaccine* 12(14):1340-1348.

McCluskie, M. J. et al. (1998). "CpG DNA is a Potent Enhancer of Systemic and Mucosal Immune Responses Against Hepatitis B Surface Antigen with Intranasal Administration to Mice," *J. Immunol.* 161:4463-4466.

McCluskie, M.J. et al. (May 1999). "Route and Method of Delivery of DNA Vaccine Influence Immune Responses in Mice and Non-Human Primates," *Molecular Med.* 5(5):287-300.

Miller, J.H. et al., eds. (1987). "Gene Transfer Vectors for Mammalian Cells," in *Current Communications in Molecular Biology*, Cold Spring Harbor Laboratory: pp. vii-ix (Table of Contents).

Miller, P. S. et al. (1971). "Syntheses and Properties of Adenine and Thymine Nucleoside Alkyl Phosphotriesters, the Neutral Analogs of Dinucleoside Monophosphates," *JACS* 93(24):6657-6665.

Mishell, B.B. et al., eds. *Selected Methods in Cellular Immunology*, W.H. Freeman & Co., San Francisco: pp. vii-xiv (Table of Contents).

Mitragotri, S. et al. (Aug. 1995). "Ultrasound-Mediated Transdermal Protein Delivery," *Science* 269:850-853.

Mojcik, C. F. et al. (May 1993). "Administration of a Phosphorothioate Oligonucleotide Antisense to Murine Endogenous Retroviral MCF *Env* Causes Immune Effects in Vivo in a Sequence-Specific Manner," *Clin. Immunol. and Immunopathol.* 67(2):130-136.

Moldoveanu, Z. et al. (1998). "CpG DNA, A Novel Immune Enhancer for Systemic and Mucosal Immunization with Influenza Virus," *Vaccine* 16(11/12):1216-1224.

Mullis, K.B. et al., eds. (1994). *PCR: The Polymerase Chain Reaction*, Birkhäuser: pp. xv-xvii (Table of Contents).

Nelson, J. S. et al. (1997). "N3'→P5' Oligodeoxyribonucleotide Phosphoramidates: A New Method of Synthesis Based on a Phosphoramidite Amine-Exchange Reaction," *J. Org. Chem.* 62(21):7278-7287.

Nelson, P. S. et al. (1989). "Bifunctional Oligonucleotide Probes Synthesized Using a Novel CPG Support are able to Detect Single Base Pair Mutations," *Nucleic Acids Res.* 17(18):7187-7194.

O'Shannessy, D. J. et al. (1985). "Specific Conjugation Reactions of the Oligosaccharide Moieties of Immunoglobulins," *J. Applied Biochem.* 7:347-355.

Pastorello, E.A. et al. (1998). "Sensitization to the Major Allergen of Brazil Nut is Correlated with the Clinical Expression of Allergy," *J. Allergy Clin. Immunol.* 102(6):1021-1027.

Pertmer, T. M. et al. (Sep. 1996). "Influenza Virus Nucleoprotein-Specific Immunoglobulin G Subclass and Cytokine Responses Elicited by DNA Vaccination are Dependent on the Route of Vector DNA Delivery," *J. Virol.* 70(9):6119-6125.

Peyrottes, S. et al. (1996). "Oligodeoxynucleoside Phosphoramidates (P-$NH_2$): Synthesis and Thermal Stability of Duplexes with DNA and RNA Targets," *Nucleic Acids Res.* 24(10):1841-1848.

Pisetsky, D. S. et al. (1994). "Stimulation of Murine Lymphocyte Proliferation by a Phosphorothioate Oligonucleotide with Antisense Activity for Herpes Simplex Virus," *Life Sci.* 54(2):101-107.

Pisetsky, D. S. et al. (1995). "Immunological Properties of Bacterial DNA," *Ann. N.Y. Acad. Sci.* 772:152-163.

Pisetsky, D. S. (Jan. 1996a). "The Immunologic Properties of DNA," *J. Immunol.* 156(2):421-423.

Pisetsky, D. S. (Oct. 1996b). "Immune Activation by Bacterial DNA: A New Genetic Code," *Immunity* 5:303-310.

Rafnar, T. et al. (1991). "Cloning of *Amb a I* (Antigen E), the Major Allergen Family of Short Ragweed Pollen," *J. Biol. Chem.* 266:1229-1236.

Raz, E. et al. (Sep. 1994). "Intradermal Gene Immunization: The Possible Role of DNA Uptake in the Induction of Cellular Immunity to Viruses," *PNAS USA* 91:9519-9523.

Raz, E. et al. (May 1996). "Preferential Induction of a Th$_1$ Immune Response and Inhibition of Specific IgE Antibody Formation by Plasmid DNA Immunization," *PNAS USA* 93:5141-5145.

Redford, T. W. et al. (1998). "Cyclosporin A Enhances IL-12 Production by CpG Motifs in Bacterial DNA and Synthetic Oligodeoxynucleotides," *J. Immunol.* 161:3930-3935.

Reese, G. et al. (1997). "Characterization of Recombinant Shrimp Allergen Pen a 1 (Tropomyosin)," *Int. Arch. Allergy Immunol.* 113:240-242.

Reynolds, M. A. et al. (1996). "Antisense Oligonucleotides Containing an Internal, Non-Nucleotied-Based Linker Promote Site-Specific Cleavage of RNA," *Nucleic Acids Res.* 24(4):760-765.

Rhodes, A. J. et al., eds. (1953). "Fundamental Characteristics and Technical Methods and Apparatus" in *Textbook of Virology for Students and Practioners of Medicine*. 2nd ed., Williams and Wilkins Company, Baltimore, MD. pp. 66-69.

Rogers, B.L. et al. (1993). "Recombinant *Fel d* I: Expression, Purification, IgE Binding and Reaction with Cat-Allergic Human T Cells," *Mol. Immunol.* 30(6):559-568.

Roget, A. et al. (1989). "Synthesis and Use of Labelled Nucleoside Phosphoramidite Building Blocks Bearing a Reporter Group: Biotinyl, Dinitrophenyl, Pyrenyl and Dansyl," *Nucleic Acids Res.* 17(19):7643-7651.

Romagnani, S. (Jul. 2000). "T-Cell Subsets (Th1 versus Th2)," *Ann. Allergy, Asthma, and Immunol.* 85(1):9-18.

Roman, M. et al. (Aug. 1997). "Immunostimulatory DNA Sequences Function as T Helper-1-Promoting Adjuvants," *Nature Med.* 3(8):849-854.

Ruth, J. L. (1991). "Oligodeoxynucleotides with Reporter Groups Attached to the Base," Chapter 11 in *Oligonucleotides and Analogues: A Practical Approach*, F. Eckstein, ed., IRL Press: pp. 255-282.

Sambrook, J. et al., eds. (1989). Molecular Cloning: A Laboratory Manual, Second Edition, Cold Spring Harbor Laboratory Press: pp. x-xxxviii (Table of Contents).

Sato, Y. et al. (Jul. 1996). "Immunostimulatory DNA Sequences Necessary for Effective Intradermal Gene Immunization," *Science* 273:352-354.

Schacht, E. et al. (Oct. 1996). "Biomedical Applications of Degradable Polyphosphazenes," *Biotechnol. Bioeng.* 52:102-108.

Scherle, P. A. et al. (Oct. 1986). "Functional Analysis of Influenza Specific- Helper T Cell Clones in Vivo," *J. Exp. Med.* 164:1114-1128.

Scherle, P. A. et al. (Jun. 1988). "Differential Ability of B Cells Specific for External vs. Internal Influenza Virus Proteins to Respond to Help from Influenza Virus-Specific T-cell Clones in Vivo," *PNAS USA* 85:4446-4450.

Schultz, R. G. et al. (Jul. 1996). "Oligo-2'-Fluoro-2'-Deoxynucleotide N3'-P5' Phosphoramidates: Synthesis and Properties," *Nucleic Acids Res.* 24(15):2966-2973.

Schwartz, D. A. et al. (1997). "CpG Motifs in Bacterial DNA Cause Inflammation in the Lower Respiratory Tract," *J. Clin. Invest.* 100(1):68-73.

Sélo, I. et al. (1999). "Allergy to Bovine β-Lactoglobulin: Specificity of Human IgE to Tryptic Peptides," *Clin. Exp. Allergy* 29:1055-1063.

Shimada, S. et al. (Aug. 1986). "In Vivo Augmentation of Natural Killer Cell Activity with a Deoxyribonucleic Acid Fraction of BCG," *Jpn. J. Cancer Res.* 77:808-816.

Sinha, N. D. et al. (1991). "Oligonucleotides with Reporter Groups Attached to the 5'-Terminus," Chapter 8 in *Oligonucleotide Analogues: A Practical Approach*, F. Eckstein, ed., IRL Press: pp. 185-210.

Sonehara, K. et al. (1996). "Hexamer Palindromic Oligonucleotides with 5'-Cg-3' Motif(s) Induce Production of Interferon," *J. Interferon and Cytokine Res.* 16:799-803.

Sowka, S. et al. (1998). "cDNA Cloning of the 43-kDa Latex Allergen Hev b 7 with Sequence Similarity to Patatins and its Expression in the Yeast *Pichia pastoris*," *Eur. J. Biochem.* 255:213-219.

Sparwasser, T. et al. (1997). "Macrophages Sense Pathogens Via DNA Motifs: Induction of Tumor Necrosis Factor-α-Mediated Shock," *Eur. J. Immunol.* 27:1671-1679.

Spiegelberg, H.L. et al. (1998). "Inhibition of IgE Formation and Allergic Inflammation by Allergen Gene Immunization and by CpG Motif Immunostimulatory Oligodeoxynucleotides," *Allergy* 53:93-97.

Spiegelberg, H. L. et al. (1999). "Inhibition of Allergic Inflammation in the Lung by Plasmid DNA Allergen Immunization," *Pediatr. Pulmonol. Suppl.* 18:118-121.

Stacey, K. J. et al. (1996). "Macrophages Ingest and are Activated by Bacterial DNA," *J. Immunol.* 157:2116-2122.

Stanley, J.S. et al. (1996). "Peanut Hypersensitivity: IgE Binding Characteristics of a Recombinant *Ara h* 1 Protein," *Adv. Exp. Med. Biol.* 409:213-216.

Staros, J. V. et al. (1986). "Enhancement by *N*-Hydroxysulfosuccinimide of Water-Soluble Carbodiimide-Mediated Coupling Reactions," *Anal. Biochem.* 156:220-222.

Stein, C. A. et al. (1997). "Non-Antisense Effects of Oligodeoxynucleotides," Chapter 11 in *Antisense Technology*, C. Lichtenstein and W. Nellen, eds., IRL Press: pp. 241-264.

Stirchak, E. P. et al. (1989). "Uncharged Stereoregular Nucleic Acid Analogs: 2. Morpholino Nucleoside Oligomers with Carbamate Internucleoside Linkages," *Nucleic Acids Res.* 17(15):6129-6141.

Takahashi, H. et al. (Apr. 1990). "Induction of CD8$^+$ Cytotoxic T Cells by Immunization with Purified HIV-1 Envelope Protein in ISCOMs," *Nature* 344:873-875.

Tamborini, E. et al. (1997). "Biochemical and Immunological Characterization of Recombinant Allergen Lol p 1," *Eur. J. Biochem.* 249:886-894.

Tamura, S-I. et al. (1992). "Superior Cross-Protective Effect of Nasal Vaccination to Subcutaneous Inoculation with Influenza Hemagglutinin Vaccine," *Eur. J. Immunol.* 22:477-481.

Tamura, S-I. et al. (1994). "Formulation of Inactivated Influenza Vaccines for Providing Effective Cross-Protection by Intranasal Vaccination in Mice," *Vaccine* 12(4):310-316.

Teuber, S.S. et al. (1998). "Cloning and Sequencing of a Gene Encoding a 2S Albumin Seed Storage Protein Precursor from English Walnut (*Juglans regia*), a Major Food Allergen," *J. Allergy Clin. Immun.* 101:807-814.

Tokunaga, T. et al. (1992). "Synthetic Oligonucleotides with Particular Base Sequences from the cDNA Encoding Proteins of *Mycobacterium bovis* BCG Induce Interferons and Activate Natural Killer Cells," *Microbiol. Immunol.* 36(1):55-66.

Tung, C-H. et al. (1991). "Preparation of Oligonucleotide-Peptide Conjugates," *Bioconjug. Chem.* 2:464-465.

Van Do, T. et al. (1999). "Expression and Analysis of Recombinant Salmon Parvalbumin, the Major Allergen in Atlantic Salmon (*Salmo salar*)," *Scand. J. Immunol.* 50:619-625.

Verthelyi, D. et al. (2001). "Human Peripheral Blood Cells Differentially Recognize and Respond to Two Distinct CpG Motifs," *J. Immunol.* 166(4):2372-2377.

Wang, S. et al. (1994). "Circular RNA Oligonucleotides. Synthesis, Nucleic Acid Binding Properties, and a Comparison with Circular DNAs," *Nucleic Acids Res.* 22(12):2326-2333.

Warner, B. D. et al. (1984). "Laboratory Methods: Construction and Evaluation of an Instrument for the Automated Synthesis of Oligodeoxyribonucleotides," *DNA* 3(5):401-411.

Watwe, R. M. et al. (Apr. 1995). "Manufacture of Liposomes: A Review," *Current Science* 68(7):715-724.

Weeratna, R. et al. (1998). "Reduction of Antigen Expression from DNA Vaccines by Coadministered Oligodeoxynucleotides," *Anti. and Nucleic Acid Drug Develop.* 8:351-356.

Weiner, G. J. et al. (Sep. 1997). "Immunostimulatory Oligodeoxynucleotides Containing the CpG Motif are Effective as Immune Adjuvants in Tumor Antigen Immunization," *PNAS USA* 94:10833-10837.

Weiner (2000). *J. Leucocyte Biology* 68:456-463.

Weir, D.M., ed. *Handbook of Experimental Immunology in Four Volumes*, "Volume 4: Applications of Immunological Methods in Biomedical Sciences," Blackwell Scientific Publications: pp. v-x (Table of Contents).

Widhe, M. et al. (1998). "IgG Subclasses in Lyme Borreliosis: A Study of Specific IgG Subclass Distribution in an Interferon-γ-Predominated Disease," *Scand. J. Immunol.* 47:575-581.

Wild, D., ed. (1994). *The Immunoassay Handbook*, Stockton Press: pp. v-xvi (Table of Contents).

Wooldridge, J. E. et al. (Apr. 1997). "Immunostimulatory Oligodeoxynucleotides Containing CpG Motifs Enhance the Efficacy of Monoclonal Antibody Therapy of Lymphoma," *Blood* 89(8):2994-2998.

Yamamoto, S. et al. (Jun. 1992). "Unique Palindromic Sequences in Synthetic Oligonucleotides are Required to Induce INF and Augment INF-Mediated Natural Killer Activity," *J. Immunol.* 148(12):4072-4076.

Yamamoto, T. et al. (1994a). "Ability of Oligonucleotides with Certain Palindromes to Induce Interferon Production and Augment Natural Killer Cell Activity is Associated with Their Base Length," *Anti. Res. and Develop.* 4:119-122.

Yamamoto, T. et al. (1994b). "Synthetic Oligonucleotides with Certain Palindromes Stimulate Interferon Production of Human Peripheral Blood Lymphocytes in Vitro," *Jpn. J. Cancer Res.* 85:775-779.

Yanagawa, H. et al. (Feb. 1988). "Analysis of Superhelical Structures of Nucleic Acid-Lipid Conjugates by Image Processing," *Nucleic Acids Symp. Series* 19:189-192.

Yi, A-K. et al. (Jan. 1996). "IFN-γ Promotes IL-6 and IgM Secretion in Response to CpG Motifs in Bacterial DNA and Oligodeoxynucleotides," *J. Immunol.* 156(2):558-564.

Yi, A-K. et al. (Feb. 1998a). "CpG DNA Rescue from Anti-IgM-Induced WEHI-231 B Lymphoma Apoptosis Via Modulation of IκBα and IκBβ and Sustained Activation of Nuclear Factor-κB/c-Rel," *J. Immunol.* 160(3):1240-1245.

Yi, A-K. et al.(May 1, 1998b). "CpG Motifs in Bacterial DNA Activate Leukocytes Through the pH-Dependent Generation of Reactive Oxygen Species," *J. Immunol.* 160(10):4755-4761.

Yi, A-K. et al. (Jun. 1998c). "CpG Oligodeoxyribonucleotides Rescue Mature Spleen B Cells from Spontaneous Apoptosis and Promote Cell Cycle Entry," *J. Immunol.* 160(12):5898-5906.

Yi, A-K. et al. (1998d). "Rapid Induction of Mitogen-Activated Protein Kinases by Immune Stimulatory CpG DNA," *J. Immunol.* 161(9):4493-4497.

Zhao, Q. et al. (1996). "Effect of Different Chemically Modified Oligodeoxynucleotides on Immune Stimulation," *Biochem. Pharmacol.* 51(2):173-182.

Zimmermann, S. et al. (1998). "CpG Oligodeoxynucleotides Trigger Protective and Curative Th1 Responses in Lethal Murine Leishmaniasis," *J. Immunol.* 160(8):3627-3630.

Zon, G. (1993). "Oligonucleoside Phosphorothioates," Chapter 8 in *Protocols for Oligonucleotides and Analogs, Synthesis and Properties*, Sudhir Agrawal, ed., Humana Press, Totowa, N.J., pp. 165-189.

Zuckermann, R. et al. (1987). "Efficient Methods for Attachment of Thiol Specific Probes to the 3'-Ends of Synthetic Oligodeoxyribonucleotides," *Nucleic Acids Res.* 15(13):5305-5321.

\* cited by examiner

IMMUNOMODULATORY POLYNUCLEOTIDES AND METHODS OF USING THE SAME

CROSS-REFERENCE TO RELATED APPLICATIONS

This application is a continuation of U.S. patent application Ser. No. 10/033,243, filed on Dec. 27, 2001 and claims the priority benefit of U.S. Provisional application 60/258,675, filed Dec. 27, 2000, the disclosures of which are hereby incorporated by reference in their entirety.

TECHNICAL FIELD

The present invention relates to immunomodulatory polynucleotides comprising an immunostimulatory oligonucleotide sequence (ISS). It also relates to the administration of the polynucleotides to modulate an immune response.

BACKGROUND ART

The type of immune response generated to infection or other antigenic challenge can generally be distinguished by the subset of T helper (Th) cells involved in the response. The Th1 subset is responsible for classical cell-mediated functions such as delayed-type hypersensitivity and activation of cytotoxic T lymphocytes (CTLs), whereas the Th2 subset functions more effectively as a helper for B-cell activation. The type of immune response to an antigen is generally influenced by the cytokines produced by the cells responding to the antigen. Differences in the cytokines secreted by Th1 and Th2 cells are believed to reflect different biological functions of these two subsets. See, for example, Romagnani (2000) *Ann. Allergy Asthma Immunol.* 85:9-18.

The Th1 subset may be particularly suited to respond to viral infections, intracellular pathogens, and tumor cells because it secretes IL-2 and IFN-γ, which activate CTLs. The Th2 subset may be more suited to respond to free-living bacteria and helminthic parasites and may mediate allergic reactions, since IL-4 and IL-5 are known to induce IgE production and eosinophil activation, respectively. In general, Th1 and Th2 cells secrete distinct patterns of cytokines and so one type of response can moderate the activity of the other type of response. A shift in the Th1/Th2 balance can result in an allergic response, for example, or, alternatively, in an increased CTL response.

For many infectious diseases, such as tuberculosis and malaria, Th2-type responses are of little protective value against infection. Proposed vaccines using small peptides derived from the target antigen and other currently used antigenic agents that avoid use of potentially infective intact viral particles, do not always elicit the immune response necessary to achieve a therapeutic effect. The lack of a therapeutically effective human immunodeficiency virus (HIV) vaccine is an unfortunate example of this failure. Protein-based vaccines typically induce Th2-type immune responses, characterized by high titers of neutralizing antibodies but without significant cell-mediated immunity.

Moreover, some types of antibody responses are inappropriate in certain indications, most notably in allergy where an IgE antibody response can result in anaphylactic shock. Generally, allergic responses also involve Th2-type immune responses. Allergic responses, including those of allergic asthma, are characterized by an early phase response, which occurs within seconds to minutes of allergen exposure and is characterized by cellular degranulation, and a late phase response, which occurs 4 to 24 hours later and is characterized by infiltration of eosinophils into the site of allergen exposure. Specifically, during the early phase of the allergic response, allergen cross-links IgE antibodies on basophils and mast cells, which in turn triggers degranulation and the subsequent release of histamine and other mediators of inflammation from mast cells and basophils. During the late phase response, eosinophils infiltrate into the site of allergen exposure (where tissue damage and dysfunction result).

Antigen immunotherapy for allergic disorders involves the subcutaneous injection of small, but gradually increasing amounts, of antigen. Such immunization treatments present the risk of inducing IgE-mediated anaphylaxis and do not efficiently address the cytokine-mediated events of the allergic late phase response. Thus far, this approach has yielded only limited success.

Administration of certain DNA sequences, generally known as immunostimulatory sequences or "ISS," induces an immune response with a Th1-type bias as indicated by secretion of Th1-associated cytokines. Administration of an immunostimulatory polynucleotide with an antigen results in a Th1-type immune response to the administered antigen. Roman et al. (1997) *Nature Med.* 3:849-854. For example, mice injected intradermally with *Escherichia coli* (*E. coli*) β-galactosidase (β-Gal) in saline or in the adjuvant alum responded by producing specific IgG1 and IgE antibodies, and CD4$^+$ cells that secreted IL-4 and IL-5, but not IFN-γ, demonstrating that the T cells were predominantly of the Th2 subset. However, mice injected intradermally (or with a tyne skin scratch applicator) with plasmid DNA (in saline) encoding β-Gal and containing an ISS responded by producing IgG2a antibodies and CD4$^+$ cells that secreted IFN-γ, but not IL-4 and IL-5, demonstrating that the T cells were predominantly of the Th1 subset. Moreover, specific IgE production by the plasmid DNA-injected mice was reduced 66-75%. Raz et al. (1996) *Proc. Natl. Acad. Sci. USA* 93:5141-5145. In general, the response to naked DNA immunization is characterized by production of IL-2, TNFα and IFN-γ by antigen-stimulated CD4$^+$ T cells, which is indicative of a Th1-type response. This is particularly important in treatment of allergy and asthma as shown by the decreased IgE production. The ability of immunostimulatory polynucleotides to stimulate a Th1-type immune response has been demonstrated with bacterial antigens, viral antigens and with allergens (see, for example, WO 98/55495).

Other references describing ISS include: Krieg et al. (1989) *J. Immunol.* 143:2448-2451; Tokunaga et al. (1992) *Microbiol. Immunol.* 36:55-66; Kataoka et al. (1992) *Jpn. J. Cancer Res.* 83:244-247; Yamamoto et al. (1992) *J. Immunol.* 148:4072-4076; Mojcik et al. (1993) *Clin. Immuno. and Immunopathol.* 67:130-136; Branda et al. (1993) *Biochem. Pharmacol.* 45:2037-2043; Pisetsky et al. (1994) *Life Sci.* 54(2):101-107; Yamamoto et al. (1994a) *Antisense Research and Development.* 4:119-122; Yamamoto et al. (1994b) *Jpn. J. Cancer Res.* 85:775-779; Raz et al. (1994) *Proc. Natl. Acad. Sci. USA* 91:9519-9523; Kimura et al. (1994) *J. Biochem. (Tokyo)* 116:991-994; Krieg et al. (1995) *Nature* 374:546-549; Pisetsky et al. (1995) *Ann. N.Y. Acad. Sci.* 772:152-163; Pisetsky (1996a) *J. Immunol.* 156:421-423; Pisetsky (1996b) *Immunity* 5:303-310; Zhao et al. (1996) *Biochem. Pharmacol.* 51:173-182; Yi et al. (1996) *J. Immunol.* 156:558-564; Krieg (1996) *Trends Microbiol.* 4(2):73-76; Krieg et al. (1996) *Antisense Nucleic Acid Drug Dev.* 6:133-139; Klinman et al. (1996) *Proc. Natl. Acad. Sci. USA.* 93:2879-2883; Raz et al. (1996); Sato et al. (1996) *Science* 273:352-354; Stacey et al. (1996) *J. Immunol.* 157:2116-2122; Ballas et al. (1996) *J. Immunol.* 157:1840-1845; Branda et al. (1996)

J. Lab. Clin. Med. 128:329-338; Sonehara et al. (1996) J. Interferon and Cytokine Res. 16:799-803; Klinman et al. (1997) J. Immunol. 158:3635-3639; Sparwasser et al. (1997) Eur. J. Immunol. 27:1671-1679; Roman et al. (1997); Carson et al. (1997) J. Exp. Med. 186:1621-1622; Chace et al. (1997) Clin. Immunol. and Immunopathol. 84:185-193; Chu et al. (1997) J. Exp. Med. 186:1623-1631; Lipford et al. (1997a) Eur. J. Immunol. 27:2340-2344; Lipford et al. (1997b) Eur. J. Immunol. 27:3420-3426; Weiner et al. (1997) Proc. Natl. Acad. Sci. USA 94:10833-10837; Macfarlane et al. (1997) Immunology 91:586-593; Schwartz et al. (1997) J. Clin. Invest. 100:68-73; Stein et al. (1997) Antisense Technology, Ch. 11 pp. 241-264, C. Lichtenstein and W. Nellen, Eds., IRL Press; Wooldridge et al. (1997) Blood 89:2994-2998; Leclerc et al. (1997) Cell. Immunol. 179:97-106; Kline et al. (1997) J. Invest. Med. 45(3):282A; Yi et al. (1998a) J. Immunol. 160: 1240-1245; Yi et al. (1998b) J. Immunol. 160:4755-4761; Yi et al. (1998c) J. Immunol. 160:5898-5906; Yi et al. (1998d) J. Immunol. 161:4493-4497; Krieg (1998) Applied Antisense Oligonucleotide Technology Ch. 24, pp. 431-448, C. A. Stein and A. M. Krieg, Eds., Wiley-Liss, Inc.; Krieg et al. (1998a) Trends Microbiol. 6:23-27; Krieg et al. (1998b) J. Immunol. 161:2428-2434; Krieg et al. (1998c) Proc. Natl. Acad. Sci. USA 95:12631-12636; Spiegelberg et al. (1998) Allergy 53(45S):93-97; Horner et al. (1998) Cell Immunol. 190:77-82; Jakob et al. (1998) J. Immunol. 161:3042-3049; Redford et al. (1998) J. Immunol. 161:3930-3935; Weeratna et al. (1998) Antisense & Nucleic Acid Drug Development 8:351-356; McCluskie et al. (1998) J. Immunol. 161(9):4463-4466; Gramzinski et al. (1998) Mol. Med. 4:109-118; Liu et al. (1998) Blood 92:3730-3736; Moldoveanu et al. (1998) Vaccine 16: 1216-1224; Brazolot Milan et al. (1998) Proc. Natl. Acad. Sci. USA 95:15553-15558; Briode et al. (1998) J. Immunol. 161:7054-7062; Briode et al. (1999) Int. Arch. Allergy Immunol. 118:453-456; Kovarik et al. (1999) J. Immunol. 162:1611-1617; Spiegelberg et al. (1999) Pediatr. Pulmonol. Suppl. 18:118-121; Martin-Orozco et al. (1999) Int. Immunol. 11:1111-1118; EP 468,520; WO 96/02555; WO 97/28259; WO 98/16247; WO 98/18810; WO 98/37919; WO 98/40100; WO 98/52581; WO 98/55495; WO 98/55609 and WO 99/11275. See also Elkins et al. (1999) J. Immunol. 162:2291-2298, WO 98/52962, WO 99/33488, WO 99/33868, WO 99/51259 and WO 99/62923. See also Zimmermann et al. (1998) J. Immunol. 160:3627-3630; Krieg (1999) Trends Microbiol. 7:64-65 and U.S. Pat. Nos. 5,663, 153, 5,723,335 and 5,849,719. See also Liang et al. (1996) J. Clin. Invest. 98:1119-1129; Bohle et al. (1999) Eur. J. Immunol. 29:2344-2353 and WO 99/56755. See also WO 99/61056; WO 00/06588; WO 00/16804; WO 00/21556; WO 00/54803; WO 00/61151; WO 00/67023; WO 00/67787 and U.S. Pat. No. 6,090,791. See also Manzel et al. (1999) Antisense Nucl. Acid Drug Dev. 9:459-464; Verthelyi et al. (2001) J. Immunol. 166:2372-2377; WO 01/15726; WO 01/12223; WO 01/22972; WO 01/22990; WO 01/35991; WO 01/51500; WO 01/54720; U.S. Pat. Nos. 6,174,872, 6,194,388, 6,207, 646, 6,214,806, 6,218,371, 6,239,116.

ISS generally include a CG sequence. Nucleotides flanking the CG of an ISS also appear to play a role in the immunomodulatory activity of the polynucleotide. There remains a need for continued identification of ISS for use in immunomodulatory polynucleotides.

All patents, patent applications, and publications cited herein are hereby incorporated by reference in their entirety.

DISCLOSURE OF THE INVENTION

The invention relates to immunostimulatory sequences (ISS) and immunomodulatory polynucleotides containing ISS and methods for modulating immune responses in individuals using these polynucleotides, particularly humans.

In one aspect, the invention provides immunomodulatory polynucleotides which comprise an immunostimulatory sequence (ISS). In certain embodiments, the invention includes compositions which comprise an immunomodulatory polynucleotide of the invention and a pharmaceutically acceptable excipient.

In one aspect, the immunomodulatory polynucleotide of the invention comprises an ISS comprising a sequence of the formula 5'-$X_1 X_2$ A $X_3$ C G $X_4$ T C G-3' (SEQ ID NO: 62) wherein $X_1$ is T, G, C or Z (Z=5-bromocytosine), wherein $X_2$ is T, G, A or U, wherein $X_3$ is T, A or C, wherein $X_4$ is T, G or U and wherein the formula is not 5'-TGAACGTTCG-3' (SEQ ID NO: 63) or 5'-GGAACGTTCG-3' (SEQ ID NO: 64).

In another aspect, the immunomodulatory polynucleotide of the invention comprises an ISS comprising a sequence of the formula 5'-$X_1X_2$ A $X_3$ Z G $X_4$ T C G-3' (SEQ ID NO: 65) wherein Z is 5-bromocytosine, wherein $X_1$ is T, G, C or Z (Z=5-bromocytosine), wherein $X_2$ is T, G, A or U, wherein $X_3$ is T, A or C, wherein $X_4$ is T, G or U and wherein the formula is not 5'-TGAAZGTTCG-3' (SEQ ID NO: 66; Z=5-bromocytosine).

In another aspect, the immunomodulatory polynucleotide of the invention comprises at least one of the following sequences: TGAACGUTCG (SEQ ID NO: 67), GAACCGT-TCG (SEQ ID NO: 75), CGAACGTTCG (SEQ ID NO: 77), ZGAAZGUTCG (SEQ ID NO: 93) and GAAAZGUTCG (SEQ ID NO: 89), wherein Z is 5-bromocytosine.

In another aspect, with respect to any of the ISS disclosed herein, the immunomodulatory polynucleotide of the invention may further comprise one or more TCG and/or T, 5-bromocytosine, G sequence(s), preferably 5' (or upstream) of the ISS.

In another aspect, with respect to any of the ISS disclosed herein, the immunomodulatory polynucleotide of the invention may further comprise one or more TCGA and/or T, 5-bromocytosine, G, A sequence(s).

In another aspect, any immunomodulatory polynucleotide of the invention is stabilized.

In another aspect, the invention provides an immunomodulatory polynucleotide/microcarrier complex including an immunomodulatory polynucleotide of the invention linked to a microcarrier, in particular to a microcarrier less than 10 μm in size.

In another aspect, the invention provides compositions comprising any of the immunomodulatory polynucleotides (including complexed with a microcarrier) described herein. The compositions may also include, for example, a pharmaceutically acceptable excipient or any of a number of other components, such as an antigen.

In another aspect, the invention provides methods of modulating an immune response in an individual, comprising administering to an individual an immunomodulatory polynucleotide of the invention in an amount sufficient to modulate an immune response in said individual. Immunomodulation according to the methods of the invention may be practiced on individuals including those suffering from a disorder associated with a Th2-type immune response (e.g., allergies or allergy-induced asthma), individuals receiving vaccines such as therapeutic vaccines (e.g., vaccines comprising an allergy epitope, a mycobacterial epitope, or a tumor associated epitope) or prophylactic vaccines, individuals with cancer and individuals having an infectious disease.

In a further aspect, the invention provides methods of increasing interferon-gamma (IFN-γ) in an individual (or stimulating IFN-γ levels (or amount(s)) in an individual), comprising administering an effective amount of an immunomodulatory polynucleotide of the invention to the individual. Administration of an immunomodulatory polynucleotide in accordance with the invention increases IFN-γ in the individual. Suitable subjects for these methods include those individuals who could benefit from an increase of IFN-γ, or such individuals having idiopathic pulmonary fibrosis (IPF), scleroderma, cutaneous radiation-induced fibrosis, hepatic fibrosis including schistosomiasis-induced hepatic fibrosis, renal fibrosis as well as other conditions which may be improved by administration of IFN-γ.

In a further aspect, the invention provides methods of increasing interferon-alpha (IFN-α) in an individual (or stimulating IFN-α levels (or amount(s)) in an individual), comprising administering an effective amount of an immunomodulatory polynucleotide of the invention to the individual. Administration of an immunomodulatory polynucleotide in accordance with the invention increases IFN-α in the individual. Suitable subjects for these methods include those individuals having a viral infection as well as other conditions which may be improved by administration of IFN-α or an increase in amount of IFN-α.

In another aspect, the invention provides methods of ameliorating one or more symptoms of an infectious disease, comprising administering an effective amount of an immunomodulatory polynucleotide of the invention to an individual having an infectious disease. Administration of an immunomodulatory polynucleotide in accordance with the invention ameliorates one or more symptoms of the infectious disease. The infectious diseases which may be treated in accordance with the invention include infectious diseases caused by a cellular pathogen (e.g., a mycobacterial disease, malaria, leishmaniasis, toxoplasmosis, schistosomiasis or clonorchiasis), and may include or exclude viral diseases.

The invention further relates to kits, preferably for carrying out the methods of the invention. The kits of the invention generally comprise an immunomodulatory polynucleotide of the invention (generally in a suitable container), and may further include instructions for use of the immunomodulatory polynucleotide in immunomodulation of an individual, for example when the individual suffers from a disorder associated with a Th2-type immune response (e.g., allergies or allergy-induced asthma), is receiving vaccines such as therapeutic vaccines (e.g., vaccines comprising an allergy epitope, a mycobacterial epitope, or a tumor associated epitope) or prophylactic vaccines, suffers from cancer or suffers from an infectious disease. Other suitable instructions may be provided.

MODES FOR CARRYING OUT THE INVENTION

We have discovered immunomodulatory polynucleotides comprising immunostimulatory sequences (ISS) and methods for modulating immune responses in individuals, particularly humans, using these immunomodulatory polynucleotides. The compositions of the invention comprise an immunomodulatory polynucleotide comprising an ISS as described herein. Some immunomodulatory polynucleotides of the invention further include at least one TCG or T, 5-bromocytosine, G sequence. In some immunomodulatory polynucleotides, the additional TCG and/or T, 5-bromocytosine, G sequence(s) is created by the addition of a T or a TC or a T, 5-bromocytosine to the 5' end of the ISS. We have found that immunomodulatory polynucleotides comprising specific ISS efficiently modulate immune cells, including human cells. Our discovery is of particular interest because human cells can be more resistant to immunomodulation by immunomodulatory polynucleotides than cells from commonly used laboratory animals, such as mice. We have also observed that some polynucleotides of the invention effectively stimulate IFN-α, even in human cells.

The invention also provides methods for modulating an immune response in an individual by administering an immunomodulatory polynucleotide of the invention to the individual.

Further provided are kits comprising the ISS-containing polynucleotides of the invention. The kits may further comprise instructions for administering an immunomodulatory polynucleotide of the invention for immunomodulation in a subject and immunomodulatory polynucleotides.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (D. Wild, ed., Stockton Press NY, 1994); *Bioconjugate Techniques* (Greg T. Hermanson, ed., Academic Press, 1996); and *Methods of Immunological Analysis* (R. Masseyeff, W. H. Albert, and N. A. Staines, eds., Weinheim: VCH Verlags gesellschaft mbH, 1993).

Definitions

As used herein, the singular form "a", "an", and "the" includes plural references unless indicated otherwise. For example, "an" ISS includes one or more ISS.

As used interchangeably herein, the terms "polynucleotide" and "oligonucleotide" include single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured, or the oligonucleotide can contain both linear and circular segments. Oligonucleotides are polymers of nucleosides joined, generally, through phosphodiester linkages, although alternate linkages, such as phosphorothioate esters may also be used in oligonucleotides. A nucleoside consists of a purine (adenine (A) or guanine (G) or derivative thereof) or pyrimidine (thymine (T), cytosine (C) or uracil (U), or derivative thereof) base bonded to a sugar. The four nucleoside units (or bases) in DNA are called deoxyadenosine, deoxyguanosine, deoxythymidine, and deoxycytidine. A nucleotide is a phosphate ester of a nucleoside.

The term "ISS" as used herein refers to polynucleotide sequences that effect and/or contribute to a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, CD4+ T lymphocytes, CD8+ T lymphocytes, B lymphocytes, and the like. Preferably, the ISS sequences preferentially activate a Th1-type response. A polynucleotide for use in the invention contains at least one ISS. As used herein, "ISS" is also a shorthand term for an ISS-containing polynucleotide, including the ISS-containing immunomodulatory polynucleotides of the invention.

The term "3'" generally refers to a region or position in a polynucleotide or oligonucleotide 3' (downstream) from another region or position in the same polynucleotide or oligonucleotide.

The term "5'" generally refers to a region or position in a polynucleotide or oligonucleotide 5' (upstream) from another region or position in the same polynucleotide or oligonucleotide.

A region, portion, or sequence which is "adjacent" to another sequence directly abuts that region, portion, or sequence. For example, an additional polynucleotide sequence which is adjacent to the ISS portion of an immunomodulatory polynucleotide directly abuts that region.

The term "immunomodulatory polynucleotide" or "IMP" or "ISS-containing polynucleotide", as used herein, refers to a polynucleotide comprising at least one ISS. In certain embodiments, the IMP is an ISS.

The term "immunomodulatory" or "modulating an immune response" as used herein includes immunostimulatory as well as immunosuppressive effects. Immunomodulation is primarily a qualitative alteration in an overall immune response, although quantitative changes may also occur in conjunction with immunomodulation. An immune response that is immunomodulated according to the present invention is one that is shifted towards a "Th1-type" immune response, as opposed to a "Th2-type" immune response. Th1-type responses are typically considered cellular immune system (e.g., cytotoxic lymphocytes) responses, while Th2-type responses are generally "humoral", or antibody-based. Th1-type immune responses are normally characterized by "delayed-type hypersensitivity" reactions to an antigen, and can be detected at the biochemical level by increased levels of Th1-associated cytokines such as IFN-γ, IFN-α, IL-2, IL-12, and TNF-β, as well as IL-6, although IL-6 may also be associated with Th2-type responses as well. Th1-type immune responses are generally associated with the production of cytotoxic lymphocytes (CTLs) and low levels or transient production of antibody. Th2-type immune responses are generally associated with higher levels of antibody production, including IgE production, an absence of or minimal CTL production, as well as expression of Th2-associated cytokines such as IL-4. Accordingly, immunomodulation in accordance with the invention may be recognized by, for example, an increase in IFN-γ and/or a decrease in IgE production in an individual treated in accordance with the methods of the invention as compared to the absence of treatment.

The term "conjugate" refers to a complex in which an ISS-containing polynucleotide and an antigen are linked. Such conjugate linkages include covalent and/or non-covalent linkages.

The term "antigen" means a substance that is recognized and bound specifically by an antibody or by a T cell antigen receptor. Antigens can include peptides, proteins, glycoproteins, polysaccharides, complex carbohydrates, sugars, gangliosides, lipids and phospholipids; portions thereof and combinations thereof. The antigens can be those found in nature or can be synthetic. Antigens suitable for administration with ISS include any molecule capable of eliciting a B cell or T cell antigen-specific response. Preferably, antigens elicit an antibody response specific for the antigen. Haptens are included within the scope of "antigen." A hapten is a low molecular weight compound that is not immunogenic by itself but is rendered immunogenic when conjugated with an immunogenic molecule containing antigenic determinants. Small molecules may need to be haptenized in order to be rendered antigenic. Preferably, antigens of the present invention include peptides, lipids (e.g. sterols, fatty acids, and phospholipids), polysaccharides such as those used in *Hemophilus influenza* vaccines, gangliosides and glycoproteins.

"Adjuvant" refers to a substance which, when added to an immunogenic agent such as antigen, nonspecifically enhances or potentiates an immune response to the agent in the recipient host upon exposure to the mixture.

The term "peptide" are polypeptides that are of sufficient length and composition to effect a biological response, e.g., antibody production or cytokine activity whether or not the peptide is a hapten. Typically, the peptides are at least six amino acid residues in length. The term "peptide" further includes modified amino acids (whether or not naturally or non-naturally occurring), such modifications including, but not limited to, phosphorylation, glycosylation, pegylation, lipidization and methylation.

"Antigenic peptides" can include purified native peptides, synthetic peptides, recombinant proteins, crude protein extracts, attenuated or inactivated viruses, cells, micro-organisms, or fragments of such peptides. An "antigenic peptide" or "antigen polypeptide" accordingly means all or a portion of a polypeptide which exhibits one or more antigenic properties. Thus, for example, an "Amb a 1 antigenic polypeptide" or "Amb a 1 polypeptide antigen" is an amino acid sequence from Amb a 1, whether the entire sequence, a portion of the sequence, and/or a modification of the sequence, which exhibits an antigenic property (i.e., binds specifically to an antibody or a T cell receptor).

A "delivery molecule" or "delivery vehicle" is a chemical moiety which facilitates, permits, and/or enhances delivery of an immunomodulatory polynucleotide to a particular site and/or with respect to particular timing. A delivery vehicle may or may not additionally stimulate an immune response.

An "allergic response to antigen" means an immune response generally characterized by the generation of eosinophils and/or antigen-specific IgE and their resultant effects. As is well-known in the art, IgE binds to IgE receptors on mast cells and basophils. Upon later exposure to the antigen recognized by the IgE, the antigen cross-links the IgE on the mast cells and basophils causing degranulation of these cells, including, but not limited, to histamine release. It is understood and intended that the terms "allergic response to antigen", "allergy", and "allergic condition" are equally appropriate for application of some of the methods of the invention. Further, it is understood and intended that the methods of the invention include those that are equally appropriate for pre-vention of an allergic response as well as treating a pre-existing allergic condition.

As used herein, the term "allergen" means an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule. A number of isolated allergens are known in the art. These include, but are not limited to, those provided in Table 1 herein.

The term "desensitization" refers to the process of the administration of increasing doses of an allergen to which the subject has demonstrated sensitivity. Examples of allergen doses used for desensitization are known in the art, see, for example, Fornadley (1998) *Otolaryngol. Clin. North Am.* 31:111-127.

"Antigen-specific immunotherapy" refers to any form of immunotherapy which involves antigen and generates an antigen-specific modulation of the immune response. In the allergy context, antigen-specific immunotherapy includes, but is not limited to, desensitization therapy.

The term "microcarrier" refers to a particulate composition which is insoluble in water and which has a size of less than about 150, 120 or 100 μm, preferably less than about 50-60 μm, preferably less than about 10 μm, preferably less than about 5, 2.5, 2 or 1.5 μm. Microcarriers include "nanocarriers", which are microcarriers having a size of less than about 1 μm, preferably less than about 500 nm. Microcarriers include solid phase particles such as particles formed from biocompatible naturally occurring polymers, synthetic polymers or synthetic copolymers, although microcarriers formed from agarose or cross-linked agarose may be included or excluded from the definition of microcarriers herein as well as other biodegradable materials known in the art. Microcarriers for use in the instant invention may be biodegradable or nonbiodegradable. Nonbiodegradable solid phase microcarriers are formed from polymers or other materials which are non-erodible and/or non-degradable under mammalian physiological conditions, such as polystyrene, polypropylene, silica, ceramic, polyacrylamide, gold, latex, hydroxyapatite, dextran, and ferromagnetic and paramagnetic materials. Biodegradable solid phase microcarriers may be formed from polymers which are degradable (e.g., poly(lactic acid), poly(glycolic acid) and copolymers thereof) or erodible (e.g., poly(ortho esters such as 3,9-diethylidene-2,4,8,10-tetraoxaspiro[5.5]undecane (DETOSU) or poly(anhydrides), such as poly(anhydrides) of sebacic acid) under mammalian physiological conditions. Microcarriers may also be liquid phase (e.g., oil or lipid based), such liposomes, iscoms (immune-stimulating complexes, which are stable complexes of cholesterol, phospholipid and adjuvant-active saponin) without antigen, or droplets or micelles found in oil-in-water or water-in-oil emulsions. Biodegradable liquid phase microcarriers typically incorporate a biodegradable oil, a number of which are known in the art, including squalene and vegetable oils. Microcarriers are typically spherical in shape, but microcarriers which deviate from spherical shape are also acceptable (e.g., ellipsoidal, rod-shaped, etc.). Due to their insoluble nature (with respect to water), microcarriers are filterable from water and water-based (aqueous) solutions.

The term "nonbiodegradable", as used herein, refers to a microcarrier which is not degraded or eroded under normal mammalian physiological conditions. Generally, a microcarrier is considered nonbiodegradable if it not degraded (i.e., loses less than 5% of its mass or average polymer length) after a 72 hour incubation at 37° C. in normal human serum.

A microcarrier is considered "biodegradable" if it is degradable or erodable under normal mammalian physiological conditions. Generally, a microcarrier is considered biodegradable if it is degraded (i.e., loses at least 5% of its mass or average polymer length) after a 72 hour incubation at 37° C. in normal human serum.

The "size" of a microcarrier is generally the "design size" or intended size of the particles stated by the manufacturer. Size may be a directly measured dimension, such as average or maximum diameter, or may be determined by an indirect assay such as a filtration screening assay. Direct measurement of microcarrier size is typically carried out by microscopy, generally light microscopy or scanning electron microscopy (SEM), in comparison with particles of known size or by reference to a micrometer. As minor variations in size arise during the manufacturing process, microcarriers are considered to be of a stated size if measurements show the microcarriers are ±about 5-10% of the stated measurement. Size characteristics may also be determined by dynamic light scattering or obscuration techniques. Alternately, microcarrier size may be determined by filtration screening assays. A microcarrier is less than a stated size if at least 97% of the particles pass through a "screen-type" filter (i.e., a filter in which retained particles are on the surface of the filter, such as polycarbonate or polyethersulfone filters, as opposed to a "depth filter" in which retained particles lodge within the filter) of the stated size. A microcarrier is larger than a stated size if at least about 97% of the microcarrier particles are retained by a screen-type filter of the stated size. Thus, at least about 97% microcarriers of about 10 μm to about 10 nm in size pass through a 10 μm pore screen filter and are retained by a 10 nm screen filter.

As above discussion indicates, reference to a size or size range for a microcarrier implicitly includes approximate variations and approximations of the stated size and/or size range. This is reflected by use of the term "about" when referring to a size and/or size range, and reference to a size or size range without reference to "about" does not mean that the size and/or size range is exact.

The term "immunomodulatory polynucleotide/microcarrier complex" or "IMP/MC complex" refers to a complex of an ISS-containing polynucleotide and a microcarrier. The components of the complex may be covalently or non-covalently linked. Non-covalent linkages may be mediated by any non-covalent bonding force, including by hydrophobic interaction, ionic (electrostatic) bonding, hydrogen bonds and/or van der Waals attractions. In the case of hydrophobic linkages, the linkage is generally via a hydrophobic moiety (e.g., cholesterol) covalently linked to the IMP.

An "individual" is a vertebrate, such as avian, and is preferably a mammal, more preferably a human. Mammals include, but are not limited to, humans, primates, farm animals, sport animals, rodents and pets.

An "effective amount" or a "sufficient amount" of a substance is that amount sufficient to effect beneficial or desired results, including clinical results, and, as such, an "effective amount" depends upon the context in which it is being applied. In the context of administering a composition that modulates an immune response to a co-administered antigen, an effective amount of an immunomodulatory polynucleotide and antigen is an amount sufficient to achieve such a modulation as compared to the immune response obtained when the antigen is administered alone. An effective amount can be administered in one or more administrations.

The term "co-administration" as used herein refers to the administration of at least two different substances sufficiently close in time to modulate an immune response. Preferably, co-administration refers to simultaneous administration of at least two different substances.

"Stimulation" of a response or parameter includes eliciting and/or enhancing that response or parameter. For example, "stimulation" of an immune response, such as Th1 response, means an increase in the response, which can arise from eliciting and/or enhancement of a response. Similarly, "stimulation" of a cytokine or cell type (such as CTLs) means an increase in the amount or level of cytokine or cell type.

An "IgE associated disorder" is a physiological condition which is characterized, in part, by elevated IgE levels, which may or may not be persistent. IgE associated disorders include, but are not limited to, allergy and allergic reactions, allergy-related disorders (described below), asthma, rhinitis, conjunctivitis, urticaria, shock, *Hymenoptera* sting allergies, and drug allergies, and parasite infections. The term also includes related manifestations of these disorders. Generally, IgE in such disorders is antigen-specific.

An "allergy-related disorder" means a disorder resulting from the effects of an antigen-specific IgE immune response. Such effects can include, but are not limited to, hypotension and shock. Anaphylaxis is an example of an allergy-related disorder during which histamine released into the circulation causes vasodilation as well as increased permeability of the capillaries with resultant marked loss of plasma from the circulation. Anaphylaxis can occur systemically, with the associated effects experienced over the entire body, and it can occur locally, with the reaction limited to a specific target tissue or organ.

The term "viral disease", as used herein, refers to a disease which has a virus as its etiologic agent. Examples of viral diseases include hepatitis B, hepatitis C, influenza, acquired immunodeficiency syndrome (AIDS), and herpes zoster.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder. Especially in the allergy context, as is well understood by those skilled in the art, palliation may occur upon modulation of the immune response against an allergen(s). Further, palliation does not necessarily occur by administration of one dose, but often occurs upon administration of a series of doses. Thus, an amount sufficient to palliate a response or disorder may be administered in one or more administrations.

An "antibody titer", or "amount of antibody", which is "elicited" by an immunomodulatory polynucleotide and antigen refers to the amount of a given antibody measured at a time point after administration of immunomodulatory polynucleotide and antigen.

A "Th1-associated antibody" is an antibody whose production and/or increase is associated with a Th1 immune response. For example, IgG2a is a Th1-associated antibody in mouse. For purposes of this invention, measurement of a Th1-associated antibody can be measurement of one or more such antibodies. For example, in human, measurement of a Th1-associated antibody could entail measurement of IgG1 and/or IgG3.

A "Th2-associated antibody" is an antibody whose production and/or increase is associated with a Th2 immune response. For example, IgG1 is a Th2-associated antibody in mouse. For purposes of this invention, measurement of a Th2-associated antibody can be measurement of one or more such antibodies. For example, in human, measurement of a Th2-associated antibody could entail measurement of IgG2 and/or IgG4.

To "suppress" or "inhibit" a function or activity, such as cytokine production, antibody production, or histamine release, is to reduce the function or activity when compared to otherwise same conditions except for a condition or parameter of interest, or alternatively, as compared to another condition. For example, a composition comprising an immunomodulatory polynucleotide and antigen which suppresses histamine release reduces histamine release as compared to, for example, histamine release induced by antigen alone. As another example, a composition comprising an immunomodulatory polynucleotide and antigen which suppresses antibody production reduces extent and/or levels of antibody as compared to, for example, extent and/or levels of antibody produced by antigen alone.

As used herein, the term "comprising" and its cognates are used in their inclusive sense; that is, equivalent to the term "including" and its corresponding cognates.

Compositions of the Invention

The invention provides immunostimulatory sequences (ISS) and immunomodulatory polynucleotides (IMP) for modulating immune response in individuals. Each immunomodulatory polynucleotide comprises at least one immunostimulatory sequence (ISS).

Compositions of the invention comprise an immunomodulatory polynucleotide alone (or a combination of two or more immunomodulatory polynucleotides) or in conjunction with another immunomodulatory agent, such as a peptide, an antigen (described below) and/or an additional adjuvant. Compositions of the invention may comprise an immunomodulatory polynucleotide and pharmaceutically acceptable excipient. Pharmaceutically acceptable excipients, including buffers, are well known in the art. *Remington: The Science and Practice of Pharmacy,* 20th edition, Mack Publishing (2000).

Upon administration, compositions comprising an antigen, an immunomodulatory polynucleotide of the invention, and optionally an adjuvant can lead to a potentiation of a immune response to the antigen and thus, can result in an enhanced immune response compared to that which results from a composition comprising the ISS and antigen alone. Adjuvants are known in the art and include, but are not limited to, oil-in-water emulsions, water-in oil emulsions, alum (aluminum salts), liposomes and microparticles, including but not limited to, polystyrene, starch, polyphosphazene and polylactide/polyglycosides. Other suitable adjuvants also include, but are not limited to, MF59, DETOX™ (Ribi), squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (IS-COMs) such as those described by Takahashi et al. (1990) *Nature* 344:873-875, as well as, lipid-based adjuvants and others described herein. For veterinary use and for production of antibodies in animals, mitogenic components of Freund's adjuvant (both complete and incomplete) can be used.

ISS-containing polynucleotides of the invention may be combined with other therapies for particular indications. For example, in addition to an ISS-containing polynucleotide, compositions of the invention may also comprise anti-malarial drugs such as chloroquine for malaria patients, leishmanicidal drugs such as pentamidine and/or allopurinol for leishmaniasis patients, anti-mycobacterial drugs such as isoniazid, rifampin and/or ethambutol for tuberculosis patients, or allergen desensitization reagents for atopic (allergy) patients.

As described herein, compositions of the invention may include ISS-containing polynucleotides and may further comprise one or more additional immunotherapeutic agents (i.e., an agent which acts via the immune system and/or is derived from the immune system) including, but not limited to, cytokine, adjuvants and antibodies. Examples of therapeutic antibodies include those used in the cancer context (e.g., anti-tumor antibodies), such as those described below.

Immunomodulatory Polynucleotides

In accordance with the present invention, the immunomodulatory polynucleotide contains at least one ISS, and can contain multiple ISSs. The ISSs can be adjacent within the polynucleotide, or they can be separated by additional nucleotide bases within the polynucleotide, or they can be overlapping within the polynucleotide. In certain embodiments, the immunomodulatory polynucleotide consists of an ISS.

ISS have been described in the art and may be readily identified using standard assays which indicate various aspects of the immune response, such as cytokine secretion, antibody production, NK cell activation and T cell proliferation. See, e.g., WO 97/28259; WO 98/16247; WO 99/11275; Krieg et al. (1995) *Nature* 374:546-549; Yamamoto et al. (1992a); Ballas et al. (1996); Klinman et al. (1997); Sato et al. (1996); Pisetsky (1996a); Shimada et al. (1986) *Jpn. J. Cancer Res.* 77:808-816; Cowdery et al. (1996) *J. Immunol.* 156: 4570-4575; Roman et al. (1997); Lipford et al. (1997a); WO 98/55495 and WO 00/61151. Accordingly, these and other methods can be used to identify, test and/or confirm immunomodulatory ISS-containing polynucleotides.

The ISS can be of any length greater than 10 bases or base pairs, preferably greater than 15 bases or base pairs, more preferably greater than 20 bases or base pairs in length and generally comprises the sequence 5'-cytosine, guanine-3'.

As is clearly conveyed herein, it is understood that, with respect to formulae described herein, any and all parameters are independently selected. For example, if x=0-2, y may be independently selected regardless of the values of x (or any other selectable parameter in a formula).

In some embodiments, an ISS may comprise a 10-mer sequence of the formula:

```
5'-X1 X2 A X3 C G X4 T C G-3'        (SEQ ID NO: 62)
``` wherein $X_1$ is T, G, C or Z (Z=5-bromocytosine), wherein $X_2$ is T, G, A or U, wherein $X_3$ is T, A or C, wherein $X_4$ is T, G or U and wherein the ISS is not 5'-TGAACGTTCG-3' (SEQ ID NO: 63) or 5'-GGAACGTTCG-3' (SEQ ID NO: 64).

In some embodiments, the ISS comprises any of the following sequences: TGAACGUTCG (SEQ ID NO: 67); TGACCGTTCG (SEQ ID NO: 68); TGATCGGTCG (SEQ ID NO: 69); TGATCGTTCG (SEQ ID NO: 70); TGAACGGTCG (SEQ ID NO: 71); GTAACGTTCG (SEQ ID NO: 72); GTATCGGTCG (SEQ ID NO: 73); GTACCGTTCG (SEQ ID NO: 74); GAACCGTTCG (SEQ ID NO: 75); ZGACCGTTCG (SEQ ID NO: 76), wherein Z=5-bromocytosine; CGAACGTTCG (SEQ ID NO: 77); CGACCGTTCG (SEQ ID NO: 78); ZGAACGTTCG (SEQ ID NO: 79), wherein Z=5-bromocytosine; TTAACGUTCG (SEQ ID NO: 80); TUAACGUTCG (SEQ ID NO: 81) and TTAACGTTCG (SEQ ID NO: 82).

In some embodiments, the immunomodulatory polynucleotide comprises the sequence

```
5'-TCGTCGAACGTTCGTTAACGTTCG-3'.     (SEQ ID NO: 1)
```

In other embodiments, the immunomodulatory polynucleotide comprises any of the following sequences:

```
5'-TGACTGTGAACGUTCGAGATGA-3';       (SEQ ID NO: 2)

5'-TCGTCGAUCGUTCGTTAACGUTCG-3';     (SEQ ID NO: 3)

5'-TCGTCGAUCGTTCGTUAACGUTCG-3';     (SEQ ID NO: 4)

5'-TCGTCGUACGUTCGTTAACGUTCG-3';     (SEQ ID NO: 5)

5'-TCGTCGAXCGUTCGTTAACGUTCG-3',     (SEQ ID NO: 6)
wherein X = 2-amino-adenine;

5'-TGATCGAACGTTCGTTAACGTTCG-3;      (SEQ ID NO: 7)

5'-TGACTGTGAACGUTCGGTATGA-3';       (SEQ ID NO: 8)

5'-TGACTGTGACCGTTCGGTATGA-3';       (SEQ ID NO: 9)

5'-TGACTGTGATCGGTCGGTATGA-3';       (SEQ ID NO: 10)

5'-TCGTCGAACGTTCGTT-3';             (SEQ ID NO: 11)

5'-TCGTCGTGAACGTTCGAGATGA-3';       (SEQ ID NO: 12)

5'-TCGTCGGTATCGGTCGGTATGA-3';       (SEQ ID NO: 13)

5'-CTTCGAACGTTCGAGATG-3';           (SEQ ID NO: 14)

5'-CTGTGATCGTTCGAGATG-3';           (SEQ ID NO: 15)

5'-TGACTGTGAACGGTCGGTATGA-3';       (SEQ ID NO: 16)

5'-TCGTCGGTACCGTTCGGTATGA-3';       (SEQ ID NO: 17)

5'-TCGTCGGAACCGTTCGGAATGA-3';       (SEQ ID NO: 18)

5'-TCGTCGAACGTTCGAGATG-3';          (SEQ ID NO: 19)

5'-TCGTCGTAACGTTCGAGATG-3';         (SEQ ID NO: 20)

5'-TGACTGTGACCGTTCGGAATGA-3';       (SEQ ID NO: 21)

5'-TCGTCGAACGTTCGAACGTTCG-3';       (SEQ ID NO: 22)

5'-TZGTZGAACGTTCGAGATG-3',          (SEQ ID NO: 23)
wherein Z = 5-bromocytosine;

5'-TCGTZGAACGTTCGAGATG-3',          (SEQ ID NO: 24)
wherein Z = 5-bromocytosine;

5'-TCGTCGACCGTTCGGAATGA-3';         (SEQ ID NO: 25)

5'-TZGTZGACCGTTCGGAATGA-3',         (SEQ ID NO: 26)
wherein Z = 5-bromocytosine;

5'-TCGTZGACCGTTCGGAATGA-3',         (SEQ ID NO: 27)
wherein Z = 5-bromocytosine;

5'-TTCGAACGTTCGTTAACGTTCG-3';       (SEQ ID NO: 28)

5'-CTTZGAACGTTCGAGATG-3',           (SEQ ID NO: 29)
wherein Z = 5-bromocytosine;.

5'-TGATCGTCGAACGTTCGAGATG-3';       (SEQ ID NO: 30)

5'-TCGTCGAACGTTCGAGATGAT-3'.        (SEQ ID NO: 132)
```

In some embodiments, an ISS of an immunomodulatory polynucleotide of the invention may comprise a 10-mer sequence of the formula:

```
5'-X1 X2 A X3 Z G X4 T C G-3'       (SEQ ID NO: 65)
``` wherein Z is 5-bromocytosine, wherein $X_1$ is T, G, C or Z (Z=5-bromocytosine), wherein $X_2$ is T, G, A or U, wherein $X_3$ is T, A or C, wherein $X_4$ is T, G or U and wherein the ISS is not 5'-TGAAZGTTCG-3' (SEQ ID NO: 66; Z=5-bromocytosine).

In some embodiments, the ISS comprises any of the following sequences (where Z is 5-bromocytosine): TGAAZGUTCG (SEQ ID NO: 83), TGACZGTTCG (SEQ ID NO: 84), TGATZGGTCG (SEQ ID NO: 85), GTATZG-GTCG (SEQ ID NO: 86), GTACZGTTCG (SEQ ID NO: 87), GAACZGTTCG (SEQ ID NO: 88), GAAAZGUTCG (SEQ ID NO: 89), ZGACZGTTCG (SEQ ID NO: 90), CGAAZGT-TCG (SEQ ID NO: 91), ZGAAZGTTCG (SEQ ID NO: 92), ZGAAZGUTCG (SEQ ID NO: 93), TTAAZGUTCG (SEQ ID NO: 94), TUAAZGUTCG (SEQ ID NO: 95) and TTAAZGTTCG (SEQ ID NO: 96).

In some embodiments, the immunomodulatory polynucleotide comprises any of the following sequences (where Z is 5-bromocytosine):

```
5'-TGACTGTGAAZGUTCGAGATGA-3';      (SEQ ID NO: 31)

5'-TCGTCGAAZGTTCGTTAAZGTTCG-3';    (SEQ ID NO: 32)

5'-TGACTGTGAAZGUTCGGTATGA-3';      (SEQ ID NO: 33)

5'-TGACTGTGAAZGUTCGGAATGA-3';      (SEQ ID NO: 34)

5'-TCGTCGAAAZGUTCGGAATGA-3';       (SEQ ID NO: 35)

5'-TCGTZGAAZGUTCGGAATGA-3'.        (SEQ ID NO: 36)
```

In some embodiments, an ISS of an immunomodulatory polynucleotide may comprise a 10-mer sequence of the formula:

```
5'-X₁ X₂ A X₃ C G X₄ T C G-3'      (SEQ ID NO: 133)
``` wherein $X_1$ is T, C or Z (Z=5-bromocytosine), wherein $X_2$ is T, G, A or U, wherein $X_3$ is T, A or C, wherein $X_4$ is T, G or U and wherein the formula is not 5'-TGAACGTTCG-3' (SEQ ID NO: 63).

In other embodiments, the immunomodulatory polynucleotide comprises any of the following sequences (where Z is 5-bromocytosine):

```
5'-TGACTGTGAAZGTTCGAGATGA-3';      (SEQ ID NO: 37)

5'-TGACTGTGAAZGTTZGAGATGA-3';      (SEQ ID NO: 38)

5'-TGACTGTGAAZGTTCCAGATGA-3';      (SEQ ID NO: 39)

5'-TGACTGTGAACGTUCGAGATGA;         (SEQ ID NO: 40)

5'-TGACTGTGAACGXTCGAGATGA-3',      (SEQ ID NO: 41)
wherein X = 5-bromouracil;

5'-TGACTGTGAAZGTTCGTUATGA-3';      (SEQ ID NO: 42)

5'-TGACTGTGAAZGTTCGGTATGA-3';      (SEQ ID NO: 43)

5'-CTGTGAACGTTCGAGATG-3';          (SEQ ID NO: 44)

5'-TZGTZGTGAACGTTCGAGATGA-3';      (SEQ ID NO: 45)

5'-TCGTZGTGAACGTTCGAGATGA-3';      (SEQ ID NO: 46)

5'-TGACTGTGAACGXTCGAGATGA-3',      (SEQ ID NO: 47)
wherein X = 4-thio-thymine;

5'-TGACTGTGAACXTTCXAGATGA-3';      (SEQ ID NO: 48)
wherein X = 6-thio-guanine;

5'-TGACTGTGAACGTTCGTUATGA-3';      (SEQ ID NO: 49)

5'-TGACTGTGAACGTTCGTTATGA-3';      (SEQ ID NO: 50)

5'-TCGTTCAACGTTCGTTAACGTTCG-3';    (SEQ ID NO: 51)

5'-TGATTCAACGTTCGTTAACGTTCG-3';    (SEQ ID NO: 52)

5'-CTGTCAACGTTCGAGATG-3';          (SEQ ID NO: 53)

5'-TCGTCGGAACGTTCGAGATG-3';        (SEQ ID NO: 55)

5'-TCGTCGGACGTTCGAGATG-3';         (SEQ ID NO: 56)

5'-TCGTCGTACGTTCGAGATG-3';         (SEQ ID NO: 57)

5'-TCGTCGTTCGTTCGAGATG-3'.         (SEQ ID NO: 58)
```

In some embodiments, with respect to any of the ISS disclosed herein, the immunomodulatory polynucleotide may further comprise one or more TCG and/or T, 5-bromocytosine, G sequence(s), preferably 5' to the ISS, for example, one or more TCG and/or T, 5-bromocytosine, G sequence 5' to the ISS; two or more TCG and/or T, 5-bromocytosine, G sequences 5' to the ISS; or three or more TCG and/or T, 5-bromocytosine, G sequences 5' to the ISS. The TCG(s) and/or T, 5-bromocytosine, G(s) may or may not be directly adjacent to the ISS. Examples of these sequences have been provided herein. For example, in some embodiments, an immunomodulatory polynucleotide of the invention may include any of the following: 5'-TCGCGAACGTTCG-3' (SEQ ID NO: 97); 5'-TCGTCGAACGTTCG-3' (SEQ ID NO: 98); 5'-TZGCGAACGTTCG-3' (SEQ ID NO: 99; wherein Z=5-bromocytosine); 5-TZGTZGAACGTTCG-3' (SEQ ID NO: 100; wherein Z=5-bromocytosine); 5'-TCGT-TAACGTTCG-3' (SEQ ID NO: 101).

In some embodiments, the additional TCG and/or T, 5-bromocytosine, G sequence(s) is immediately 5' and adjacent to the ISS, that is, 0 bases separate the TCG or T, 5-bromocytosine, G from the ISS, for example, as in 5'-T, C, G, ISS-3' or 5'-T, 5-bromocytosine, G, ISS-3'. For these embodiments, ISS may be any of the 10-mer formulas described herein. Immunomodulatory polynucleotides comprising such sequences include, for example, SEQ ID NOs. 12, 18 and 46.

In other embodiments, one base separates the additional 5' TCG and/or T, 5-bromocytosine, G sequence(s) from the ISS, for example, as in 5'-T, C, G, N, ISS-3' or 5'-T, 5-bromocytosine, G, N, ISS-3' (where N=any base). Immunomodulatory polynucleotides comprising such sequences include, for example, SEQ ID NOs. 19, 26 and 27. In other embodiments, two bases separate the additional 5' TCG and/or T, 5-bromocytosine, G sequence(s) from the ISS, for example, as in 5'-T, C, G, N,N, ISS-3' or 5'-T, 5-bromocytosine, G, N,N, ISS-3' (where N=any base). For these embodiments, ISS may be any of the 10-mer formulas described herein.

In some embodiments of the immunomodulatory polynucleotides, the additional TCG and/or T, 5-bromocytosine, G sequence(s) is created by the addition of a T or a TC or a T, 5-bromocytosine to the 5' end of the ISS. For example, in SEQ ID NO: 14, the CG of the additional TCG are the first two bases of the 10mer ISS (5'-CTTCGAACGTTCGAGATG-3' (SEQ ID NO: 14)). In another example, the G of the TCG is the first base of the 10mer ISS in SEQ ID NO: 20 (5'-TCGTC GTAACGTTCGAGATG-3' (SEQ ID NO: 20)). For embodiments such as these, ISS may be one of the 10-mer formulas described herein (e.g., SEQ ID NO: 62, SEQ ID NO: 65 or SEQ ID NO: 133). Immunomodulatory polynucleotides comprising such sequences include, for example, SEQ ID NOs. 14, 19, 20, 36 and 55.

Accordingly, for example, in some embodiments, the immunomodulatory polynucleotide comprises a T adjacent to the 5' end of the ISS 10-mer sequence SEQ ID NO: 62, wherein $X_1$ is C and $X_2$ is G. See, for example, SEQ ID NO: 19. For example, in other embodiments, the immunomodulatory polynucleotide comprises a TC adjacent to the 5' end of the ISS 10-mer sequence SEQ ID NO: 62, wherein $X_1$ is G. See, for example, SEQ ID NO: 55.

In certain embodiments where the additional TCG or T, 5-bromocytosine, G sequence is created by the addition of a T or a TC or a T, 5-bromocytosine to the 5' end of the ISS, the additional sequence may create a TCGA or a T, 5-bromocytosine, G, A sequence with the ISS. For example, in SEQ ID NO: 19, the CGA of the additional TCGA are the first three bases of the 10mer ISS (5'-5'-TCGT CGAACGTTCGAGATG-3' (SEQ ID NO: 19)). In another example, the 5-bromocytosine, G, A of the T, 5-bromocytosine, G, A sequence is the first three bases of the 10mer ISS in SEQ ID NO: 36 (5'-TCGTZGAAZGUTCGGAATGA-3' (SEQ ID NO: 36)). Accordingly, the invention includes immunomodulatory polynucleotides comprising an ISS and a TCGA sequence or T, 5-bromocytosine, G, A sequence at the 5' end of the ISS.

In some embodiments, an ISS of an immunomodulatory polynucleotide of the invention may comprise the formula:

$$5'-(TCG)_w\ N_y\ A\ X_3\ C\ G\ X_4\ T\ C\ G-3'\quad (SEQ\ ID\ NO:\ 126)$$

wherein w is 1-2, wherein y is 0-2, wherein N is any base, wherein $X_3$ is T, A or C, wherein $X_4$ is T, G or U. Immunomodulatory polynucleotides comprising such ISS sequences include, but are not limited to, SEQ ID Nos. 1, 11, 12, 13, 17, 18, 14, 19, 55, 20, 22, 25, 28 and 30.

In some embodiments, the ISS comprises any of the following sequences:

| | |
|---|---|
| TCGAACGTTCG, | (SEQ ID NO: 102) |
| TCGTCGAACGTTCG, | (SEQ ID NO: 98) |
| TCGTGAACGTTCG, | (SEQ ID NO: 103) |
| TCGGTATCGGTCG, | (SEQ ID NO: 104) |
| TCGGTACCGTTCG, | (SEQ ID NO: 105) |
| TCGGAACCGTTCG, | (SEQ ID NO: 106) |
| TCGGAACGTTCG, | (SEQ ID NO: 107) |
| TCGTCGGAACGTTCG, | (SEQ ID NO: 108) |
| TCGTAACGTTCG, | (SEQ ID NO: 109) |
| TCGTCGGAACGTTCG, | (SEQ ID NO: 108) |
| TCGACCGTTCG, | (SEQ ID NO: 110) |
| TCGTCGACCGTTCG, | (SEQ ID NO: 111) |
| TCGTTAACGTTCG. | (SEQ ID NO: 101) |

In some embodiments, an ISS of an immunomodulatory polynucleotide may comprise the formula:

$$5'-(TXG)_z\ N_y\ A\ X_3\ C\ G\ X_4\ T\ C\ G-3'\quad (SEQ\ ID\ NO:\ 127)$$

wherein z is 1-2, wherein y is 0-2, wherein X is 5-bromocytosine, wherein N is any base, wherein $X_3$ is T, A or C, wherein $X_4$ is T, G or U. Immunomodulatory polynucleotides comprising such ISS sequences include, but are not limited to, SEQ ID Nos. 45, 23, 26 and 29.

In some embodiments, the ISS comprises any of the following sequences (where X is 5-bromocytosine): TXCTGAACGTTCG (SEQ ID NO: 112), TXCTXCTGAACGTTCG (SEQ ID NO: 113), TXCAACGTTCG (SEQ ID NO: 114), TXCTXCAACGTTCG (SEQ ID NO: 115), TXGACCGTTCG (SEQ ID NO: 116), TXCTXCACCGTTCG (SEQ ID NO: 54).

In some embodiments, an ISS of an immunomodulatory polynucleotide may comprise the formula:

$$5'-T\ C\ G\ T\ X\ G\ N_y\ A\ X_3\ C\ G\ X_4\ T\ C\ G-3'\quad (SEQ\ ID\ NO:\ 128)$$

wherein y is 0-2, wherein X is 5-bromocytosine, wherein N is any base, wherein $X_3$ is T, A or C, wherein $X_4$ is T, G or U. Immunomodulatory polynucleotides comprising such ISS sequences include, but are not limited to, SEQ ID NOs. 46, 24 and 27.

In some embodiments, the ISS of an immunomodulatory polynucleotide comprises any of the following sequences (where X is 5-bromocytosine): TCGTXGTGAACGTTCG (SEQ ID NO: 117), TCGTXGAACGTTCG (SEQ ID NO: 118), TCGTXGACCGTTCG (SEQ ID NO: 119).

In some embodiments, an ISS of an immunomodulatory polynucleotide may comprise the formula:

$$5'-(TCG)_w\ N_y\ A\ X_3\ X\ G\ X_4\ T\ C\ G-3'\quad (SEQ\ ID\ NO:\ 129)$$

wherein w is 1-2, wherein y is 0-2, wherein N is any base, wherein $X_3$ is T, A, or C, wherein X is 5-bromocytosine, wherein $X_4$ is T, G or U. Immunomodulatory polynucleotides comprising such an ISS include, but are not limited to, SEQ ID NO: 35. In some embodiments, the ISS comprises the sequence TCGGAAAXGTTCG (SEQ ID NO: 120) or TCGAAXGTTCG (SEQ ID NO: 121), where X is 5-bromocytosine.

In some embodiments, an ISS of an immunomodulatory polynucleotide may comprise the formula:

$$5'-(TXG)_z\ N_y\ A\ X_3\ X\ G\ X_4\ T\ C\ G-3'\quad (SEQ\ ID\ NO:\ 130)$$

wherein z is 1-2, wherein y is 0-2, wherein X is 5-bromocytosine, wherein N is any base, wherein $X_3$ is T, A or C, wherein $X_4$ is T, G or U. In some embodiments, the ISS comprises the sequence TXGAAXGUTCG (SEQ ID NO: 122) or TXGAAXGTTCG (SEQ ID NO: 123), where X is 5-bromocytosine.

In some embodiments, an ISS of an immunomodulatory polynucleotide may comprise the formula:

$$5'-T\ C\ G\ T\ X\ G\ N_y\ A\ X_3\ X\ G\ X_4\ T\ C\ G-3'\quad (SEQ\ ID\ NO:\ 131)$$

wherein y is 0-2, wherein X is 5-bromocytosine, wherein N is any base, wherein $X_3$ is T, A or C, wherein $X_4$ is T, G or U. Immunomodulatory polynucleotides comprising such an ISS sequence include, but are not limited to, SEQ ID NO: 36. In some embodiments, the ISS comprises the sequence TCGTXGAAXGUTCG (SEQ ID NO: 124) or TCGTXGAAXGTTCG (SEQ ID NO: 125), where X is 5-bromocytosine.

An ISS and/or immunomodulatory polynucleotide may contain modifications. Modifications of ISS include any known in the art, but are not limited to, modifications of the 3'OH or 5'OH group, modifications of the nucleotide base, modifications of the sugar component, and modifications of the phosphate group. Various such modifications are described below.

An ISS and/or immunomodulatory polynucleotide may be single stranded or double stranded DNA, as well as single or double-stranded RNA or other modified polynucleotides. An ISS may or may not include one or more palindromic regions, which may be present in the decameric motifs described above or may extend beyond the motifs. An ISS may comprise additional flanking sequences, some of which are described herein. An ISS may contain naturally-occurring or modified, non-naturally occurring bases, and may contain modified sugar, phosphate, and/or termini. For example, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. Preferably, oligonucleotides of the present invention comprise phosphorothioate backbones. Sugar modifications known in the field, such as 2'-alkoxy-RNA analogs, 2'-amino-RNA analogs and 2'-alkoxy- or amino-RNA/DNA chimeras and others described herein, may also be made and combined with any phosphate modification. Examples of base modifications (discussed further below) include, but are not limited to, addition of an electron-withdrawing moiety to C-5 and/or C-6 of a cytosine of the ISS (e.g., 5-bromocytosine, 5-chlorocytosine, 5-fluorocytosine, 5-iodocytosine) and C-5 and/or C-6 of a uracil of the ISS (e.g., 5-bromouracil, 5-chlorouracil, 5-fluorouracil, 5-iodouracil). See, for example, International Patent Application No. WO 99/62923.

The ISS and/or immunomodulatory polynucleotide can be synthesized using techniques and nucleic acid synthesis equipment which are well known in the art including, but not limited to, enzymatic methods, chemical methods, and the degradation of larger oligonucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Oligonucleotide degradation can be accomplished through the exposure of an oligonucleotide to a nuclease, as exemplified in U.S. Pat. No. 4,650,675.

The ISS and/or immunomodulatory polynucleotide can also be isolated using conventional polynucleotide isolation procedures. Such procedures include, but are not limited to, hybridization of probes to genomic or cDNA libraries to detect shared nucleotide sequences, antibody screening of expression libraries to detect shared structural features and synthesis of particular native sequences by the polymerase chain reaction.

Circular immunomodulatory polynucleotide can be isolated, synthesized through recombinant methods, or chemically synthesized. Where the circular IMP is obtained through isolation or through recombinant methods, the IMP will preferably be a plasmid. The chemical synthesis of smaller circular oligonucleotides can be performed using any method described in the literature. See, for instance, Gao et al. (1995) Nucleic Acids Res. 23:2025-2029; and Wang et al. (1994) Nucleic Acids Res. 22:2326-2333.

The techniques for making oligonucleotides and modified oligonucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in Protocols for Oligonucleotides and Analogs, Synthesis and Properties (Agrawal, ed.) Humana Press, Totowa, N.J.; Warner et al. (1984) DNA 3:401 and U.S. Pat. No. 4,458,066.

The ISS and/or immunomodulatory polynucleotide can also contain phosphate-modified oligonucleotides, some of which are known to stabilize the polynucleotide. Accordingly, some embodiments includes stabilized immunomodulatory polynucleotides. Synthesis of polynucleotides containing modified phosphate linkages or non-phosphate linkages is also known in the art. For a review, see Matteucci (1997) "Oligonucleotide Analogs: an Overview" in Oligonucleotides as Therapeutic Agents, (D. J. Chadwick and G. Cardew, ed.) John Wiley and Sons, New York, N.Y. The phosphorous derivative (or modified phosphate group) which can be attached to the sugar or sugar analog moiety in the oligonucleotides of the present invention can be a monophosphate, diphosphate, triphosphate, alkylphosphonate, phosphorothioate, phosphorodithioate, phosphoramidate or the like. The preparation of the above-noted phosphate analogs, and their incorporation into nucleotides, modified nucleotides and oligonucleotides, per se, is also known and need not be described here in detail. Peyrottes et al. (1996) Nucleic Acids Res. 24:1841-1848; Chaturvedi et al. (1996) Nucleic Acids Res. 24:2318-2323; and Schultz et al. (1996) Nucleic Acids Res. 24:2966-2973. For example, synthesis of phosphorothioate oligonucleotides is similar to that described above for naturally occurring oligonucleotides except that the oxidation step is replaced by a sulfurization step (Zon (1993) "Oligonucleoside Phosphorothioates" in Protocols for Oligonucleotides and Analogs, Synthesis and Properties (Agrawal, ed.) Humana Press, pp. 165-190). Similarly the synthesis of other phosphate analogs, such as phosphotriester (Miller et al. (1971) JACS 93:6657-6665), non-bridging phosphoramidates (Jager et al. (1988) Biochem. 27:7247-7246), N3' to P5' phosphoramidiates (Nelson et al. (1997) JOC 62:7278-7287) and phosphorodithioates (U.S. Pat. No. 5,453,496) has also been described. Other non-phosphorous based modified oligonucleotides can also be used (Stirchak et al. (1989) Nucleic Acids Res. 17:6129-6141). Oligonucleotides with phosphorothioate backbones can be more immunogenic than those with phosphodiester backbones and appear to be more resistant to degradation after injection into the host. Braun et al. (1988) J. Immunol. 141:2084-2089; and Latimer et al. (1995) Mol. Immunol. 32:1057-1064.

ISS and/or immunomodulatory polynucleotides used in the invention can comprise one or more ribonucleotides (containing ribose as the only or principal sugar component), deoxyribonucleotides (containing deoxyribose as the principal sugar component), or, as is known in the art, modified sugars or sugar analogs can be incorporated in the ISS and/or immunomodulatory polynucleotide. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the ISS and/or IMP, the sugar moiety is preferably the furanoside of ribose, deoxyribose, arabinose or 2'-O-alkylribose, and the sugar can be attached to the respective heterocyclic bases either in α or β anomeric configuration. Sugar modifications include, but are not limited to, 2'-alkoxy-RNA analogs, 2'-amino-RNA analogs and 2'-alkoxy- or amino-RNA/DNA chimeras. For example, a sugar modification in the ISS and/or immunomodulatory polynucleotide includes, but is not limited to, 2-aminodeoxyadenosine. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications may also be made and combined with any phosphate modification in the preparation of an ISS and/or immunomodulatory polynucleotide.

The heterocyclic bases, or nucleic acid bases, which are incorporated in the ISS and/or immunomodulatory polynucleotide can be the naturally-occurring principal purine and pyrimidine bases, (namely uracil, thymine, cytosine, adenine and guanine, as mentioned above), as well as naturally-occurring and synthetic modifications of said principal bases.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the ISS and/or immunomodulatory polynucleotide can include one or several heterocyclic bases other than the principal five base components of naturally-occurring nucleic acids. Preferably, however, the heterocyclic base in the ISS and/or IMP includes, but is not limited to, uracil-5-yl, cytosin-5-yl, adenin-7-yl, adenin-8-yl, guanin-7-yl, guanin-8-yl, 4-aminopyrrolo[2,3-d]pyrimidin-5-yl, 2-amino-4-oxopyrolo[2,3-d]pyrimidin-5-yl, 2-amino-4-oxopyrrolo[2,3-d]pyrimidin-3-yl groups, where the purines are attached to the sugar moiety of the ISS and/or IMP via the 9-position, the pyrimidines via the 1-position, the pyrrolopyrimidines via the 7-position and the pyrazolopyrimidines via the 1-position.

The ISS and/or immunomodulatory polynucleotide may comprise at least one modified base. As used herein, the term "modified base" is synonymous with "base analog", for example, "modified cytosine" is synonymous with "cytosine analog." Similarly, "modified" nucleosides or nucleotides are herein defined as being synonymous with nucleoside or nucleotide "analogs." Examples of base modifications include, but are not limited to, addition of an electron-withdrawing moiety to C-5 and/or C-6 of a cytosine of the ISS and/or IMP. Preferably, the electron-withdrawing moiety is a halogen. Such modified cytosines can include, but are not limited to, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, uracil, and any other pyrimidine analog or modified pyrimidine. Other examples of base modifications include, but are not limited to, addition of an electron-withdrawing moiety to C-5 and/or C-6 of a uracil of the ISS and/or immunomodulatory polynucleotide. Preferably, the electron-withdrawing moiety is a halogen. Such modified uracils can include, but are not limited to, 5-bromouracil, 5-chlorouracil, 5-fluorouracil, 5-iodouracil.

Other examples of base modifications include the addition of one or more thiol groups to the base including, but not limited to, 6-thio-guanine, 4-thio-thymine and 4-thio-uracil.

It is preferred that cytosines of CG motifs present in the ISS are not methylated, although other modifications and/or additions are contemplated. However, in certain embodiments the ISS may contain one or more methylated cytosines. In such embodiments it is preferred that the cytosines of the 10mer ISS sequence (i.e., the C of the CG and/or the TCG portions of the formulae described herein, e.g., SEQ ID NOs: 62, 65, 126, 127, 128, 129, 130, 131 and 133) is not methylated at position C5. However, methylation at position N4 is contemplated in those ISSs comprising methylated cytosines.

The preparation of base-modified nucleosides, and the synthesis of modified oligonucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (including, but not limited to, e.g., U.S. Pat. Nos. 4,849,513, 5,015,733, 5,118,800, 5,118,802) and can be used similarly.

In some embodiments, an immunomodulatory polynucleotide is less than about any of the following lengths (in bases or base pairs): 10,000; 5,000; 2500; 2000; 1500; 1250; 1000; 750; 500; 300; 250; 200; 175; 150; 125; 100; 75; 50; 25; 10. In some embodiments, an immunomodulatory polynucleotide is greater than about any of the following lengths (in bases or base pairs): 10; 15; 20; 25; 30; 40; 50; 60; 75; 100; 125; 150; 175; 200; 250; 300; 350; 400; 500; 750; 1000; 2000; 5000; 7500; 10000; 20000; 50000. Alternately, the immunomodulatory polynucleotide can be any of a range of sizes having an upper limit of 10,000; 5,000; 2500; 2000; 1500; 1250; 1000; 750; 500; 300; 250; 200; 175; 150; 125; 100; 75; 50; 25; or 10 and an independently selected lower limit of 10; 15; 20; 25; 30; 40; 50; 60; 75; 100; 125; 150; 175; 200; 250; 300; 350; 400; 500; 750; 1000; 2000; 5000; 7500, wherein the lower limit is less than the upper limit.

The invention also provides methods of making the immunomodulatory polynucleotides described herein. The methods may be any of those described herein. For example, the method could be synthesizing the ISS-containing polynucleotide (for example, using solid state synthesis) and may further comprise any purification step(s). Methods of purification are known in the art. Other methods of preparation include combining an immunomodulatory polynucleotide and an antigen.

Antigen

Any antigen may be co-administered with an immunomodulatory polynucleotide and/or used in compositions comprising an immunomodulatory polynucleotide and antigen (and preparation of these compositions).

In some embodiments, the antigen is an allergen. Examples of recombinant allergens are provided in Table 1. Preparation of many allergens is well-known in the art, including, but not limited to, preparation of ragweed pollen allergen Antigen E (Amb a I) (Rafnar et al. (1991) *J. Biol. Chem.* 266:1229-1236), grass allergen Lol p 1 (Tamborini et al. (1997) *Eur. J. Biochem.* 249:886-894), major dust mite allergens Der pI and Der PII (Chua et al. (1988) *J. Exp. Med.* 167:175-182; Chua et al. (1990) *Int. Arch. Allergy Appl. Immunol.* 91:124-129), domestic cat allergen Fel d I (Rogers et al. (1993) *Mol. Immunol.* 30:559-568), white birch pollen Bet vl (Breiteneder et al. (1989) *EMBO J.* 8:1935-1938), Japanese cedar allergens Cry j 1 and Cry j 2 (Kingetsu et al. (2000) *Immunology* 99:625-629), and protein antigens from other tree pollen (Elsayed et al. (1991) *Scand. J. Clin. Lab. Invest. Suppl.* 204:17-31). As indicated, allergens from trees are known, including allergens from birch, juniper and Japanese cedar. Preparation of Protein Antigens from Grass Pollen for In Vivo Administration has been Reported.

In some embodiments, the allergen is a food allergen, including, but not limited to, peanut allergen, for example Ara h I (Stanley et al. (1996) *Adv. Exp. Med. Biol.* 409:213-216); walnut allergen, for example, Jug r I (Tueber et al. (1998) *J. Allergy Clin. Immunol.* 101:807-814); brazil nut allergen, for example, albumin (Pastorello et al. (1998) *J. Allergy Clin. Immunol.* 102:1021-1027; shrimp allergen, for example, Pen a I (Reese et al. (1997) *Int. Arch. Allergy Immunol.* 113:240-242); egg allergen, for example, ovomucoid (Crooke et al. (1997) *J. Immunol.* 159:2026-2032); milk allergen, for example, bovine β-lactoglobin (Selot al. (1999) *Clin. Exp. Allergy* 29:1055-1063); fish allergen, for example, parvalbumins (Van Do et al. (1999) *Scand. J. Immunol.* 50:619-625; Galland et al. (1998) *J. Chromatogr. B. Biomed. Sci. Appl.* 706:63-71). In some embodiments, the allergen is a latex allergen, including but not limited to, Hev b 7 (Sowka et al. (1998) *Eur. J. Biochem.* 255:213-219). Table 1 shows an exemplary list of allergens that may be used.

TABLE 1

| RECOMBINANT ALLERGENS | | |
|---|---|---|
| Group | Allergen | Reference |
| ANIMALS: CRUSTACEA | | |
| Shrimp/lobster | tropomyosin | Leung et al. (1996) J. Allergy Clin. Immunol. 98: 954-961 |
|  | Pan s I | Leung et al. (1998) Mol. Mar. Biol. Biotechnol. 7: 12-20 |
| INSECTS | | |
| Ant | Sol i 2 (venom) | Schmidt et al. J Allergy Clin Immunol., 1996, 98: 82-8 |
| Bee | Phospholipase A2 (PLA) | Muller et al. J Allergy Clin Immunol, 1995, 96: 395-402 |
|  |  | Forster et al. J Allergy Clin Immunol, 1995, 95: 1229-35 |
|  |  | Muller et al. Clin Exp Allergy, 1997, 27: 915-20 |
|  | Hyaluronidase (Hya) | Soldatova et al. J Allergy Clin Immunol, 1998, 101: 691-8 |
| Cockroach | Bla g Bd9OK | Helm et al. J Allergy Clin Immunol, 1996, 98: 172-180 |
|  | Bla g 4 (a calycin) | Vailes et al. J Allergy Clin Immunol, 1998, 101: 274-280 |
|  | Glutathione S-transferase | Arruda et al. J Biol Chem, 1997, 272: 20907-12 |
|  | Per a 3 | Wu et al. Mol Immunol, 1997, 34: 1-8 |
| Dust mite | Der p 2 (major allergen) | Lynch et al. J Allergy Clin Immunol, 1998, 101: 562-4 |
|  |  | Hakkaart et al. Clin Exp Allergy, 1998, 28: 169-74 |
|  |  | Hakkaart et al. Clin Exp Allergy, 1998, 28: 45-52 |
|  |  | Hakkaart et al. Int Arch Allergy Immunol, 1998, 115 (2): 150-6 |
|  |  | Mueller et al. J Biol Chem, 1997, 272: 26893-8 |
|  | Der p2 variant | Smith et al. J Allergy Clin Immunol, 1998, 101: 423-5 |
|  | Der f2 | Yasue et al. Clin Exp Immunol, 1998, 113: 1-9 |
|  |  | Yasue et al. Cell Immunol, 1997, 181: 30-7 |
|  | Der p10 | Asturias et al. Biochim Biophys Acta, 1998, 1397: 27-30 |
|  | Tyr p 2 | Eriksson et al. Eur J Biochem, 1998 |
| Hornet | Antigen 5 aka Dol m V (venom) | Tomalski et al. Arch Insect Biochem Physiol, 1993, 22: 303-13 |
| Mosquito | Aed a I (salivary apyrase) | Xu et al. Int Arch Allergy Immunol, 1998, 115: 245-51 |
| Yellow jacket | antigen 5, hyaluronidase and phospholipase (venom) | King et al. J Allergy Clin Immunol, 1996, 98: 588-600 |
| MAMMALS | | |
| Cat | Fel d I | Slunt et al. J Allergy Clin Immunol, 1995, 95: 1221-8 |
|  |  | Hoffmann et al. (1997) J Allergy Clin Immunol 99: 227-32 |
|  |  | Hedlin Curr Opin Pediatr, 1995, 7: 676-82 |
| Cow | *Bos* d 2 (dander; a lipocalin) | Zeiler et al. J Allergy Clin Immunol, 1997, 100: 721-7 |
|  |  | Rautiainen et al. Biochem Bioph. Res Comm., 1998, 247: 746-50 |
|  | β-lactoglobulin (BLG, major cow milk allergen) | Chatel et al. Mol Immunol, 1996, 33: 1113-8 |
|  |  | Lehrer et al. Crit Rev Food Sci Nutr, 1996, 36: 553-64 |
| Dog | Can f I and Can f 2, salivary lipocalins | Konieczny et al. Immunology, 1997, 92: 577-86 |
|  |  | Spitzauer et al. J Allergy Clin Immunol, 1994, 93: 614-27 |
|  |  | Vrtala et al. J Immunol, 1998, 160: 6137-44 |
| Horse | Equ c1 (major allergen, a lipocalin) | Gregoire et al. J Biol Chem, 1996, 271: 32951-9 |
| Mouse | mouse urinary protein (MUP) | Konieczny et al. Immunology, 1997, 92: 577-86 |
| OTHER MAMMALIAN ALLERGENS | | |
| Insulin |  | Ganz et al. J Allergy Clin Immunol, 1990, 86: 45-51 |
|  |  | Grammer et al. J Lab Clin Med, 1987, 109: 141-6 |
|  |  | Gonzalo et al. Allergy, 1998, 53: 106-7 |
| Interferons | interferon alpha 2c | Detmar et al. Contact Dermatis, 1989, 20: 149-50 |
| MOLLUSCS | topomyosin | Leung et al. J Allergy Clin Immunol, 1996, 98: 954-61 |
| PLANT ALLERGENS: | | |
| Barley | Hor v 9 | Astwood et al. Adv Exp Med Biol, 1996, 409: 269-77 |

TABLE 1-continued

RECOMBINANT ALLERGENS

| Group | Allergen | Reference |
|---|---|---|
| Birch | pollen allergen, Bet v 4 | Twardosz et al. Biochem Bioph. Res Comm., 1997, 239: 197 |
|  | rBet v 1 Bet v 2: (profilin) | Pauli et al. J Allergy Clin Immunol, 1996, 97: 1100-9<br>van Neerven et al. Clin Exp Allergy, 1998, 28: 423-33<br>Jahn-Schmid et al. Immunotechnology, 1996, 2: 103-13<br>Breitwieser et al. Biotechniques, 1996, 21: 918-25<br>Fuchs et al. J Allergy Clin Immunol, 1997, 100: 356-64 |
| Brazil nut | globulin | Bartolome et al. Allergol Immunopathol, 1997, 25: 135-44 |
| Cherry | Pru a I (major allergen) | Scheurer et al. Mol Immunol, 1997, 34: 619-29 |
| Corn | Zml3 (pollen) | Heiss et al. FEBS Lett, 1996, 381: 217-21<br>Lehrer et al. Int Arch Allergy Immunol, 1997, 113: 122-4 |
| Grass | Phl p 1, Phl p 2, Phl p 5 (timothy grass pollen) | Bufe et al. Am J Respir Crit Care Med, 1998, 157: 1269-76<br>Vrtala et al. J Immunol Jun. 15, 1998, 160: 6137-44<br>Niederberger et al. J Allergy Clin Immun., 1998, 101: 258-64 |
|  | Hol 1 5 velvet grass pollen | Schramm et al. Eur J Biochem, 1998, 252: 200-6 |
|  | Bluegrass allergen | Zhang et al. J Immunol, 1993, 151: 791-9 |
|  | Cyn d 7 Bermuda grass | Smith et al. Int Arch Allergy Immunol, 1997, 114: 265-71 |
|  | Cyn d 12 (a profilin) | Asturias et al. Clin Exp Allergy, 1997, 27: 1307-13<br>Fuchs et al. J Allergy Clin Immunol, 1997, 100: 356-64 |
| Japanese Cedar | Jun a 2 (*Juniperus ashei*) | Yokoyama et al. Biochem. Biophys. Res. Commun., 2000, 275: 195-202 |
|  | Cry j 1, Cry j 2 (*Cryptomeria japonica*) | Kingetsu et al. Immunology, 2000, 99: 625-629 |
| Juniper | Jun o 2 (pollen) | Tinghino et al. J Allergy Clin Immunol, 1998, 101: 772-7 |
| Latex | Hev b 7 | Sowka et al. Eur J Biochem, 1998, 255: 213-9<br>Fuchs et al. J Allergy Clin Immunol, 1997, 100: 356-64 |
| *Mercurialis* | Mer a I (profilin) | Vallverdu et al. J Allergy Clin Immunol, 1998, 101: 363-70 |
| Mustard (Yellow) | Sin a I (seed) | Gonzalez de la Pena et al. Biochem Bioph. Res Comm., 1993, 190: 648-53 |
| Oilseed rape | Bra r I pollen allergen | Smith et al. Int Arch Allergy Immunol, 1997, 114: 265-71 |
| Peanut | Ara h I | Stanley et al. Adv Exp Med Biol, 1996, 409: 213-6<br>Burks et al. J Clin Invest, 1995, 96: 1715-21<br>Burks et al. Int Arch Allergy Immunol, 1995, 107: 248-50 |
| *Poa pratensis* | *Poa* p9 | Parronchi et al. Eur J Immunol, 1996, 26: 697-703<br>Astwood et al. Adv Exp Med Biol, 1996, 409: 269-77 |
| Ragweed | Amb a I | Sun et al. Biotechnology August 1995, 13: 779-86<br>Hirschwehr et al. J Allergy Clin Immunol, 1998, 101: 196-206<br>Casale et al. J Allergy Clin Immunol, 1997, 100: 110-21 |
| Rye | Lol p I | Tamborini et al. Eur J Biochem, 1997, 249: 886-94 |
| Walnut | Jug r I | Teuber et al. J Allergy Clin Immun., 1998, 101: 807-14 |
| Wheat | allergen | Fuchs et al. J Allergy Clin Immunol, 1997, 100: 356-64<br>Donovan et al. Electrophoresis, 1993, 14: 917-22 |
| FUNGI: | | |
| *Aspergillus* | Asp f 1, Asp f 2, Asp f3, Asp f 4, rAsp f 6 | Crameri et al. Mycoses, 1998, 41 Suppl 1: 56-60<br>Hemmann et al. Eur J Immunol, 1998, 28: 1155-60<br>Banerjee et al. J Allergy Clin Immunol, 1997, 99: 821-7<br>Crameri Int Arch Allergy Immunol, 1998, 115: 99-114<br>Crameri et al. Adv Exp Med Biol, 1996, 409: 111-6<br>Moser et al. J Allergy Clin Immunol, 1994, 93: 1-11 |
|  | Manganese superoxide dismutase (MNSOD) | Mayer et al. Int Arch Allergy Immunol, 1997, 113: 213-5 |
| *Blomia* | allergen | Caraballo et al. Adv Exp Med Biol, 1996, 409: 81-3 |
| *Penicillinium* | allergen | Shen et al. Clin Exp Allergy, 1997, 27: 682-90 |
| *Psilocybe* | Psi c 2 | Horner et al. Int Arch Allergy Immunol, 1995, 107: 298-300 |

In some embodiments, the antigen is from an infectious agent, including protozoan, bacterial, fungal (including unicellular and multicellular), and viral infectious agents. Examples of suitable viral antigens are described herein and are known in the art. Bacteria include *Hemophilus influenza*, *Mycobacterium tuberculosis* and *Bordetella pertussis*. Protozoan infectious agents include malarial plasmodia, *Leishmania* species, *Trypanosoma species* and *Schistosoma* species. Fungi include *Candida albicans*.

In some embodiments, the antigen is a viral antigen. Viral polypeptide antigens include, but are not limited to, HIV proteins such as HIV gag proteins (including, but not limited to, membrane anchoring (MA) protein, core capsid (CA) protein and nucleocapsid (NC) protein), HIV polymerase, influenza virus matrix (M) protein and influenza virus nucleocapsid (NP) protein, hepatitis B surface antigen (HBsAg), hepatitis B core protein (HBcAg), hepatitis e protein (HBeAg), hepatitis B DNA polymerase, hepatitis C antigens, and the like. References discussing influenza vaccination include Scherle and Gerhard (1988) *Proc. Natl. Acad. Sci. USA* 85:4446-4450; Scherle and Gerhard (1986) *J. Exp. Med.* 164:1114-1128; Granoff et al. (1993) *Vaccine* 11:S46-51; Kodihalli et al. (1997) *J. Virol.* 71:3391-3396; Ahmeida et al. (1993) *Vaccine* 11:1302-1309; Chen et al. (1999) *Vaccine* 17:653-659; Govorkova and Smirnov (1997) *Acta Virol.* (1997) 41:251-257; Koide et al. (1995) *Vaccine* 13:3-5; Mbawuike et al. (1994) *Vaccine* 12:1340-1348; Tamura et al. (1994) *Vaccine* 12:310-316; Tamura et al. (1992) *Eur. J. Immunol.* 22:477-481; Hirabayashi et al. (1990) *Vaccine* 8:595-599. Other examples of antigen polypeptides are group- or sub-group specific antigens, which are known for a number of infectious agents, including, but not limited to, adenovirus, herpes simplex virus, papilloma virus, respiratory syncytial virus and poxviruses.

As shown in Example 3 below, administration of ISS-containing polynucleotides in conjunction with a hepatitis virus antigen, hepatitis B surface antigen (HBsAg), resulted in increased titers of anti-HBsAg antibodies in primates as compared to administration of HBsAg alone.

Many antigenic peptides and proteins are known, and available in the art; others can be identified using conventional techniques. For immunization against tumor formation or treatment of existing tumors, immunomodulatory peptides can include tumor cells (live or irradiated), tumor cell extracts, or protein subunits of tumor antigens such as Her-2/neu, Mart1, carcinoembryonic antigen (CEA), gangliosides, human milk fat globule (HMFG), mucin (MUC1), MAGE antigens, BAGE antigens, GAGE antigens, gp100, prostate specific antigen (PSA), and tyrosinase. Vaccines for immuno-based contraception can be formed by including sperm proteins administered with ISS. Lea et al. (1996) *Biochim. Biophys. Acta* 1307:263.

Attenuated and inactivated viruses are suitable for use herein as the antigen. Preparation of these Viruses is Well-Known in the Art and Many are Commercially Available (See, e.g., Physicians' Desk Reference (1998) 52nd edition, Medical Economics Company, Inc.). For example, polio virus is available as IPOL® (Pasteur Merieux Connaught) and ORIMUNE® (Lederle Laboratories), hepatitis A virus as VAQTA® (Merck), measles virus as ATTENUVAX® (Merck), mumps virus as MUMPSVAX® (Merck) and rubella virus as MERUVAX®II (Merck). Additionally, attenuated and inactivated viruses such as HIV-1, HIV-2, herpes simplex virus, hepatitis B virus, rotavirus, human and non-human papillomavirus and slow brain viruses can provide peptide antigens.

In some embodiments, the antigen comprises a viral vector, such as vaccinia, adenovirus, and canary pox.

Antigens may be isolated from their source using purification techniques known in the art or, more conveniently, may be produced using recombinant methods.

Antigenic peptides can include purified native peptides, synthetic peptides, recombinant proteins, crude protein extracts, attenuated or inactivated viruses, cells, micro-organisms, or fragments of such peptides. Immunomodulatory peptides can be native or synthesized chemically or enzymatically. Any method of chemical synthesis known in the art is suitable. Solution phase peptide synthesis can be used to construct peptides of moderate size or, for the chemical construction of peptides, solid phase synthesis can be employed. Atherton et al. (1981) *Hoppe Seylers Z. Physiol. Chem.* 362: 833-839. Proteolytic enzymes can also be utilized to couple amino acids to produce peptides. Kullmann (1987) Enzymatic Peptide Synthesis, CRC Press, Inc. Alternatively, the peptide can be obtained by using the biochemical machinery of a cell, or by isolation from a biological source. Recombinant DNA techniques can be employed for the production of peptides. Hames et al. (1987) Transcription and Translation: A Practical Approach, IRL Press. Peptides can also be isolated using standard techniques such as affinity chromatography.

Preferably the antigens are peptides, lipids (e.g., sterols excluding cholesterol, fatty acids, and phospholipids), polysaccharides such as those used in *H. influenza* vaccines, gangliosides and glycoproteins. These can be obtained through several methods known in the art, including isolation and synthesis using chemical and enzymatic methods. In certain cases, such as for many sterols, fatty acids and phospholipids, the antigenic portions of the molecules are commercially available.

Examples of viral antigens useful in the subject compositions and methods using the compositions include, but are not limited to, HIV antigens. Such antigens include, but are not limited to, those antigens derived from HIV envelope glycoproteins including, but not limited to, gp160, gp120 and gp41. Numerous sequences for HIV genes and antigens are known. For example, the Los Alamos National Laboratory HIV Sequence Database collects, curates and annotates HIV nucleotide and amino acid sequences. This database is accessible via the internet, at http://hiv-web.lanl.gov/, and in a yearly publication, see Human Retroviruses and AIDS Compendium (for example, 2000 edition).

Antigens derived from infectious agents may be obtained using methods known in the art, for example, from native viral or bacterial extracts, from cells infected with the infectious agent, from purified polypeptides, from recombinantly produced polypeptides and/or as synthetic peptides.

ISS-Antigen

When used with antigen, ISS may be administered with antigen in a number of ways. In some embodiments, an ISS-containing polynucleotide and antigen may be administered spatially proximate with respect to each other, or as an admixture (i.e., in solution). As described below, spatial proximation can be accomplished in a number of ways, including conjugation (linkage), encapsidation, via affixation to a platform or adsorption onto a surface. Generally, and most preferably, an ISS-containing polynucleotide and antigen are proximately associated at a distance effective to enhance the immune response generated compared to the administration of the ISS and the antigen as an admixture.

In some embodiments, the ISS-containing polynucleotide is conjugated with the antigen. The ISS portion can be coupled with the antigen portion of a conjugate in a variety of ways, including covalent and/or non-covalent interactions.

The link between the portions can be made at the 3' or 5' end of the ISS, or at a suitably modified base at an internal position in the ISS. If the antigen is a peptide and contains a suitable reactive group (e.g., an N-hydroxysuccinimide ester) it can be reacted directly with the $N^4$ amino group of cytosine residues. Depending on the number and location of cytosine residues in the ISS, specific coupling at one or more residues can be achieved.

Alternatively, modified oligonucleosides, such as are known in the art, can be incorporated at either terminus, or at internal positions in the ISS. These can contain blocked functional groups which, when deblocked, are reactive with a variety of functional groups which can be present on, or attached to, the antigen of interest.

Where the antigen is a peptide or polypeptide, this portion of the conjugate can be attached to the 3'-end of the ISS through solid support chemistry. For example, the ISS portion can be added to a polypeptide portion that has been pre-synthesized on a support. Haralambidis et al. (1990a) *Nucleic Acids Res.* 18:493-499; and Haralambidis et al. (1990b) *Nucleic Acids Res.* 18:501-505. Alternatively, the ISS can be synthesized such that it is connected to a solid support through a cleavable linker extending from the 3'-end. Upon chemical cleavage of the ISS from the support, a terminal thiol group is left at the 3'-end of the oligonucleotide (Zuckermann et al. (1987) *Nucleic Acids Res.* 15:5305-5321; and Corey et al. (1987) *Science* 238:1401-1403) or a terminal amino group is left at the 3'-end of the oligonucleotide (Nelson et al. (1989) *Nucleic Acids Res.* 17:1781-1794). Conjugation of the amino-modified ISS to amino groups of the peptide can be performed as described in Benoit et al. (1987) *Neuromethods* 6:43-72. Conjugation of the thiol-modified ISS to carboxyl groups of the peptide can be performed as described in Sinah et al. (1991) *Oligonucleotide Analogues: A Practical Approach*, IRL Press. Coupling of an oligonucleotide carrying an appended maleimide to the thiol side chain of a cysteine residue of a peptide has also been described. Tung et al. (1991) *Bioconjug. Chem.* 2:464-465.

The peptide or polypeptide portion of the conjugate can be attached to the 5'-end of the ISS through an amine, thiol, or carboxyl group that has been incorporated into the oligonucleotide during its synthesis. Preferably, while the oligonucleotide is fixed to the solid support, a linking group comprising a protected amine, thiol, or carboxyl at one end, and a phosphoramidite at the other, is covalently attached to the 5'-hydroxyl. Agrawal et al. (1986) *Nucleic Acids Res.* 14:6227-6245; Connolly (1985) *Nucleic Acids Res.* 13:4485-4502; Kremsky et al. (1987) *Nucleic Acids Res.* 15:2891-2909; Connolly (1987) *Nucleic Acids Res.* 15:3131-3139; Bischoff et al. (1987) *Anal. Biochem.* 164:336-344; Blanks et al. (1988) *Nucleic Acids Res.* 16:10283-10299; and U.S. Pat. Nos. 4,849,513, 5,015,733, 5,118,800, and 5,118,802. Subsequent to deprotection, the amine, thiol, and carboxyl functionalities can be used to covalently attach the oligonucleotide to a peptide. Benoit et al. (1987); and Sinah et al. (1991).

An ISS-antigen conjugate can also be formed through non-covalent interactions, such as ionic bonds, hydrophobic interactions, hydrogen bonds and/or van der Waals attractions.

Non-covalently linked conjugates can include a non-covalent interaction such as a biotin-streptavidin complex. A biotinyl group can be attached, for example, to a modified base of an ISS. Roget et al. (1989) *Nucleic Acids Res.* 17:7643-7651. Incorporation of a streptavidin moiety into the peptide portion allows formation of a non-covalently bound complex of the streptavidin conjugated peptide and the biotinylated oligonucleotide.

Non-covalent associations can also occur through ionic interactions involving an ISS and residues within the antigen, such as charged amino acids, or through the use of a linker portion comprising charged residues that can interact with both the oligonucleotide and the antigen. For example, non-covalent conjugation can occur between a generally negatively-charged ISS and positively-charged amino acid residues of a peptide, e.g., polylysine, polyarginine and polyhistidine residues.

Non-covalent conjugation between ISS and antigens can occur through DNA binding motifs of molecules that interact with DNA as their natural ligands. For example, such DNA binding motifs can be found in transcription factors and anti-DNA antibodies.

The linkage of the ISS to a lipid can be formed using standard methods. These methods include, but are not limited to, the synthesis of oligonucleotide-phospholipid conjugates (Yanagawa et al. (1988) *Nucleic Acids Symp. Ser.* 19:189-192), oligonucleotide-fatty acid conjugates (Grabarek et al. (1990) *Anal. Biochem.* 185:131-135; and Staros et al. (1986) *Anal. Biochem.* 156:220-222), and oligonucleotide-sterol conjugates. Boujrad et al. (1993) *Proc. Natl. Acad. Sci. USA* 90:5728-5731.

The linkage of the oligonucleotide to an oligosaccharide can be formed using standard known methods. These methods include, but are not limited to, the synthesis of oligonucleotide-oligosaccharide conjugates, wherein the oligosaccharide is a moiety of an immunoglobulin. O'Shannessy et al. (1985) *J. Applied Biochem.* 7:347-355.

The linkage of a circular ISS to a peptide or antigen can be formed in several ways. Where the circular ISS is synthesized using recombinant or chemical methods, a modified nucleoside is suitable. Ruth (1991) in *Oligonucleotides and Analogues: A Practical Approach*, IRL Press. Standard linking technology can then be used to connect the circular ISS to the antigen or other peptide. Goodchild (1990) *Bioconjug. Chem.* 1:165. Where the circular ISS is isolated, or synthesized using recombinant or chemical methods, the linkage can be formed by chemically activating, or photoactivating, a reactive group (e.g. carbene, radical) that has been incorporated into the antigen or other peptide.

Additional methods for the attachment of peptides and other molecules to oligonucleotides can be found in U.S. Pat. No. 5,391,723; Kessler (1992) "Nonradioactive labeling methods for nucleic acids" in Kricka (ed.) *Nonisotopic DNA Probe Techniques*, Academic Press; and Geoghegan et al. (1992) *Bioconjug. Chem.* 3:138-146.

An ISS may be proximately associated with an antigen(s) in other ways. In some embodiments, an ISS and antigen are proximately associated by encapsulation. In other embodiments, an ISS and antigen are proximately associated by linkage to a platform molecule. A "platform molecule" (also termed "platform") is a molecule containing sites which allow for attachment of the ISS and antigen(s). In other embodiments, an ISS and antigen are proximately associated by adsorption onto a surface, preferably a carrier particle.

In some embodiments, the methods of the invention employ an encapsulating agent that can maintain the proximate association of the ISS and first antigen until the complex is available to the target (or compositions comprising such encapsulating agents). Preferably, the composition comprising ISS, antigen and encapsulating agent is in the form of adjuvant oil-in-water emulsions, microparticles and/or liposomes. More preferably, adjuvant oil-in-water emulsions, microparticles and/or liposomes encapsulating an ISS-immunomodulatory molecule are in the form of particles from about 0.04 µm to about 100 µm in size, preferably any of the following ranges: from about 0.1 µm to about 20 µm; from about 0.15 µm to about 10 µm; from about 0.05 µm to about 1.00 µm; from about 0.05 µm to about 0.5 µm.

Colloidal dispersion systems, such as microspheres, beads, macromolecular complexes, nanocapsules and lipid-based system, such as oil-in-water emulsions, micelles, mixed micelles and liposomes can provide effective encapsulation of ISS-containing compositions.

The encapsulation composition further comprises any of a wide variety of components. These include, but are not limited to, alum, lipids, phospholipids, lipid membrane structures (LMS), polyethylene glycol (PEG) and other polymers, such as polypeptides, glycopeptides, and polysaccharides.

Polypeptides suitable for encapsulation components include any known in the art and include, but are not limited to, fatty acid binding proteins. Modified polypeptides contain any of a variety of modifications, including, but not limited to glycosylation, phosphorylation, myristylation, sulfation and hydroxylation. As used herein, a suitable polypeptide is one that will protect an ISS-containing composition to preserve the immunomodulatory activity thereof. Examples of binding proteins include, but are not limited to, albumins such as bovine serum albumin (BSA) and pea albumin.

Other suitable polymers can be any known in the art of pharmaceuticals and include, but are not limited to, naturally-occurring polymers such as dextrans, hydroxyethyl starch, and polysaccharides, and synthetic polymers. Examples of naturally occurring polymers include proteins, glycopeptides, polysaccharides, dextran and lipids. The additional polymer can be a synthetic polymer. Examples of synthetic polymers which are suitable for use in the present invention include, but are not limited to, polyalkyl glycols (PAG) such as PEG, polyoxyethylated polyols (POP), such as polyoxyethylated glycerol (POG), polytrimethylene glycol (PTG) polypropylene glycol (PPG), polyhydroxyethyl methacrylate, polyvinyl alcohol (PVA), polyacrylic acid, polyethyloxazoline, polyacrylamide, polyvinylpyrrolidone (PVP), polyamino acids, polyurethane and polyphosphazene. The synthetic polymers can also be linear or branched, substituted or unsubstituted, homopolymeric, co-polymers, or block co-polymers of two or more different synthetic monomers.

The PEGs for use in encapsulation compositions of the present invention are either purchased from chemical suppliers or synthesized using techniques known to those of skill in the art.

The term "LMS", as used herein, means lamellar lipid particles wherein polar head groups of a polar lipid are arranged to face an aqueous phase of an interface to form membrane structures. Examples of the LMSs include liposomes, micelles, cochleates (i.e., generally cylindrical liposomes), microemulsions, unilamellar vesicles, multilamellar vesicles, and the like.

A preferred colloidal dispersion system of this invention is a liposome. In mice immunized with a liposome-encapsulated antigen, liposomes appeared to enhance a Th1-type immune response to the antigen. Aramaki et al. (1995) *Vaccine* 13:1809-1814. As used herein, a "liposome" or "lipid vesicle" is a small vesicle bounded by at least one and possibly more than one bilayer lipid membrane. Liposomes are made artificially from phospholipids, glycolipids, lipids, steroids such as cholesterol, related molecules, or a combination thereof by any technique known in the art, including but not limited to sonication, extrusion, or removal of detergent from lipid-detergent complexes. A liposome can also optionally comprise additional components, such as a tissue targeting component. It is understood that a "lipid membrane" or "lipid bilayer" need not consist exclusively of lipids, but can additionally contain any suitable other components, including, but not limited to, cholesterol and other steroids, lipid-soluble chemicals, proteins of any length, and other amphipathic molecules, providing the general structure of the membrane is a sheet of two hydrophilic surfaces sandwiching a hydrophobic core. For a general discussion of membrane structure, see *The Encyclopedia of Molecular Biology* by J. Kendrew (1994). For suitable lipids see e.g., Lasic (1993) "Liposomes: from Physics to Applications" Elsevier, Amsterdam.

Processes for preparing liposomes containing ISS-containing compositions are known in the art. The lipid vesicles can be prepared by any suitable technique known in the art. Methods include, but are not limited to, microencapsulation, microfluidization, LLC method, ethanol injection, freon injection, the "bubble" method, detergent dialysis, hydration, sonication, and reverse-phase evaporation. Reviewed in Watwe et al. (1995) *Curr. Sci.* 68:715-724. Techniques may be combined in order to provide vesicles with the most desirable attributes.

The invention encompasses use of LMSs containing tissue or cellular targeting components. Such targeting components are components of a LMS that enhance its accumulation at certain tissue or cellular sites in preference to other tissue or cellular sites when administered to an intact animal, organ, or cell culture. A targeting component is generally accessible from outside the liposome, and is therefore preferably either bound to the outer surface or inserted into the outer lipid bilayer. A targeting component can be inter alia a peptide, a region of a larger peptide, an antibody specific for a cell surface molecule or marker, or antigen binding fragment thereof, a nucleic acid, a carbohydrate, a region of a complex carbohydrate, a special lipid, or a small molecule such as a drug, hormone, or hapten, attached to any of the aforementioned molecules. Antibodies with specificity toward cell type-specific cell surface markers are known in the art and are readily prepared by methods known in the art.

The LMSs can be targeted to any cell type toward which a therapeutic treatment is to be directed, e.g., a cell type which can modulate and/or participate in an immune response. Such target cells and organs include, but are not limited to, APCs, such as macrophages, dendritic cells and lymphocytes, lymphatic structures, such as lymph nodes and the spleen, and nonlymphatic structures, particularly those in which dendritic cells are found.

The LMS compositions of the present invention can additionally comprise surfactants. Surfactants can be cationic, anionic, amphiphilic, or nonionic. A preferred class of surfactants are nonionic surfactants; particularly preferred are those that are water soluble.

In embodiments in which an ISS and antigen are proximately associated by linkage to a platform molecule, the platform may be proteinaceous or non-proteinaceous (i.e., organic). Examples of proteinaceous platforms include, but are not limited to, albumin, gammaglobulin, immunoglobulin (IgG) and ovalbumin. Borel et al. (1990) *Immunol. Methods* 126:159-168; Dumas et al. (1995) *Arch. Dematol. Res.* 287: 123-128; Borel et al. (1995) *Int. Arch. Allergy Immunol.* 107: 264-267; Borel et al. (1996) *Ann. N.Y. Acad. Sci.* 778:80-87. A platform is multi-valent (i.e., contains more than one binding, or linking, site) to accommodate binding to both an ISS and antigen. Other examples of polymeric platforms are dextran, polyacrylamide, ficoll, carboxymethylcellulose, polyvinyl alcohol, and poly D-glutamic acid/D-lysine.

The principles of using platform molecules are well understood in the art. Generally, a platform contains, or is derivatized to contain, appropriate binding sites for ISS and antigen. In addition, or alternatively, ISS and/or antigen is derivatized to provide appropriate linkage groups. For example, a simple platform is a bi-functional linker (i.e., has two binding sites), such as a peptide. Further examples are discussed below.

Platform molecules may be biologically stabilized, i.e., they exhibit an in vivo excretion half-life often of hours to days to months to confer therapeutic efficacy, and are preferably composed of a synthetic single chain of defined composition. They generally have a molecular weight in the range of about 200 to about 1,000,000, preferably any of the following ranges: from about 200 to about 500,000; from about 200 to about 200,000; from about 200 to about 50,000 (or less, such as 30,000). Examples of valency platform molecules are polymers (or are comprised of polymers) such as polyethylene glycol (PEG; preferably having a molecular weight of about 200 to about 8000), poly-D-lysine, polyvinyl alcohol, polyvinylpyrrolidone, D-glutamic acid and D-lysine (in a ratio of 3:2). Other molecules that may be used are albumin and IgG.

Other platform molecules suitable for use within the present invention are the chemically-defined, non-polymeric valency platform molecules disclosed in U.S. Pat. No. 5,552, 391. Other homogeneous chemically-defined valency platform molecules suitable for use within the present invention are derivatized 2,2'-ethylenedioxydiethylamine (EDDA) and triethylene glycol (TEG).

Additional suitable valency platform molecules include, but are not limited to, tetraminobenzene, heptaminobetacyclodextrin, tetraminopentaerythritol, 1,4,8,11-tetraazacyclotetradecane (Cyclam) and 1,4,7,10-tetraazacyclododecane (Cyclen).

In general, these platforms are made by standard chemical synthesis techniques. PEG must be derivatized and made multivalent, which is accomplished using standard techniques. Some substances suitable for conjugate synthesis, such as PEG, albumin, and IgG are available commercially.

Conjugation of an ISS and antigen to a platform molecule may be effected in any number of ways, typically involving one or more crosslinking agents and functional groups on the antigen and ISS platform and platform molecule. Platforms and ISS and antigen must have appropriate linking groups. Linking groups are added to platforms using standard synthetic chemistry techniques. Linking groups may be added to polypeptide antigens and ISS using either standard solid phase synthetic techniques or recombinant techniques. Recombinant approaches may require post-translational modification in order to attach a linker, and such methods are known in the art.

As an example, polypeptides contain amino acid side chain moieties containing functional groups such as amino, carboxyl or sulfhydryl groups that serve as sites for coupling the polypeptide to the platform. Residues that have such functional groups may be added to the polypeptide if the polypeptide does not already contain these groups. Such residues may be incorporated by solid phase synthesis techniques or recombinant techniques, both of which are well known in the peptide synthesis arts. When the polypeptide has a carbohydrate side chain(s) (or if the antigen is a carbohydrate), functional amino, sulfhydryl and/or aldehyde groups may be incorporated therein by conventional chemistry. For instance, primary amino groups may be incorporated by reaction of the oxidized sugar with ethylenediamine in the presence of sodium cyanoborohydride, sulfhydryls may be introduced by reaction of cysteamine dihydrochloride followed by reduction with a standard disulfide reducing agent, while aldehyde groups may be generated following periodate oxidation. In a similar fashion, the platform molecule may also be derivatized to contain functional groups if it does not already possess appropriate functional groups.

Hydrophilic linkers of variable lengths are useful for connecting ISS and antigen to platform molecules. Suitable linkers include linear oligomers or polymers of ethylene glycol. Such linkers include linkers with the formula $R^1S(CH_2CH_2O)_nCH_2CH_2$—O—$(CH_2)_mCO_2R^2$ wherein n=0-200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloaceyl, maleiamide, etc., via a thioether to a second molecule which contains an amino group via an amide bond. These linkers are flexible with regard to the order of attachment, i.e., the thioether can be formed first or last.

In embodiments in which an ISS and antigen are proximately associated by adsorption onto a surface, the surface may be in the form of a carrier particle (for example, a nanoparticle) made with either an inorganic or organic core. Examples of such nanoparticles include, but are not limited to, nanocrystalline particles, nanoparticles made by the polymerization of alkylcyanoacrylates and nanoparticles made by the polymerization of methylidene malonate. Additional surfaces to which an ISS and antigen may be adsorbed include, but are not limited to, activated carbon particles and protein-ceramic nanoplates. Other examples of carrier particles are provided herein.

Adsorption of polynucleotides and polypeptides to a surface for the purpose of delivery of the adsorbed molecules to cells is well known in the art. See, for example, Douglas et al. (1987) *Crit. Rev. Ther. Drug. Carrier Syst.* 3:233-261; Hagiwara et al. (1987) *In Vivo* 1:241-252; Bousquet et al. (1999) *Pharm. Res.* 16:141-147; and Kossovsky et al., U.S. Pat. No. 5,460,831. Preferably, the material comprising the adsorbent surface is biodegradable. Adsorption of an ISS and/or antigen to a surface may occur through non-covalent interactions, including ionic and/or hydrophobic interactions.

In general, characteristics of carriers such as nanoparticles, such as surface charge, particle size and molecular weight, depend upon polymerization conditions, monomer concentration and the presence of stabilizers during the polymerization process (Douglas et al., 1987). The surface of carrier particles may be modified, for example, with a surface coating, to allow or enhance adsorption of the ISS and/or antigen. Carrier particles with adsorbed ISS and/or antigen may be further coated with other substances. The addition of such other substances may, for example, prolong the half-life of the particles once administered to the subject and/or may target the particles to a specific cell type or tissue, as described herein.

Nanocrystalline surfaces to which an ISS and antigen may be adsorbed have been described (see, for example, U.S. Pat. No. 5,460,831). Nanocrystalline core particles (with diameters of 1 μm or less) are coated with a surface energy modifying layer that promotes adsorption of polypeptides, polynucleotides and/or other pharmaceutical agents. As described in U.S. Pat. No. 5,460,831, for example, a core particle is coated with a surface that promotes adsorption of an oligonucleotide and is subsequently coated with an antigen preparation, for example, in the form of a lipid-antigen mixture. Such nanoparticles are self-assembling complexes of nanometer sized particles, typically on the order of 0.1 μm, that carry an inner layer of ISS and an outer layer of antigen.

Another adsorbent surface are nanoparticles made by the polymerization of alkylcyanoacrylates. Alkylcyanoacrylates can be polymerized in acidified aqueous media by a process of anionic polymerization. Depending on the polymerization conditions, the small particles tend to have sizes in the range of 20 to 3000 nm, and it is possible to make nanoparticles specific surface characteristics and with specific surface charges (Douglas et al., 1987). For example, oligonucleotides may be adsorbed to polyisobutyl- and polyisohexlcyanoacrylate nanoparticles in the presence of hydrophobic cations such as tetraphenylphosphonium chloride or quaternary ammonium salts, such as cetyltrimethyl ammonium bromide. Oligonucleotide adsorption on these nanoparticles appears to be mediated by the formation of ion pairs between negatively charged phosphate groups of the nucleic acid chain and the hydrophobic cations. See, for example, Lambert et al. (1998) *Biochimie* 80:969-976, Chavany et al. (1994) *Pharm. Res.* 11:1370-1378; Chavany et al. (1992) *Pharm. Res.* 9:441-449. Polypeptides may also be adsorbed to polyalkylcyanoacrylate nanoparticles. See, for example, Douglas et al., 1987; Schroeder et al. (1998) *Peptides* 19:777-780.

Another adsorbent surface are nanoparticles made by the polymerization of methylidene malonate. For example, as described in Bousquet et al., 1999, polypeptides adsorbed to poly(methylidene malonate 2.1.2) nanoparticles appear to do so initially through electrostatic forces followed by stabilization through hydrophobic forces.

IMP/MC Complexes

ISS-containing polynucleotides may be administered in the form of immunomodulatory polynucleotide/microcarrier (IMP/MC) complexes. Accordingly, the invention provides compositions comprising IMP/MC complexes.

Microcarriers useful in the invention are less than about 150, 120 or 100 μm in size, more commonly less than about 50-60 μm in size, preferably less than about 10 μm in size, and are insoluble in pure water. Microcarriers used in the invention are preferably biodegradable, although nonbiodegradable microcarriers are acceptable. Microcarriers are commonly solid phase, such as "beads" or other particles, although liquid phase microcarriers such as oil in water emulsions comprising a biodegradable polymers or oils are also contemplated. A wide variety of biodegradable and nonbiodegradable materials acceptable for use as microcarriers are known in the art.

Microcarriers for use in the compositions or methods of the invention are generally less than about 10 µm in size (e.g., have an average diameter of less than about 10 µm, or at least about 97% of the particles pass through a 10 µm screen filter), and include nanocarriers (i.e., carriers of less than about 1 µm size). Preferably, microcarriers are selected having sizes within an upper limit of about 9, 7, 5, 2, or 1 µm or 900, 800, 700, 600, 500, 400, 300, 250, 200, or 100 nm and an independently selected lower limit of about 4, 2, or 1 µm or about 800, 600, 500, 400, 300, 250, 200, 150, 100, 50, 25, or 10 nm, where the lower limit is less than the upper limit. In some embodiments, the microcarriers have a size of about 1.0-1.5 µm, about 1.0-2.0 µm or about 0.9-1.6 µm. In certain preferred embodiments, the microcarriers have a size of about 10 nm to about 5 µm or about 25 nm to about 4.5 µm, about 1 µm, about 1.2 µm, about 1.4 µm, about 1.5 µm, about 1.6 µm, about 1.8 µm, about 2.0 µm, about 2.5 µm or about 4.5 µm. When the microcarriers are nanocarriers, preferred embodiments include nanocarriers of about 25 to about 300 nm, 50 to about 200 nm, about 50 nm or about 200 nm.

Solid phase biodegradable microcarriers may be manufactured from biodegradable polymers including, but not limited to: biodegradable polyesters, such as poly(lactic acid), poly(glycolic acid), and copolymers (including block copolymers) thereof, as well as block copolymers of poly(lactic acid) and poly(ethylene glycol); polyorthoesters such as polymers based on 3,9-diethylidene-2,4,8,10-tetraoxaspiro [5.5]undecane (DETOSU); polyanhydrides such as poly(anhydride) polymers based on relatively hydrophilic monomers such as sebacic acid; polyanhydride imides, such as polyanhydride polymers based on sebacic acid-derived monomers incorporating amino acids (i.e., linked to sebacic acid by imide bonds through the amino-terminal nitrogen) such as glycine or alanine; polyanhydride esters; polyphosphazenes, especially poly(phosphazenes) which contain hydrolysis-sensitive ester groups which can catalyze degradation of the polymer backbone through generation of carboxylic acid groups (Schacht et al., (1996) *Biotechnol. Bioeng.* 1996:102); and polyamides such as poly(lactic acid-co-lysine).

A wide variety of nonbiodegradable materials suitable for manufacturing microcarriers are also known, including, but not limited to polystyrene, polypropylene, polyethylene, latex, gold, and ferromagnetic or paramagnetic materials. Certain embodiments exclude gold, latex, and/or magnetic beads. In certain embodiments, the microcarriers may be made of a first material (e.g., a magnetic material) encapsulated with a second material (e.g., polystyrene).

Solid phase microspheres are prepared using techniques known in the art. For example, they can be prepared by emulsion-solvent extraction/evaporation technique. Generally, in this technique, biodegradable polymers such as polyanhydrates, poly(alkyl-α-cyanoacrylates) and poly(α-hydroxy esters), for example, poly(lactic acid), poly(glycolic acid), poly(D,L-lactic-co-glycolic acid) and poly(caprolactone), are dissolved in a suitable organic solvent, such as methylene chloride, to constitute the dispersed phase (DP) of emulsion. DP is emulsified by high-speed homogenization into excess volume of aqueous continuous phase (CP) that contains a dissolved surfactant, for example, polyvinylalcohol (PVA) or polyvinylpirrolidone (PVP). Surfactant in CP is to ensure the formation of discrete and suitably-sized emulsion droplet. The organic solvent is then extracted into the CP and subsequently evaporated by raising the system temperature. The solid microparticles are then separated by centrifugation or filtration, and dried, for example, by lyophilization or application of vacuum, before storing at 4° C.

Physico-chemical characteristics such as mean size, size distribution and surface charge of dried microspheres may be determined. Size characteristics are determined, for example, by dynamic light scattering technique and the surface charge was determined by measuring the zeta potential.

Liquid phase microcarriers include liposomes, micelles, oil droplets and other lipid or oil-based particles which incorporate biodegradable polymers or oils. In certain embodiments, the biodegradable polymer is a surfactant. In other embodiments, the liquid phase microcarriers are biodegradable due to the inclusion of a biodegradable oil such as squalene or a vegetable oil. One preferred liquid phase microcarrier is oil droplets within an oil-in-water emulsion. Preferably, oil-in-water emulsions used as microcarriers comprise biodegradable substituents such as squalene.

IMP/MC complexes comprise an IMP bound to the surface of a microcarrier (i.e., the IMP is not encapsulated in the MC), and preferably comprise multiple molecules of IMP bound to each microcarrier. In certain embodiments, a mixture of different IMPs may be complexed with a microcarrier, such that the microcarrier is bound to more than one IMP species. The bond between the IMP and MC may be covalent or non-covalent. As will be understood by one of skill in the art, the IMP may be modified or derivatized and the composition of the microcarrier may be selected and/or modified to accommodate the desired type of binding desired for IMP/MC complex formation.

Covalently bonded IMP/MC complexes may be linked using any covalent crosslinking technology known in the art. Typically, the IMP portion will be modified, either to incorporate an additional moiety (e.g., a free amine, carboxyl or sulfhydryl group) or incorporate modified (e.g., phosphorothioate) nucleotide bases to provide a site at which the IMP portion may be linked to the microcarrier. The link between the IMP and MC portions of the complex can be made at the 3' or 5' end of the IMP, or at a suitably modified base at an internal position in the IMP. The microcarrier is generally also modified to incorporate moieties through which a covalent link may be formed, although functional groups normally present on the microcarrier may also be utilized. The IMP/MC is formed by incubating the IMP with a microcarrier under conditions which permit the formation of a covalent complex (e.g., in the presence of a crosslinking agent or by use of an activated microcarrier comprising an activated moiety which will form a covalent bond with the IMP).

A wide variety of crosslinking technologies are known in the art, and include crosslinkers reactive with amino, carboxyl and sulfhydryl groups. As will be apparent to one of skill in the art, the selection of a crosslinking agent and crosslinking protocol will depend on the configuration of the IMP and the microcarrier as well as the desired final configuration of the IMP/MC complex. The crosslinker may be either homobifunctional or heterobifunctional. When a homobifunctional crosslinker is used, the crosslinker exploits the same moiety on the IMP and MC (e.g., an aldehyde crosslinker may be used to covalently link an IMP and MC where both the IMP and MC comprise one or more free amines). Heterobifunctional crosslinkers utilize different moieties on the IMP and MC, (e.g., a maleimido-N-hydroxysuccinimide ester may be used to covalently link a free sulfhydryl on the IMP and a free amine on the MC), and are preferred to minimize formation of inter-microcarrier bonds. In most cases, it is preferable to crosslink through a first crosslinking moiety on the microcarrier and a second crosslinking moiety on the IMP, where the second crosslinking moiety is not present on the microcarrier. One preferred method of producing the IMP/MC complex is by 'activating' the microcarrier by incubating with a heterobifunctional crosslinking agent, then forming the IMP/MC complex by incubating the IMP and activated MC under conditions appropriate for reaction. The crosslinker may incorporate a "spacer" arm between the reactive moieties, or the two reactive moieties in the crosslinker may be directly linked.

In one preferred embodiment, the IMP portion comprises at least one free sulfhydryl (e.g., provided by a 5'-thiol modified base or linker) for crosslinking to the microcarrier, while the microcarrier comprises free amine groups. A heterobifunctional crosslinker reactive with these two groups (e.g., a crosslinker comprising a maleimide group and a NHS-ester), such as succinimidyl 4-(N-maleimidomethyl)cyclohexane-1-carboxylate is used to activate the MC, then covalently crosslink the IMP to form the IMP/MC complex.

Non-covalent IMP/MC complexes may be linked by any non-covalent binding or interaction, including ionic (electrostatic) bonds, hydrophobic interactions, hydrogen bonds, van der Waals attractions, or a combination of two or more different interactions, as is normally the case when a binding pair is to link the IMP and MC.

Preferred non-covalent IMP/MC complexes are typically complexed by hydrophobic or electrostatic (ionic) interactions, or a combination thereof, (e.g., through base pairing between an IMP and a polynucleotide bound to an MC use of a binding pair). Due to the hydrophilic nature of the backbone of polynucleotides, IMP/MC complexes which rely on hydrophobic interactions to form the complex generally require modification of the IMP portion of the complex to incorporate a highly hydrophobic moiety. Preferably, the hydrophobic moiety is biocompatible, nonimmunogenic, and is naturally occurring in the individual for whom the composition is intended (e.g., is found in mammals, particularly humans). Examples of preferred hydrophobic moieties include lipids, steroids, sterols such as cholesterol, and terpenes. The method of linking the hydrophobic moiety to the IMP will, of course, depend on the configuration of the IMP and the identity of the hydrophobic moiety. The hydrophobic moiety may be added at any convenient site in the IMP, preferably at either the 5' or 3' end; in the case of addition of a cholesterol moiety to an IMP, the cholesterol moiety is preferably added to the 5' end of the IMP, using conventional chemical reactions (see, for example, Godard et al. (1995) *Eur. J. Biochem.* 232:404-410). Preferably, microcarriers for use in IMP/MC complexes linked by hydrophobic bonding are made from hydrophobic materials, such as oil droplets or hydrophobic polymers, although hydrophilic materials modified to incorporate hydrophobic moieties may be utilized as well. When the microcarrier is a liposome or other liquid phase microcarrier comprising a lumen, the IMP/MC complex is formed by mixing the IMP and the MC after preparation of the MC, in order to avoid encapsulation of the IMP during the MC preparation process.

Non-covalent IMP/MC complexes bound by electrostatic binding typically exploit the highly negative charge of the polynucleotide backbone. Accordingly, microcarriers for use in non-covalently bound IMP/MC complexes are generally positively charged (cationic) at physiological pH (e.g., about pH 6.8-7.4). The microcarrier may intrinsically possess a positive charge, but microcarriers made from compounds not normally possessing a positive charge may be derivatized or otherwise modified to become positively charged (cationic). For example, the polymer used to make the microcarrier may be derivatized to add positively charged groups, such as primary amines. Alternately, positively charged compounds may be incorporated in the formulation of the microcarrier during manufacture (e.g., positively charged surfactants may be used during the manufacture of poly(lactic acid)/poly(glycolic acid) copolymers to confer a positive charge on the resulting microcarrier particles).

As described herein, to prepare cationic microspheres, cationic lipids or polymers, for example, 1,2-dioleoyl-1,2,3-trimethylammoniopropane (DOTAP), cetyltrimethylammonium bromide (CTAB) or polylysine, are added either to DP or CP, as per their solubility in these phases.

As described herein, IMP/MC complexes can be preformed by adsorption onto cationic microspheres by incubation of polynucleotide and the particles, preferably in an aqueous admixture. Such incubation may be carried out under any desired conditions, including ambient (room) temperature (e.g., approximately 20° C.) or under refrigeration (e.g., 4° C.). Because cationic microspheres and polynucleotides associate relatively quickly, the incubation may be for any convenient time period, such as 5, 10, 15 minutes or more, including overnight and longer incubations. For example, polynucleotides containing ISS can be adsorbed onto the cationic microspheres by overnight aqueous incubation of polynucleotide and the particles at 4° C. However, because cationic microspheres and polynucleotides spontaneously associate, the IMP/MC complex can be formed by simple co-administration of the polynucleotide and the MC. Microspheres may be characterized for size and surface charge before and after polynucleotide association. Selected batches may then evaluated for activity against suitable controls in, for example, established human peripheral blood mononuclear cell (PBMC), as described herein, and mouse splenocyte assays. The formulations may also evaluated in suitable animal models.

Non-covalent IMP/MC complexes linked by nucleotide base pairing may be produced using conventional methodologies. Generally, base-paired IMP/MC complexes are produced using a microcarrier comprising a bound, preferably a covalently bound, polynucleotide (the "capture polynucleotide") that is at least partially complementary to the IMP. The segment of complementarity between the IMP and the capture nucleotide is preferably at least 6, 8, 10 or 15 contiguous base pairs, more preferably at least 20 contiguous base pairs. The capture nucleotide may be bound to the MC by any method known in the art, and is preferably covalently bound to the IMP at the 5' or 3' end.

In other embodiments, a binding pair may be used to link the IMP and MC in an IMP/MC complex. The binding pair may be a receptor and ligand, an antibody and antigen (or epitope), or any other binding pair which binds at high affinity (e.g., $K_d$ less than about $10^{-8}$). One type of preferred binding pair is biotin and streptavidin or biotin and avidin, which form very tight complexes. When using a binding pair to mediate IMP/MC complex binding, the IMP is derivatized, typically by a covalent linkage, with one member of the binding pair, and the MC is derivatized with the other member of the binding pair. Mixture of the two derivatized compounds results in IMP/MC complex formation.

Many IMP/MC complex embodiments do not include an antigen, and certain embodiments exclude antigen(s) associated with the disease or disorder which is the object of the IMP/MC complex therapy. In further embodiments, the IMP is also bound to one or more antigen molecules. Antigen may be coupled with the IMP portion of an IMP/MC complex in a variety of ways, including covalent and/or non-covalent interactions, as described, for example, in WO 98/16247. Alternately, the antigen may be linked to the microcarrier. The link between the antigen and the IMP in IMP/MC complexes comprising an antigen bound to the IMP can be made by techniques described herein and known in the art, including, but not limited to, direct covalent linkage, covalent conjugation via a crosslinker moiety (which may include a spacer arm), noncovalent conjugation via a specific binding pair (e.g., biotin and avidin), and noncovalent conjugation via electrostatic or hydrophobic bonding.

Methods of the Invention

The invention provides methods of modulating an immune response in an individual, preferably a mammal, more preferably a human, comprising administering to the individual an ISS-containing polynucleotide as described herein. Immunomodulation may include stimulating a Th1-type immune response and/or inhibiting or reducing a Th2-type immune response. The ISS-containing polynucleotide is administered in an amount sufficient to modulate an immune response. As described herein, modulation of an immune response may be humoral and/or cellular, and is measured using standard techniques in the art and as described herein.

A number of individuals are suitable for receiving the immunomodulatory polynucleotide(s) described herein. Preferably, but not necessarily, the individual is human.

In certain embodiments, the individual suffers from a disorder associated with a Th2-type immune response, such as allergies or allergy-induced asthma. Administration of an ISS-containing polynucleotide results in immunomodulation, increasing levels of one or more Th1-type response associated cytokines, which may result in a reduction of the Th2-type response features associated with the individual's response to the allergen. Immunomodulation of individuals with Th2-type response associated disorders results in a reduction or improvement in one or more of the symptoms of the disorder. Where the disorder is allergy or allergy-induced asthma, improvement in one or more of the symptoms includes a reduction one or more of the following: rhinitis, allergic conjunctivitis, circulating levels of IgE, circulating levels of histamine and/or requirement for 'rescue' inhaler therapy (e.g., inhaled albuterol administered by metered dose inhaler or nebulizer).

In further embodiments, the individual subject to the immunomodulatory therapy of the invention is an individual receiving a vaccine. The vaccine may be a prophylactic vaccine or a therapeutic vaccine. A prophylactic vaccine comprises one or more epitopes associated with a disorder for which the individual may be at risk (e.g., *M. tuberculosis* antigens as a vaccine for prevention of tuberculosis). Therapeutic vaccines comprise one or more epitopes associated with a particular disorder affecting the individual, such as *M. tuberculosis* or *M. bovis* surface antigens in tuberculosis patients, antigens to which the individual is allergic (i.e., allergy desensitization therapy) in individuals subject to allergies, tumor cells from an individual with cancer (e.g., as described in U.S. Pat. No. 5,484,596), or tumor associated antigens in cancer patients. As shown in Example 3 below, administration of ISS-containing polynucleotides in conjunction with a hepatitis virus antigen, hepatitis B surface antigen (HBsAg), resulted in increased titers of anti-HBsAg antibodies in primates as compared to administration of HBsAg alone.

The ISS-containing polynucleotide may be given in conjunction with the vaccine (e.g., in the same injection or a contemporaneous, but separate, injection) or the ISS-containing polynucleotide may be administered separately (e.g., at least 12 hours before or after administration of the vaccine). In certain embodiments, the antigen(s) of the vaccine is part of the ISS, by either covalent or non-covalent linkage to the ISS. Administration of immunomodulatory polynucleotide therapy to an individual receiving a vaccine results in an immune response to the vaccine that is shifted towards a Th1-type response as compared to individuals which receive vaccine without ISS-containing polynucleotide. Shifting towards a Th1-type response may be recognized by a delayed-type hypersensitivity (DTH) response to the antigen(s) in the vaccine, increased IFN-γ and other Th1-type response associated cytokines, production of CTLs specific for the antigen(s) of the vaccine, low or reduced levels of IgE specific for the antigen(s) of the vaccine, a reduction in Th2-associated antibodies specific for the antigen(s) of the vaccine, and/or an increase in Th1-associated antibodies specific for the antigen(s) of the vaccine. In the case of therapeutic vaccines, administration of ISS-containing polynucleotide and vaccine results in amelioration of one or more symptoms of the disorder which the vaccine is intended to treat. As will be apparent to one of skill in the art, the exact symptom(s) and manner of their improvement will depend on the disorder sought to be treated. For example, where the therapeutic vaccine is for tuberculosis, ISS-containing polynucleotide treatment with vaccine results in reduced coughing, pleural or chest wall pain, fever, and/or other symptoms known in the art. Where the vaccine is an allergen used in allergy desensitization therapy, the treatment results in a reduction in the symptoms of allergy (e.g., reduction in rhinitis, allergic conjunctivitis, circulating levels of IgE, and/or circulating levels of histamine).

Other embodiments of the invention relate to immunomodulatory therapy of individuals having a pre-existing disease or disorder, such as cancer or an infectious disease. Cancer is an attractive target for immunomodulation because most cancers express tumor-associated and/or tumor specific antigens which are not found on other cells in the body. Stimulation of a Th1-type response against tumor cells results in direct and/or bystander killing of tumor cells by the immune system, leading to a reduction in cancer cells and/or a reduction in symptom(s). Administration of an ISS-containing polynucleotide to an individual having cancer results in stimulation of a Th1-type immune response against the tumor cells. Such an immune response can kill tumor cells, either by direct action of cellular immune system cells (e.g., CTLs) or components of the humoral immune system, or by bystander effects on cells proximal to cells targeted by the immune system. See, for example, Cho et al. (2000) *Nat. Biotechnol.* 18:509-514. In the cancer context, administration of ISS-containing polynucleotides may further comprise administration of one or more additional therapeutic agents such as, for example, anti-tumor antibodies, chemotherapy regimens and/or radiation treatments. Anti-tumor antibodies, including, but not limited to anti-tumor antibody fragments and/or derivatives thereof, and monoclonal anti-tumor antibodies, fragments and/or derivatives thereof, are known in the art as is administration of such antibody reagents in cancer therapy (e.g., RITUXAN® (rituximab); HERCEPTIN® (trastuzumab)). Administration of one or more additional therapeutic agents may occur before, after and/or concurrent with administration of the ISS-containing polynucleotides.

Immunomodulatory therapy in accordance with the invention is also useful for individuals with infectious diseases, particularly infectious diseases which are resistant to humoral immune responses (e.g., diseases caused by mycobacterial infections and intracellular pathogens). Immunomodulatory therapy may be used for the treatment of infectious diseases caused by cellular pathogens (e.g., bacteria or protozoans) or by subcellular pathogens (e.g., viruses). ISS therapy may be administered to individuals suffering from mycobacterial diseases such as tuberculosis (e.g., *M. tuberculosis* and/or *M. bovis* infections), leprosy (i.e., *M. leprae* infections), or *M. marinum* or *M. ulcerans* infections. ISS therapy is also useful for the treatment of viral infections, including infections by influenza virus, respiratory syncytial virus (RSV), hepatitis virus B, hepatitis virus C, herpes viruses, particularly herpes simplex viruses, and papilloma viruses. Diseases caused by intracellular parasites such as malaria (e.g., infection by *Plasmodium vivax, P. ovale, P. falciparum* and/or *P. malariae*), leishmaniasis (e.g., infection by *Leishmania donovani, L. tropica, L. mexicana, L. braziliensis, L. peruviana, L. infantum, L. chagasi,* and/or *L. aethiopica*), and toxoplasmosis (i.e., infection by *Toxoplasmosis gondii*) also benefit from ISS therapy. ISS therapy is also useful for treatment of parasitic diseases such as schistosomiasis (i.e., infection by blood flukes of the genus *Schistosoma* such as *S. haematobium, S. mansoni, S. japonicum,* and *S. mekongi*) and clonorchiasis (i.e., infection by *Clonorchis sinensis*). Administration of an ISS-containing polynucleotide to an individual suffering from an infectious disease results in an amelioration of symptoms of the infectious disease. In some embodiments, the infectious disease is not a viral disease.

The invention further provides methods of increasing or stimulating at least one Th1-associated cytokine in an individual, including IL-2, IL-12, TNF-β, IFN-γ and IFN-α. In certain embodiments, the invention provides methods of increasing or stimulating IFN-γ in an individual, particularly in an individual in need of increased IFN-γ levels, by administering an effective amount of an ISS-containing polynucleotide to the individual such that IFN-γ is increased. Individuals in need of increased IFN-γ are those having disorders which generally respond to the administration of IFN-γ. Such disorders include a number of inflammatory disorders including, but not limited to, ulcerative colitis. Such disorders also include a number of fibrotic disorders, including, but not limited to, idiopathic pulmonary fibrosis (IPF), scleroderma, cutaneous radiation-induced fibrosis, hepatic fibrosis including schistosomiasis-induced hepatic fibrosis, renal fibrosis as well as other conditions which may be improved by administration of IFN-γ. Administration of ISS-containing polynucleotide in accordance with the invention results in an increase in IFN-γ levels, and results in amelioration of one or more symptoms, stabilization of one or more symptoms, and/or prevention or slowing of progression (e.g., reduction or elimination of additional lesions or symptoms) of the disorder which responds to IFN-γ.

The methods of the invention may be practiced in combination with other therapies which make up the standard of care for the disorder, such as administration of anti-inflammatory agents such as systemic corticosteroid therapy (e.g., cortisone) in IPF.

In certain embodiments, the invention provides methods of increasing IFN-α in an individual, particularly in an individual in need of increased IFN-α levels, by administering an effective amount of an ISS-containing polynucleotide to the individual such that IFN-α levels are increased. Individuals in need of increased IFN-α are those having disorders which generally respond to the administration of IFN-α, including recombinant IFN-α, including, but not limited to, viral infections and cancer. In certain embodiments, immunomodulatory polynucleotides effective for inducing IFN-α production comprise one or more TCG and/or T, 5-bromocytosine, G sequence(s) in addition to the ISS, particularly at the 5' end of the ISS, as described herein. The additional TCG(s) and/or T, 5-bromocytosine, G(s) may be immediately 5' and adjacent to the ISS or may be 5' to the ISS with one or more bases separating the TCG and/or T, 5-bromocytosine, G from the ISS. In some embodiments, the additional TCG and/or T, 5-bromocytosine, G sequence(s) is created by the addition of a T or a TC or a T, 5-bromocytosine to the 5' end of the ISS. In some embodiments where the additional TCG or T, 5-bromocytosine, G sequence is created by the addition of a T or a TC or a T, 5-bromocytosine to the 5' end of the ISS, the additional sequence may create a TCGA or a T, 5-bromocytosine, G, A sequence with the ISS.

Examples of immunomodulatory polynucleotides particularly effective for inducing IFN-α production include, but are not limited to, SEQ ID NO: 1, 14, 19, 46, 24, 11, 18, 35, 12, 13, 28 and 36.

Administration of ISS-containing polynucleotide in accordance with the invention results in an increase in IFN-α levels, and results in amelioration of one or more symptoms, stabilization of one or more symptoms, and/or prevention or slowing of progression (e.g., reduction or elimination of additional lesions or symptoms) of the disorder which responds to IFN-α. The methods of the invention may be practiced in combination with other therapies which make up the standard of care for the disorder, such as administration of anti-viral agents for viral infections.

Also provided are methods of reducing levels, particularly serum levels, of IgE in an individual having an IgE-related disorder by administering an effective amount of an ISS-containing polynucleotide to the individual. In such methods, the immunomodulatory polynucleotide may be administered alone (e.g., without antigen) or administered with antigen, such as an allergen. Reduction in IgE results in an amelioration of one or more symptoms of the IgE-related disorder. Such symptoms include allergy symptoms such as rhinitis, conjunctivitis, in decreased sensitivity to allergens, a reduction in the symptoms of allergy in an individual with allergies, or a reduction in severity of an allergic response. Accordingly, the invention also provides methods of treating an allergic condition in an individual. In some embodiments, methods of treating an allergic condition include administering the immunomodulatory polynucleotide with a particular amount or dose of antigen. With any additional antigen administration, the amount or dose of antigen administered can remain the same, can decease or can increase (as in conventional desensitization therapy) over the course of treatment.

In some embodiments, the invention provides methods of stimulating CTL production in an individual, particularly in an individual in need of increased number and/or activity of CTLs, comprising administering an effective amount of an ISS-containing polynucleotide to the individual such that CTL production is increased. Individuals in need of increased CTL production are those having disorders which generally respond to CTL activity. Such disorders include, but not limited to, cancer and intracellular infections. Administration of ISS-containing polynucleotide in accordance with the invention results in an increase in CTL levels, and results in amelioration of one or more symptoms, stabilization of one or more symptoms, and/or prevention or slowing of progression (e.g., reduction or elimination of additional lesions or symptoms) of the disorder which responds to CTL activity.

Methods of the invention include any embodiments described herein, such as administering ISS-containing polynucleotides in the form of immunomodulatory polynucleotide/microcarrier complex (with or without antigen, or with or without antigen over a course of administrations), or in proximate association with an antigen.

As will be apparent to one of skill in the art, the methods of the invention may be practiced in combination with other therapies for the particular indication for which the ISS-containing polynucleotide is administered. For example, ISS therapy may be administered in conjunction with anti-malarial drugs such as chloroquine for malaria patients, in conjunction with leishmanicidal drugs such as pentamidine and/or allopurinol for leishmaniasis patients, in conjunction with anti-mycobacterial drugs such as isoniazid, rifampin and/or ethambutol in tuberculosis patients, or in conjunction with allergen desensitization therapy for atopic (allergy) patients.

As described herein, administration of ISS-containing polynucleotides may further comprise administration of one or more additional immunotherapeutic agents (i.e., an agent which acts via the immune system and/or is derived from the immune system) including, but not limited to, cytokine, adjuvants and antibodies (including, but not limited to, antibody fragments and/or derivatives and monoclonal antibodies, fragments and/or derivatives thereof). Examples of therapeutic antibodies include those used in the cancer context (e.g., anti-tumor antibodies). Administration of such additional immunotherapeutic agents applies to all the methods described herein.

An ISS-containing polynucleotide may also be administered in conjunction with an adjuvant. Administration of an antigen with an ISS and an adjuvant leads to a potentiation of a immune response to the antigen and thus, can result in an enhanced immune response compared to that which results from a composition comprising the ISS and antigen alone. Adjuvants are known in the art and include, but are not limited to, oil-in-water emulsions, water-in oil emulsions, alum (aluminum salts), liposomes and microparticles, including but not limited to, polystyrene, starch, polyphosphazene and polylactide/polyglycosides. Other suitable adjuvants also include, but are not limited to, MF59, DETOX™ (Ribi), squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) Nature 344:873-875, as well as, lipid-based adjuvants and others described herein. For veterinary use and for production of antibodies in animals, mitogenic components of Freund's adjuvant (both complete and incomplete) can be used.

Administration and Assessment of the Immune Response

The ISS-containing polynucleotide can be administered in combination with other pharmaceutical and/or immunogenic and/or immunostimulatory agents, as described herein, and can be combined with a physiologically acceptable carrier thereof (and as such the invention includes these compositions). The ISS-containing polynucleotide may be any of those described herein.

Accordingly, the ISS-containing polynucleotide can be administered in conjunction with other immunotherapeutic agents including, but not limited to, cytokine, adjuvants and antibodies.

As with all immunogenic compositions, the immunologically effective amounts and method of administration of the particular ISS-containing polynucleotide formulation can vary based on the individual, what condition is to be treated and other factors evident to one skilled in the art. Factors to be considered include the antigenicity of antigen if administered, whether or not the ISS-containing polynucleotide will be administered with or covalently attached to an adjuvant, delivery molecule and/or antigen, route of administration and the number of immunizing doses to be administered. Such factors are known in the art and it is well within the skill of those in the art to make such determinations without undue experimentation. A suitable dosage range is one that provides the desired modulation of immune response (e.g., stimulation of IFN-γ and/or IFN-α). When an immune response to an antigen is desired, a suitable dosage range is one that provides the desired modulation of immune response to the antigen. Generally, dosage is determined by the amount of ISS-containing polynucleotide administered to the patient, rather than the overall quantity of ISS-containing composition administered. Useful dosage ranges of the ISS-containing polynucleotide, given in amounts of ISS-containing polynucleotide delivered, may be, for example, from about any of the following: 1 to 500 µg/kg, 100 to 400 µg/kg, 200 to 300 µg/kg, 1 to 100 µg/kg, 100 to 200 µg/kg, 300 to 400 µg/kg, 400 to 500 µg/kg. The absolute amount given to each patient depends on pharmacological properties such as bioavailability, clearance rate and route of administration.

The effective amount and method of administration of the particular ISS-containing polynucleotide formulation can vary based on the individual patient, desired result and/or type of disorder, the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. A suitable dosage range is one that provides sufficient ISS-containing composition to attain a tissue concentration of about 1-10 µM as measured by blood levels. The absolute amount given to each patient depends on pharmacological properties such as bioavailability, clearance rate and route of administration.

As described herein, APCs and tissues with high concentration of APCs are preferred targets for the ISS-containing polynucleotide. Thus, administration of ISS-containing polynucleotide to mammalian skin and/or mucosa, where APCs are present in relatively high concentration, is preferred.

The present invention provides ISS-containing polynucleotide formulations suitable for topical application including, but not limited to, physiologically acceptable implants, ointments, creams, rinses and gels. Topical administration is, for instance, by a dressing or bandage having dispersed therein a delivery system, by direct administration of a delivery system into incisions or open wounds, or by transdermal administration device directed at a site of interest. Creams, rinses, gels or ointments having dispersed therein an ISS-containing polynucleotide are suitable for use as topical ointments or wound filling agents.

Preferred routes of dermal administration are those which are least invasive. Preferred among these means are transdermal transmission, epidermal administration and subcutaneous injection. Of these means, epidermal administration is preferred for the greater concentrations of APCs expected to be in intradermal tissue.

Transdermal administration is accomplished by application of a cream, rinse, gel, etc. capable of allowing the ISS-containing polynucleotide to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference.

For transdermal transmission, iontophoresis is a suitable method. Iontophoretic transmission can be accomplished using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or periodically. Preparation and use of the patch should be performed according to the manufacturer's printed instructions which accompany the LECTRO PATCH product; those instructions are incorporated herein by this reference. Other occlusive patch systems are also suitable.

For transdermal transmission, low-frequency ultrasonic delivery is also a suitable method. Mitragotri et al. (1995) *Science* 269:850-853. Application of low-frequency ultrasonic frequencies (about 1 MHz) allows the general controlled delivery of therapeutic compositions, including those of high molecular weight.

Epidermal administration essentially involves mechanically or chemically irritating the outermost layer of the epidermis sufficiently to provoke an immune response to the irritant. Specifically, the irritation should be sufficient to attract APCs to the site of irritation.

An exemplary mechanical irritant means employs a multiplicity of very narrow diameter, short tines which can be used to irritate the skin and attract APCs to the site of irritation, to take up ISS transferred from the end of the tines. For example, the MONO-VACC old tuberculin test manufactured by Pasteur Merieux of Lyon, France contains a device suitable for introduction of immunomodulatory polynucleotide-containing compositions.

The device (which is distributed in the U.S. by Connaught Laboratories, Inc. of Swiftwater, Pa.) consists of a plastic container having a syringe plunger at one end and a tine disk at the other. The tine disk supports a multiplicity of narrow diameter tines of a length which will just scratch the outermost layer of epidermal cells. Each of the tines in the MONO-VACC kit is coated with old tuberculin; in the present invention, each needle is coated with a pharmaceutical composition of immunomodulatory polynucleotide formulation. Use of the device is preferably according to the manufacturer's written instructions included with the device product. Similar devices which can also be used in this embodiment are those which are currently used to perform allergy tests.

Another suitable approach to epidermal administration of ISS-containing polynucleotide is by use of a chemical which irritates the outermost cells of the epidermis, thus provoking a sufficient immune response to attract APCs to the area. An example is a keratinolytic agent, such as the salicylic acid used in the commercially available topical depilatory creme sold by Noxema Corporation under the trademark NAIR. This approach can also be used to achieve epithelial administration in the mucosa. The chemical irritant can also be applied in conjunction with the mechanical irritant (as, for example, would occur if the MONO-VACC type tine were also coated with the chemical irritant). The ISS-containing polynucleotide can be suspended in a carrier which also contains the chemical irritant or coadministered therewith.

Parenteral routes of administration include but are not limited to electrical (iontophoresis) or direct injection such as direct injection into a central venous line, intravenous, intramuscular, intraperitoneal, intradermal, or subcutaneous injection. Formulations of ISS-containing polynucleotide suitable for parenteral administration are generally formulated in USP water or water for injection and may further comprise pH buffers, salts bulking agents, preservatives, and other pharmaceutically acceptable excipients. Immunomodulatory polynucleotide for parenteral injection may be formulated in pharmaceutically acceptable sterile isotonic solutions such as saline and phosphate buffered saline for injection.

Gastrointestinal routes of administration include, but are not limited to, ingestion and rectal. The invention includes formulations ISS-containing polynucleotide suitable for gastrointestinal administration including, but not limited to, pharmaceutically acceptable powders, pills or liquids for ingestion and suppositories for rectal administration. As will be apparent to one of skill in the art, pills or suppositories will further comprise pharmaceutically acceptable solids, such as starch, to provide bulk for the composition.

Naso-pharyngeal and pulmonary administration include are accomplished by inhalation, and include delivery routes such as intranasal, transbronchial and transalveolar routes. The invention includes formulations of ISS-containing polynucleotide suitable for administration by inhalation including, but not limited to, liquid suspensions for forming aerosols as well as powder forms for dry powder inhalation delivery systems. Devices suitable for administration by inhalation of ISS formulations include, but are not limited to, atomizers, vaporizers, nebulizers, and dry powder inhalation delivery devices.

As is well known in the art, solutions or suspensions used for the routes of administration described herein can include any one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

As is well known in the art, pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. It may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

As is well known in the art, sterile injectable solutions can be prepared by incorporating the active compound(s) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

The choice of delivery routes can be used to modulate the immune response elicited. For example, IgG titers and CTL activities were identical when an influenza virus vector was administered via intramuscular or epidermal (gene gun) routes; however, the muscular inoculation yielded primarily IgG2a, while the epidermal route yielded mostly IgG1. Pertmer et al. (1996) *J. Virol.* 70:6119-6125. Thus, one skilled in the art can take advantage of slight differences in immunogenicity elicited by different routes of administering the immunomodulatory polynucleotides of the present invention.

The above-mentioned compositions and methods of administration are meant to describe but not limit the methods of administering the formulations of ISS-containing polynucleotides of the invention. The methods of producing the various compositions and devices are within the ability of one skilled in the art and are not described in detail here.

Analysis (both qualitative and quantitative) of the immune response to ISS can be by any method known in the art, including, but not limited to, measuring antigen-specific antibody production (including measuring specific antibody subclasses), activation of specific populations of lymphocytes such as CD4+ T cells, NK cells or CTLs, production of cytokines such as IFN-γ, IFN-α, IL-2, IL-4, IL-5, IL-10 or IL-12 and/or release of histamine. Methods for measuring specific antibody responses include enzyme-linked immunosorbent assay (ELISA) and are well known in the art. Measurement of numbers of specific types of lymphocytes such as CD4+ T cells can be achieved, for example, with fluorescence-activated cell sorting (FACS). Cytotoxicity and CTL assays can be performed for instance as described in Raz et al. (1994) *Proc. Natl. Acad. Sci. USA* 91:9519-9523 and Cho et al. (2000). Cytokine concentrations can be measured, for example, by ELISA. These and other assays to evaluate the immune response to an immunogen are well known in the art. See, for example, Selected Methods in Cellular Immunology (1980) Mishell and Shiigi, eds., W.H. Freeman and Co.

Preferably, a Th1-type response is stimulated, i.e., elicited and/or enhanced. With reference to the invention, stimulating a Th1-type immune response can be determined in vitro or ex vivo by measuring cytokine production from cells treated with ISS as compared to those treated without ISS. Methods to determine the cytokine production of cells include those methods described herein and any known in the art. The type of cytokines produced in response to ISS treatment indicate a Th1-type or a Th2-type biased immune response by the cells. As used herein, the term "Th1-type biased" cytokine production refers to the measurable increased production of cytokines associated with a Th1-type immune response in the presence of a stimulator as compared to production of such cytokines in the absence of stimulation. Examples of such Th1-type biased cytokines include, but are not limited to, IL-2, IL-12, IFN-γ and IFN-α. In contrast, "Th2-type biased cytokines" refers to those associated with a Th2-type immune response, and include, but are not limited to, IL-4, IL-5, and IL-13. Cells useful for the determination of ISS activity include cells of the immune system, primary cells isolated from a host and/or cell lines, preferably APCs and lymphocytes, even more preferably macrophages and T cells.

Stimulating a Th1-type immune response can also be measured in a host treated with an ISS-containing polynucleotide can be determined by any method known in the art including, but not limited to: (1) a reduction in levels of IL-4 or IL-5 measured before and after antigen-challenge; or detection of lower (or even absent) levels of IL-4 or IL-5 in an ISS treated host, optionally as compared to an antigen-primed, or primed and challenged, control treated without ISS; (2) an increase in levels of IL-12, IL-18 and/or IFN (α, β or γ) before and after antigen challenge; or detection of higher levels of IL-12, IL-18 and/or IFN (α, β or γ) in an ISS treated host as compared to an antigen-primed or, primed and challenged, control treated without ISS; (3) "Th1-type biased" antibody production in an ISS treated host as compared to a control treated without ISS; and/or (4) a reduction in levels of antigen-specific IgE as measured before and after antigen challenge; or detection of lower (or even absent) levels of antigen-specific IgE in an ISS treated host as compared to an antigen-primed, or primed and challenged, control treated without ISS. A variety of these determinations can be made by measuring cytokines made by APCs and/or lymphocytes, preferably macrophages and/or T cells, in vitro or ex vivo using methods described herein or any known in the art. Some of these determinations can be made by measuring the class and/or subclass of antigen-specific antibodies using methods described herein or any known in the art.

The class and/or subclass of antigen-specific antibodies produced in response to ISS-containing polynucleotide treatment indicate a Th1-type or a Th2-type biased immune response by the cells. As used herein, the term "Th1-type biased" antibody production refers to the measurable increased production of antibodies associated with a Th1-type immune response (i.e., Th1-associated antibodies). One or more Th1 associated antibodies may be measured. Examples of such Th1-type biased antibodies include, but are not limited to, human IgG1 and/or IgG3 (see, e.g., Widhe et al. (1998) *Scand. J. Immunol.* 47:575-581 and de Martino et al. (1999) *Ann. Allergy Asthma Immunol.* 83:160-164) and murine IgG2a. In contrast, "Th2-type biased antibodies" refers to those associated with a Th2-type immune response, and include, but are not limited to, human IgG2, IgG4 and/or IgE (see, e.g., Widhe et al. (1998) and de Martino et al. (1999)) and murine IgG1 and/or IgE.

The Th1-type biased cytokine induction which occurs as a result of administration of ISS-containing polynucleotide produces enhanced cellular immune responses, such as those performed by NK cells, cytotoxic killer cells, Th1 helper and memory cells. These responses are particularly beneficial for use in protective or therapeutic vaccination against viruses, fungi, protozoan parasites, bacteria, allergic diseases and asthma, as well as tumors.

In some embodiments, a Th2 response is suppressed (reduced). Suppression of a Th2 response may be determined by, for example, reduction in levels of Th2-associated cytokines, such as IL-4 and IL-5, reduction in the levels of Th2-associated antibodies, as well as IgE reduction and reduction in histamine release in response to allergen.

Kits of the Invention

The invention provides kits. In certain embodiments, the kits of the invention generally comprise one or more containers comprising any ISS-containing polynucleotide as described herein. The kits may further comprise a suitable set of instructions, generally written instructions, relating to the use of the ISS-containing polynucleotide for any of the methods described herein (e.g., immunomodulation, ameliorating one or more symptoms of an infectious disease, increasing IFN-γ levels, increasing IFN-α levels, or ameliorating an IgE-related disorder).

The kits may comprise ISS-containing polynucleotide packaged in any convenient, appropriate packaging. For example, if the ISS-containing polynucleotide is a dry formulation (e.g., freeze dried or a dry powder), a vial with a resilient stopper is normally used, so that the ISS-containing polynucleotide may be easily resuspended by injecting fluid through the resilient stopper. Ampoules with non-resilient, removable closures (e.g., sealed glass) or resilient stoppers are most conveniently used for liquid formulations of ISS-containing polynucleotide. Also contemplated are packages for use in combination with a specific device, such as an inhaler, nasal administration device (e.g., an atomizer) or an infusion device such as a minipump.

The instructions relating to the use of ISS-containing polynucleotide generally include information as to dosage, dosing schedule, and route of administration for the intended method of use. The containers of ISS-containing polynucleotide may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

In some embodiments, the kits further comprise an antigen (or one or more antigens), which may or may not be packaged in the same container (formulation) as the ISS-containing polynucleotide(s). Antigens have been described herein.

In certain embodiments, the kits of the invention comprise an ISS-containing polynucleotide in the form of an immunomodulatory polynucleotide/microcarrier complex (IMP/MC) and may further comprise a set of instructions, generally written instructions, relating to the use of the IMP/MC complex for any of the methods described herein (e.g., immunomodulation, ameliorating one or more symptoms of an infectious disease, increasing IFN-γ levels, increasing IFN-α levels, or ameliorating an IgE-related disorder).

In some embodiments, kits of the invention comprise materials for production of IMP/MC complex generally include separate containers of IMP and MC, although in certain embodiments materials for producing the MC are supplied rather than preformed MC. The IMP and MC are preferably supplied in a form which allows formation of IMP/MC complex upon mixing of the supplied IMP and MC. This configuration is preferred when the IMP/MC complex is linked by non-covalent bonding. This configuration is also preferred when the IMP and MC are to be crosslinked via a heterobifunctional crosslinker; either IMP or the MC is supplied in an "activated" form (e.g., linked to the heterobifunctional crosslinker such that a moiety reactive with the IMP is available).

Kits for IMP/MC complexes comprising a liquid phase MC preferably comprise one or more containers including materials for producing liquid phase MC. For example, an IMP/MC kit for oil-in-water emulsion MC may comprise one or more containers containing an oil phase and an aqueous phase. The contents of the container are emulsified to produce the MC, which may be then mixed with the IMP, preferably an IMP which has been modified to incorporate a hydrophobic moiety. Such materials include oil and water, for production of oil-in-water emulsions, or containers of lyophilized liposome components (e.g., a mixture of phospholipid, cholesterol and a surfactant) plus one or more containers of an aqueous phase (e.g., a pharmaceutically-acceptable aqueous buffer).

The following Examples are provided to illustrate, but not limit, the invention.

EXAMPLES

Example 1

Immunomodulation of Murine Cells by ISS-Containing Polynucleotides

Immunomodulatory polynucleotides (i.e., containing an ISS) or control polynucleotides (i.e., without an ISS) were assayed for immunomodulatory activity on mouse splenocytes. The polynucleotides tested were fully modified phosphorothioate oligodeoxynucleotides. Among the polynucleotides tested were 5'-TGACTGTGAACGTTCGAGATGA-3' (SEQ ID NO: 59) (positive control) and 5'-TGACTGTGAACCTTA-GAGATGA-3' (SEQ ID NO: 60) (negative control).

Fragments of BALB/c mouse spleen were digested with collagenase/dispase (0.1 U/mL/0.8 U/mL) dissolved in phosphate buffered saline (PBS) for 45 minutes at 37° C., then mechanically dispersed by forcing the digested fragments through metal screens. The dispersed splenocytes were pelleted by centrifugation, then resuspended in fresh medium (RPMI 1640 with 10% fetal calf serum, plus 50 units/mL penicillin, 50 µg/mL streptomycin, 2 mM glutamine, and 0.05 mM β-mercaptoethanol).

Mouse splenocytes were dispensed into wells of 96 well plates ($7 \times 10^7$ cells/ml) and incubated for one hour at 37° C. 100 µL of 2× concentration test sample or control was added and the cells were incubated a further 24 hours. Medium was harvested from each well and tested for cytokine concentrations by ELISA. Polynucleotides were tested at various concentrations including 5.0, 1.0 and 0.1 µg/ml. Control samples included media alone and PANSORBIN® heat-killed, formalin-fixed *Staphylococcus aureus* (SAC) (CalBiochem).

IFN-γ was assayed using a sandwich-format ELISA. Medium from the mouse splenocyte assay was incubated in microtiter plates coated with anti-IFN-γ monoclonal antibody (Nunc). Bound IFN-γ was detected using a biotinylated anti-IFN-γ antibody and streptavidin-horseradish peroxidase conjugated secondary antibody, developed with the chromogenic peroxidase substrate 3,3',5,5'-tetramethylbenzidine (TMB) in the presence of peroxidase, and quantitated by measuring absorbance at 450 nm using a Emax precision microplate reader (Molecular Devices).

Immunomodulatory polynucleotides containing an ISS substantially increased IFN-γ secretion by mouse splenocytes compared to control polynucleotides. Tables 2-5 summarize assay results for IFN-γ produced in response to 5 µg/ml polynucleotide.

TABLE 2

| Mouse splenocyte assays - IFNγ (pg/ml) | | |
|---|---|---|
| test/control | Exp. 1 | Exp. 2 |
| SEQ ID NO: 59 | 164 | 1010 |
| SEQ ID NO: 60 | 18 | 3 |
| SEQ ID NO: 2 | 134 | |
| SEQ ID NO: 47 | 111 | |
| SEQ ID NO: 41 | 131 | |
| SEQ ID NO: 48 | | 3 |

TABLE 2-continued

Mouse splenocyte assays - IFNγ (pg/ml)

| test/control | Exp. 1 | Exp. 2 |
|---|---|---|
| SEQ ID NO: 42 | | 623 |
| SEQ ID NO: 43 | | 794 |
| media | 18 | 3 |
| SAC | 4535 | 12719 |

TABLE 3

Mouse splenocyte assays - IFNγ (pg/ml)

| test/control | Exp. 3 | Exp. 4 |
|---|---|---|
| SEQ ID NO: 59 | 185 | 1090 |
| SEQ ID NO: 60 | 12 | 48 |
| SEQ ID NO: 33 | 140 | |
| SEQ ID NO: 8 | 26 | |
| SEQ ID NO: 9 | 12 | |
| SEQ ID NO: 10 | 12 | |
| SEQ ID NO: 12 | 341 | |
| SEQ ID NO: 13 | 12 | |
| SEQ ID NO: 1 | | 2045 |
| SEQ ID NO: 3 | | 1302 |
| SEQ ID NO: 4 | | 2002 |
| SEQ ID NO: 5 | | 1743 |
| SEQ ID NO: 6 | | 2832 |
| media | 12 | 48 |
| SAC | 2676 | 8753 |

TABLE 4

Mouse splenocyte assay - IFNγ (pg/ml)

| test/control | Exp. 5 |
|---|---|
| SEQ ID NO: 59 | 1051 |
| SEQ ID NO: 60 | 48 |
| SEQ ID NO: 1 | 1335 |
| SEQ ID NO: 14 | 1119 |
| SEQ ID NO: 44 | 716 |
| SEQ ID NO: 17 | 3 |
| SEQ ID NO: 18 | 3 |
| SEQ ID NO: 45 | 274 |
| SEQ ID NO: 46 | 1251 |
| SEQ ID NO: 19 | 1467 |
| SEQ ID NO: 23 | 282 |
| SEQ ID NO: 24 | 1155 |
| SEQ ID NO: 25 | 3 |
| SEQ ID NO: 26 | 3 |
| SEQ ID NO: 27 | 11 |
| SEQ ID NO: 28 | 1331 |
| media | 3 |
| SAC | 924 |

TABLE 5

Mouse splenocyte assays - IFNγ (pg/ml)

| test/control | Exp. 6 | Exp. 7 |
|---|---|---|
| SEQ ID NO: 59 | 435 | 281 |
| SEQ ID NO: 60 | 9 | 18 |
| SEQ ID NO: 1 | 419 | 279 |
| SEQ ID NO: 11 | 149 | |
| SEQ ID NO: 44 | 222 | 342 |
| SEQ ID NO: 9 | | 9 |
| SEQ ID NO: 12 | | 540 |
| SEQ ID NO: 19 | | 625 |
| SEQ ID NO: 55 | | 486 |
| SEQ ID NO: 20 | | 458 |
| SEQ ID NO: 21 | | 9 |
| SEQ ID NO: 22 | | 709 |
| media | 9 | |
| SAC | 3215 | |

Example 2

Immunomodulation of Human Cells by ISS-Containing Polynucleotides

Immunomodulatory polynucleotides (i.e., containing an ISS) or control samples, including polynucleotides without an ISS (5'-TGACTGTGAACCTTAGAGATGA-3 (SEQ ID NO: 60) and 5'-TGACTGTGAAGGTTAGAGATGA-3' (SEQ ID NO: 61)), SAC and media alone, were tested for immunomodulatory activity on human peripheral blood mononuclear cells (PBMCs). The polynucleotides tested were fully modified phosphorothioate oligodeoxynucleotides.

Peripheral blood was collected from volunteers by venipuncture using heparinized syringes. Blood was layered onto FICOLL® (Amersham Pharmacia Biotech) cushion and centrifuged. PBMCs, located at the FICOLL® interface, were collected, then washed twice with cold phosphate buffered saline (PBS). The cells were resuspended and cultured in 24 or 48 well plates at $2\times10^6$ cells/mL in RPMI 1640 with 10% heat-inactivated human AB serum plus 50 units/mL penicillin, 50 µg/mL streptomycin, 300 µg/mL glutamine, 1 mM sodium pyruvate, and 1×MEM non-essential amino acids (NEAA).

The cells were cultured in the presence of test samples (immunomodulatory polynucleotides or controls) at 20 µg/ml for 24 hours, then cell-free medium was collected from each well and assayed for IFN-γ and IFN-α concentration. IFN-γ and IFN-α were assayed using CYTOSCREEN™ ELISA kits from BioSource International, Inc., according to the manufacturer's instructions.

ISS-containing polynucleotides stimulated IFN-γ and/or IFN-α secretion by human PBMCs. In the human PBMC assay, background levels of IFN-γ can vary, even significantly, with the donor. Other cytokines such as IFN-α, however, demonstrate a generally stable pattern of activation and routinely exhibit low background levels under unstimulated conditions. Examples of results from such assays from independent PBMC donors are summarized in Tables 6.

As indicated in Table 6, certain immunomodulatory polynucleotides are effective in boosting IFN-γ levels in human cells. Also as indicated in Table 6, certain immunomodulatory polynucleotides are particularly effective in boosting IFN-α levels in human cells. Such polynucleotides generally include those comprising at least one TCG or T, 5-bromocytosine, G sequence 5' to the ISS or at least one TCG or T, 5-bromocytosine, G sequence created by the addition of a T or a TC or a T, −5-bromocytosine to the 5' end of the ISS. Examples of such immunomodulatory polynucleotides include, but are not limited to, SEQ ID NOs: 1, 14, 19, 46, 24, 11, 18, 12, 13, 28 and 36.

TABLE 6

| Human PBMC Assays - IFN (pg/ml) | | | | |
|---|---|---|---|---|
| Experiment 1: | | | | |
| test/control SEQ ID NO: | Donor 9 IFN-γ | Donor 94 IFN-γ | Donor 9 IFN-α | Donor 94 IFN-α |
| 59 | 20 | 30 | 131 | 274 |
| 60 | 0 | 0 | 0 | 0 |
| 2 | 29 | 19 | 100 | 171 |
| 47 | 39 | 30 | 235 | 341 |
| 41 | 25 | 27 | 89 | 257 |
| 48 | 24 | 24 | 108 | 157 |
| 42 | 10 | 13 | 24 | 48 |
| 43 | 15 | 17 | 102 | 170 |
| media | 0 | 0 | 0 | 0 |
| SAC | 10 | 31 | 536 | 814 |
| Experiment 2: | | | | |
| test/control SEQ ID NO: | Donor 45 IFN-γ | Donor 112 IFN-γ | Donor 45 IFN-α | Donor 112 IFN-α |
| 59 | 25 | 122 | 36 | 45 |
| 60 | 6 | 13 | 4 | 6 |
| 2 | 29 | 196 | 43 | 74 |
| 41 | 47 | 282 | 15 | 48 |
| 42 | 16 | 114 | 10 | 30 |
| 43 | 10 | 144 | 27 | 22 |
| 31 | 20 | 60 | 45 | 26 |
| 33 | 15 | 48 | 62 | 11 |
| 8 | 14 | 122 | 30 | 16 |
| 9 | 9 | 121 | 16 | 11 |
| 10 | 10 | 109 | 23 | 8 |
| 13 | 49 | 475 | 250 | 50 |
| 1 | 162 | 454 | 819 | 281 |
| 11 | 25 | 164 | 281 | 99 |
| 3 | 36 | 399 | 479 | 91 |
| 4 | 30 | 210 | 155 | 51 |
| 5 | 35 | 319 | 495 | 123 |
| 6 | 41 | 188 | 616 | 308 |
| 44 | 21 | 166 | 75 | 20 |
| 14 | 41 | 281 | 475 | 148 |
| media | 0 | 0 | 7 | 39 |
| SAC | 133 | 119 | 42 | 13 |
| Experiment 3: | | | | |
| test/control SEQ ID NO: | Donor 7 IFN-γ | Donor 58 IFN-γ | Donor 7 IFN-α | Donor 58 IFN-α |
| 59 | 769 | 76 | 231 | 14 |
| 60 | 74 | 26 | 0 | 0 |
| 2 | 580 | 110 | 174 | 20 |
| 12 | 512 | 124 | 260 | 29 |
| 55 | 901 | 98 | 738 | 53 |
| 20 | 752 | 63 | 224 | 18 |
| 19 | 1907 | 218 | 734 | 137 |
| 23 | 1628 | 211 | 701 | 120 |
| 24 | 1719 | 326 | 1280 | 208 |
| 45 | 419 | 60 | 256 | 11 |
| 46 | 556 | 77 | 288 | 7 |
| 9 | 328 | 35 | 149 | 17 |
| 17 | 332 | 90 | 376 | 24 |
| 18 | 437 | 75 | 174 | 57 |
| 25 | 561 | 87 | 295 | 61 |
| 1 | 1273 | 236 | 759 | 136 |
| 33 | 488 | 53 | 328 | 15 |
| media | 119 | 0 | 0 | 18 |
| SAC | 977 | 158 | 1269 | 1036 |
| Experiment 4: | | | | |
| test/control SEQ ID NO: | Donor 60 IFN-γ | Donor 65 IFN-γ | Donor 60 IFN-α | Donor 65 IFN-α |
| 59 | 139 | 43 | 44 | 180 |
| 60 | 14 | 0 | 8 | 1 |
| 12 | 335 | 57 | 837 | 742 |
| 9 | 55 | 19 | 32 | 64 |

TABLE 6-continued

| Human PBMC Assays - IFN (pg/ml) | | | | |
|---|---|---|---|---|
| 10 | 76 | 22 | 39 | 56 |
| 13 | 308 | 44 | 248 | 362 |
| 44 | 80 | 24 | 92 | 221 |
| 14 | 167 | 48 | 635 | 1425 |
| 11 | 205 | 50 | 1134 | 1184 |
| 1 | 410 | 92 | 1024 | 1320 |
| media | 0 | 0 | 11 | 1 |
| SAC | 197 | 124 | 285 | 1655 |
| Experiment 5: | | | | |
| test/control SEQ ID NO: | Donor 113 IFN-γ | Donor 114 IFN-γ | Donor 113 IFN-α | Donor 114 IFN-α |
| 59 | 192 | 285 | 189 | 19 |
| 60 | 2 | 21 | 1 | 1 |
| 1 | 299 | 968 | 643 | 192 |
| 19 | 277 | 712 | 548 | 180 |
| 28 | 184 | 341 | 951 | 396 |
| 33 | 68 | 242 | 109 | 63 |
| 34 | 110 | 203 | 359 | 66 |
| 36 | 170 | 523 | 866 | 356 |
| media | 0 | 0 | 1 | 2 |
| SAC | 211 | 780 | 1493 | 997 |
| Experiment 6: | | | | |
| test/control SEQ ID NO: | Donor 101 IFN-γ | Donor 125 IFN-γ | Donor 101 IFN-α | Donor 125 IFN-α |
| 59 | 19 | 207 | 93 | 0 |
| 60 | 0 | 126 | 0 | 0 |
| 44 | 8 | 91 | 230 | 6 |
| 2 | 8 | 249 | 87 | 0 |
| 12 | 38 | 101 | 181 | 0 |
| 45 | 8 | 72 | 91 | 0 |
| 46 | 18 | 174 | 136 | 0 |
| 55 | 35 | 289 | 1102 | 5 |
| 20 | 42 | 126 | 346 | 0 |
| 19 | 32 | 419 | 2999 | 70 |
| 23 | 27 | 115 | 376 | 0 |
| 24 | 45 | 465 | 4025 | 92 |
| 9 | 0 | 150 | 3 | 0 |
| 17 | 24 | 145 | 118 | 0 |
| 18 | 20 | 168 | 29 | 0 |
| 25 | 29 | 228 | 197 | 6 |
| 26 | 18 | 153 | 73 | 0 |
| 27 | 24 | 171 | 346 | 34 |
| 28 | 23 | 298 | 2361 | 108 |
| 1 | 93 | 369 | 1524 | 24 |
| media | 0 | 9 | 0 | 0 |
| SAC | 11 | 39 | 0 | 0 |
| Experiment 7: | | | | |
| test/control SEQ ID NO: | Donor 98 IFN-γ | Donor 123 IFN-γ | Donor 98 IFN-α | Donor 123 IFN-α |
| 59 | 0 | 21 | 7 | 1 |
| 60 | 0 | 1 | 1 | 8 |
| 44 | 0 | 4 | 0 | 14 |
| 12 | 4 | 46 | 9 | 47 |
| 19 | 25 | 139 | 22 | 337 |
| 23 | 0 | 34 | 2 | 68 |
| 24 | 13 | 107 | 30 | 1074 |
| 9 | 0 | 10 | 1 | 7 |
| 18 | 0 | 34 | 14 | 49 |
| 25 | 1 | 21 | 7 | 59 |
| 26 | 0 | 19 | 3 | 31 |
| 27 | 0 | 51 | 15 | 98 |
| 28 | 3 | 37 | 18 | 153 |
| 1 | 103 | 121 | 11 | 217 |
| media | 0 | 0 | 2 | 1 |
| SAC | 3 | 16 | 51 | 265 |

TABLE 6-continued

Human PBMC Assays - IFN (pg/ml)

Experiment 8:

| test/control SEQ ID NO: | Donor 106 IFN-γ | Donor 107 IFN-γ | Donor 106 IFN-α | Donor 107 IFN-α |
|---|---|---|---|---|
| 59 | 72 | 218 | 173 | 224 |
| 60 | 14 | 3 | 0 | 0 |
| 33 | 76 | 231 | 430 | 165 |
| 8 | 54 | 193 | 374 | 129 |
| 9 | 43 | 183 | 179 | 144 |
| 10 | 36 | 122 | 183 | 62 |
| 12 | 54 | 379 | 727 | 2866 |
| 13 | 58 | 264 | 425 | 1853 |
| 1 | 124 | 485 | 1670 | 2534 |
| media | 4 | 2 | 0 | 0 |
| SAC | 120 | 342 | 4000 | 1275 |

Experiment 9:

| test/control SEQ ID NO: | Donor 56 IFN-γ | Donor 82 IFN-γ | Donor 56 IFN-α | Donor 82 IFN-α |
|---|---|---|---|---|
| 59 | 69 | 30 | 87 | 276 |
| 60 | 5 | 5 | 0 | 0 |
| 33 | 62 | 30 | 124 | 151 |
| 8 | 76 | 25 | 79 | 71 |
| 9 | 52 | 16 | 40 | 7 |
| 10 | 28 | 20 | 13 | 32 |
| 12 | 89 | 42 | 226 | 684 |
| 13 | 76 | 37 | 168 | 688 |
| 1 | 82 | 62 | 802 | 3851 |
| media | 2 | 4 | 0 | 0 |
| SAC | 112 | 1432 | 2520 | 4000 |

Experiment 10:

| test/control SEQ ID NO: | Donor 41 IFN-γ | Donor 45 IFN-γ | Donor 41 IFN-α | Donor 45 IFN-α |
|---|---|---|---|---|
| 59 | 0 | 16 | 43 | 363 |
| 60 | 20 | 11 | 16 | 19 |
| 44 | 0 | 7 | 30 | 195 |
| 2 | 0 | 5 | 20 | 164 |
| 47 | 0 | 7 | 32 | 146 |
| 41 | 0 | 9 | 30 | 124 |
| 42 | 0 | 4 | 23 | 44 |
| 43 | 7 | 10 | 43 | 199 |
| 1 | 16 | 31 | 498 | 2726 |
| media | 0 | 0 | 18 | 25 |
| SAC | 624 | 233 | 16931 | 35036 |

Experiment 11:

| test/control SEQ ID NO: | Donor 99 IFN-γ | Donor 100 IFN-γ | Donor 99 IFN-α | Donor 100 IFN-α |
|---|---|---|---|---|
| 59 | 37 | 4 | 519 | 57 |
| 60 | 144 | 27 | 22 | 27 |
| 2 | 23 | 5 | 306 | 76 |
| 47 | 39 | 3 | 235 | 39 |
| 41 | 23 | 1 | 219 | 34 |
| 48 | 32 | 1 | 838 | 53 |
| 42 | 58 | 3 | 342 | 92 |
| 43 | 23 | 0 | 662 | 62 |
| 1 | 61 | 17 | 3680 | 404 |
| media | 0 | 20 | 15 | 60 |
| SAC | 849 | 177 | 3446 | 6230 |

Experiment 12:

| test/control SEQ ID NO: | Donor 83 IFN-γ | Donor 103 IFN-γ | Donor 83 IFN-α | Donor 103 IFN-α |
|---|---|---|---|---|
| 59 | 308 | 16 | 250 | 8 |
| 60 | 49 | 160 | 0 | 0 |
| 61 | 10 | 0 | 0 | 0 |
| 1 | 820 | 109 | 928 | 219 |
| 3 | 625 | 130 | 554 | 71 |
| 4 | 546 | 111 | 188 | 25 |
| 5 | 444 | 158 | 385 | 47 |
| 6 | 276 | 64 | 906 | 160 |
| 2 | 255 | 75 | 347 | 21 |
| 31 | 501 | 11 | 301 | 6 |
| media | 0 | 693 | 3 | 0 |
| SAC | 1471 | 590 | 456 | 515 |

Experiment 13:

| test/control SEQ ID NO: | Donor 26 IFN-γ | Donor 97 IFN-γ | Donor 26 IFN-α | Donor 97 IFN-α |
|---|---|---|---|---|
| 59 | 324 | 541 | 267 | 24 |
| 60 | 6 | 103 | 0 | 1 |
| 12 | 530 | 516 | 949 | 350 |
| 45 | 303 | 214 | 377 | 20 |
| 46 | 536 | 696 | 1274 | 142 |
| 9 | 208 | 301 | 153 | 12 |
| 17 | 515 | 586 | 1628 | 158 |
| 18 | 435 | 238 | 1572 | 64 |
| 1 | 1045 | 879 | 4302 | 1039 |
| 11 | 284 | 163 | 3424 | 299 |
| 44 | 391 | 465 | 2059 | 666 |
| 14 | 414 | 395 | 5172 | 1334 |
| 19 | 638 | 466 | 5874 | 2485 |
| media | 0 | 24 | 0 | 1 |
| SAC | 274 | | 102 | |

Experiment 14:

| test/control SEQ ID NO: | Donor 97 IFN-γ | Donor 124 IFN-γ | Donor 97 IFN-α | Donor 124 IFN-α |
|---|---|---|---|---|
| 59 | 218 | 104 | 76 | 24 |
| 60 | 4 | 18 | 0 | 0 |
| 18 | 206 | 50 | 104 | 22 |
| 35 | 279 | 117 | 219 | 27 |
| media | 0 | 2 | 0 | 3 |
| SAC | 298 | 301 | 1170 | 784 |

Example 3

Primate Immune Response to Antigen+ISS

Immune responses to administration of hepatitis B surface antigen (HBsAg) in the presence of an ISS-containing polynucleotide of the invention were examined in baboons.

HBsAg was recombinant HBsAg produced in yeast. Groups of baboons (five animals per group) included male and female baboons with weights ranging from 8-31 kg (group mean weights at 13-16 kg) at the start of the study.

The baboons were immunized three times, at two month intervals (0, 2 and 4 months), by intramuscular injection (IM) with 20 μg HBsAg in a 1 ml volume. As outlined below, some of the groups also received ISS with the HBsAg.

Bleeds on all animals were collected prior to immunization and at 2 weeks post-immunization. Anti-HBsAg IgG titers were measured as follows. Baboon serum samples were analyzed by AUSAB EIA commercial kit (Abbott Labs Cat. #9006-24 and 1459-05) using human plasma derived HBsAg coated beads. Samples were tested along with a panel of human plasma derived HBsAg positive and negative standards ranging from 0-150 mIU/ml. Biotin conjugated HBsAg and rabbit anti-biotin-HRP conjugated antibody was used as the secondary antibody complex used for detection. The assay was developed with ortho-phenylenediamine (OPD)

and the absorbance values were determined at 492 nm with background subtraction at 600 nm (Quantum II spectrophotometer, Abbott Labs). Using the specimen absorbance value the corresponding concentration of anti-HBsAg is expressed in milli-international units per ml (mIU/ml) as determined from the standard curve according to parameters established by the manufacturer. For diluted specimens, quantitation was based on the specimen absorbance that resulted in a value between 0-150 mIU/ml, multiplying by the dilution factor to arrive at the final concentration.

Statistical analysis was done with log transformed data by analysis of variance (NCSS97 Statistical Software program, Results from the study are shown in Table 7 below. Administration of oligonucleotides containing an ISS sequence in conjunction with HBsAg resulted in increased titers of anti-HBsAg antibodies as compared to administration of HBsAg alone or to administration of HBsAg with a non-ISS oligonucleotide. In a pairwise comparison, the immune response detected in Group 2 (ISS oligonucleotide) was significantly different from that detected in Group 3 (non-ISS oligonucleotide) ($p<0.05$ post-first immunization, $p=0.06$ post-third immunization). In pairwise comparisons with Group 2, significant differences in the immune responses were not found between that of Group 2 and that found with the other groups receiving an ISS oligonucleotide (Group 4, Group 5, Group 6 and Group 7).

TABLE 7

Anti-HBsAg in bleed samples after immunization

| Group | # | Post-First Immunization mIU/ml | Mean ± SD | Post-second Immunization mIU/ml | Mean ± SD | Post-Third Immunization mIU/ml | Mean ± SD |
|---|---|---|---|---|---|---|---|
| 1 | 1 | 0 | 59 ± 58 | 0 | 806 ± 1229 | 0 | 4245 ± 5673 |
| HBsAg | 2 | 135 | | died | | died | |
| | 3 | 59 | | 613 | | 12,075 | |
| | 4 | 6 | | 2598 | | 4773 | |
| | 5 | 94 | | 12 | | 131 | |
| 2 | 6 | 9 | 108 ± 216 | 357 | 2181 ± 3526 | 1273 | 14,773* ± 15,522 |
| HBsAg + | 7 | 0 | | 1829 | | 6186 | |
| SEQ ID | 8 | 28 | | 158 | | 11,304 | |
| NO: 59 | 9 | 495 | | 8366 | | 41,138 | |
| | 10 | 11 | | 195 | | 13,966 | |
| 3 | 11 | 1 | 1** ± 1 | 2133 | 524 ± 903 | 23,744 | 5529 ± 10,235 |
| HBsAg + | 12 | 0 | | 21 | | 5 | |
| SEQ ID | 13 | 3 | | 202 | | 520 | |
| NO: 60 | 14 | 0 | | 85 | | 647 | |
| | 15 | 0 | | 178 | | 2732 | |
| 4 | 16 | 29 | 25 ± 23 | 333 | 1546 ± 1131 | 4893 | 12,346** ± 6728 |
| HBsAg + | 17 | 50 | | 3281 | | 15,363 | |
| SEQ ID | 18 | 43 | | 1556 | | 22,069 | |
| NO: 38 | 19 | 4 | | 781 | | 7716 | |
| | 20 | 0 | | 1779 | | 11,690 | |
| 5 | 21 | 8 | 26 ± 51 | 6256 | 4556 ± 6943 | 50,538 | 27,726 ± 38,365 |
| HBsAg + | 22 | 116 | | 16,043 | | 84,681 | |
| SEQ ID | 23 | 1 | | 280 | | 750 | |
| NO: 2 | 24 | 0 | | 107 | | 316 | |
| | 25 | 4 | | 93 | | 2346 | |
| 6 | 26 | 21 | 58 ± 93 | 563 | 2804** ± 2515 | 24,100 | 36,904** ± 35,121 |
| HBsAg + | 27 | 4 | | 169 | | 280 | |
| SEQ ID | 28 | 3 | | 6319 | | 23,981 | |
| NO: 18 | 29 | 39 | | 3318 | | 93,750 | |
| | 30 | 221 | | 3652 | | 42413 | |
| 7 | 31 | 5 | 3** ± 2 | 14,190 | 3411 ± 6059 | 3336 | 13,647 ± 14,392 |
| HBsAg + | 32 | 4 | | 438 | | 6926 | |
| SEQ ID | 33 | 3 | | 4 | | 193 | |
| NO: 35 | 34 | 0 | | 687 | | 24,938 | |
| | 35 | 1 | | 1735 | | 32,844 | |

Pairwise comparison to HBsAg alone (group 1)
**$p < 0.05$;
*$p = 0.05$

Kaysville, Utah) using One-Way ANOVA Planned Comparison ($\alpha=0.05$). $p<0.05$ was considered significant.

The animal groups tested were immunized as follows:
Group 1—20 µg HBsAg;
Group 2—20 µg HBsAg+1000 µg SEQ ID NO: 59 (ISS);
Group 3—20 µg HBsAg+1000 µg SEQ ID NO: 60 (non-ISS);
Group 4—20 µg HBsAg+1000 µg SEQ ID NO: 38 (ISS);
Group 5—20 µg HBsAg+1000 µg SEQ ID NO: 2 (ISS);
Group 6—20 µg HBsAg+1000 µg SEQ ID NO: 18 (ISS);
Group 7—20 µg HBsAg+1000 µg SEQ ID NO: 35 (ISS);

Example 4

Preparation of Biodegradable, Cationic Microspheres

Cationic poly(lactic acid, glycolic acid) (PLGA) microspheres were prepared as follows. 0.875 g of poly(D,L-lactide-co-glycolide) 50:50 polymer with an intrinsic viscosity of 0.41 dl/g (0.1%, chloroform, 25° C.) was dissolved in 7.875 g of methylene chloride at 10% w/w concentration, along with 0.3 g of DOTAP. The clear organic phase was then emulsified into 500 ml of polyvinyl alcohol (PVA) aqueous solution (0.35% w/v) by homogenization at 4000 rpm for 30 minutes at room temperature using a laboratory mixer (Silverson L4R, Silverson Instruments). System temperature was then raised to 40° C. by circulating hot water through the jacket of the mixing vessel. Simultaneously, the stirring rate was reduced to 1500 rpm, and these conditions were maintained for 2 hours to extract and evaporate methylene chloride. The microsphere suspension was allowed to cool down to room temperature with the help of circulating cold water.

Microparticles were separated by centrifugation at 8000 rpm for 10 minutes at room temperature (Beckman Instruments) and resuspended in deionized water by gentle bath sonication. The centrifugal wash was repeated two additional times to remove excess PVA from the particle surface. Final centrifugal pellets of particles were suspended in approximately 10 ml of water, and lyophilized overnight. Dried cationic microsphere powder was characterized for size and surface charge: mean size (number weighted, μ)=1.4; zeta potential (mV)=32.4.

assay was performed as described in Example 2. Cationic PLGA microspheres were prepared as described in Example 4. Polynucleotides were tested as single agents, or in combination with cPLGA microspheres. The polynucleotides tested were SEQ ID NOs: 59, 60, 1, and 132. All polynucleotides contained 100% phosphorothioate linkages and were tested at a concentration of 20 μg/ml. The cPLGA was added at a concentration of 100 μg/ml. When the polynucleotides were tested with cPLGA, the polynucleotide and cPLGA were premixed for 15 min. at room temperature and then added to the culture. SAC (PANSORBIN® CalBiochem, 1/5000 dilution) and IMP (ISS-containing), SEQ ID NO: 59, were used as positive controls, and control polynucleotide, SEQ ID NO: 60, and cells alone were used as negative controls. Cationic PLGA was also tested alone. SAC contains *Staph. Aureus* (Cowan I) cell material. Samples were assayed in four healthy donors per assay.

As shown in Table 8 below, polynucleotides containing ISS (IMPs), SEQ ID NOs: 59, 1, and 132, were able to induce IFN-γ and IFN-α when used alone. Complexation of these IMPs with cPGLA cationic microcarriers (cat MC) significantly enhanced the induction of both cytokines. The control polynucleotide, SEQ ID NO: 60 did not induce either IFN-γ or IFN-α when used alone or when complexed with cPLGA.

TABLE 8

| Sample | IFN-γ (pg/ml) | | | | | IFN-α (pg/ml) | | | | |
| --- | --- | --- | --- | --- | --- | --- | --- | --- | --- | --- |
| | Ex 1 | Ex 2 | Ex 3 | Ex 4 | mean | Ex 1 | Ex 2 | Ex 3 | Ex 4 | mean |
| SEQ ID NO: 59 | 324 | 1036 | 529 | 653 | 636 | 9 | 43 | 22 | 108 | 43 |
| SEQ ID NO: 60 | 430 | 19 | 48 | 35 | 34 | 0 | 0 | 4 | 54 | 15 |
| SEQ ID NO: 1 | 287 | 278 | 2679 | 1057 | 1075 | 230 | 268 | 295 | 798 | 398 |
| cat MC | 9 | 5 | 59 | 72 | 36 | 7 | 0 | 98 | 112 | 54 |
| SEQ ID NO: 59/cat MC | 601 | 358 | 1474 | 1941 | 1093 | 115 | 116 | 515 | 1298 | 511 |
| SEQ ID NO: 60/cat MC | 13 | 13 | 46 | 65 | 34 | 5 | 0 | 0 | 43 | 12 |
| SEQ ID NO: 1/cat MC | 1645 | 770 | 3322 | 3355 | 2273 | 1896 | 1078 | 2691 | 1728 | 1848 |
| cells alone | 11 | 4 | 0 | 13 | 7 | 8 | 2 | 3 | 64 | 19 |
| SEQ ID NO: 59 | 1508 | 344 | 144 | 104 | 525 | 50 | 172 | 234 | 72 | 132 |
| SEQ ID NO: 60 | 124 | 24 | 16 | 40 | 51 | 2 | 32 | 474 | 2 | 128 |
| SEQ ID NO: 132 | 2928 | 936 | 380 | 108 | 1088 | 4968 | 72 | 1290 | 1182 | 1878 |
| cat MC | 32 | 8 | 72 | 120 | 58 | 10 | 2 | 60 | 92 | 41 |
| SEQ ID NO: 59/cat MC | 1640 | 968 | 960 | 2300 | 1467 | 948 | 260 | 1298 | 1470 | 994 |
| SEQ ID NO: 60/cat MC | 72 | 16 | 32 | 316 | 109 | 14 | 14 | 22 | 2 | 13 |
| SEQ ID NO: 132/cat MC | 1060 | 4584 | 5172 | 1188 | 3001 | 5292 | 1050 | 3772 | 3214 | 3332 |
| cells alone | 44 | 24 | 20 | 28 | 29 | 20 | 200 | 2 | 2 | 56 |

Example 5

Immunomodulation with IMP/MC Complexes in Human Cells

Polynucleotides were tested for immunomodulatory activity alone and complexed with cationic PLGA microspheres (cPLGA) in the human PBMC assay. The human PBMC Although the foregoing invention has been described in some detail by way of illustration and example for purposes of clarity and understanding, it will be apparent to those skilled in the art that certain changes and modifications may be practiced. Therefore, descriptions and examples should not be construed as limiting the scope of the invention, which is delineated by the appended claims.

What is claimed is:

1. A method of increasing interferon-gamma (IFN-γ) in an individual, comprising: administering a pharmaceutical composition comprising an immunostimulatory sequence (ISS) comprising CGAACGTTCG (SEQ ID NO: 77) and a pharmaceutically acceptable excipient to said individual in an amount sufficient to increase IFN-γ in said individual.

2. A method of increasing interferon-alpha (IFN-α) in an individual, comprising: administering a pharmaceutical composition comprising an immunostimulatory sequence (ISS) comprising CGAACGTTCG (SEQ ID NO: 77) and a pharmaceutically acceptable excipient to said individual in an amount sufficient to increase IFN-α in said individual.

3. The method according to claim 1 or 2, wherein the ISS further comprises at least one TCG sequence.

4. The composition according to claim 1 or 2, wherein the ISS further comprises a TCG sequence that is separated from the 5' end of the ISS by one base.

5. The composition according to claim 1 or 2, wherein the ISS further comprises a T sequence that is 5' to the ISS.

6. The composition according to claim 3, wherein the TCG sequence is at the 5'-end of the ISS.

7. The composition according to claim 1 or 2, wherein the ISS comprising CGAACGTTCG (SEQ ID NO: 77) is selected from the group consisting of SEQ ID NO: 1, 11, 14, 19, 22, 28, 30, 97, 98, 102 and 132.

8. The method of claim 1 or 2, wherein said individual suffers from a disorder associated with a Th2-type immune response.

9. The method of claim 1 or 2, wherein said individual suffers from allergy.

10. The method of claim 1 or 2, wherein said individual suffers from asthma.

11. The method of claim 1 or 2, wherein said individual has an infectious disease.

12. The method of claim 11, wherein said infectious disease is an infectious disease caused by a cellular pathogen.

13. The method of claim 12, wherein said infectious disease caused by a cellular pathogen is selected from the group consisting of mycobacterial disease, malaria, leishmaniasis, toxoplasmosis, schistosomiasis and clonorchiasis.

14. The method of claim 1 or 2, wherein said individual has a viral infection.

15. The method of claim 14 wherein the viral infection is selected from the group consisting of influenza virus, respiratory syncytial virus (RSV), hepatitis virus B, hepatitis virus C, herpes viruses, particularly herpes simplex viruses, and papilloma viruses.

16. The method of claim 1 or 2, wherein said individual has a parasitic infection.

17. The method of claim 16, wherein the parasitic infection is selected from the group consisting of malaria, leishmaniasis, toxoplasmosis, schistosomiasis, and clonorchiasis.

18. The method of claim 1 or 2, wherein said individual has an inflammatory disorder.

19. The method of claim 1 or 2, wherein said individual has cancer or tumors.

20. The method of claim 1 or 2 wherein said individual is a human.

21. The method of claim 9 wherein said individual is a human.

22. The method of claim 10 wherein said individual is a human.

* * * * *

UNITED STATES PATENT AND TRADEMARK OFFICE
CERTIFICATE OF CORRECTION

PATENT NO. : 8,372,413 B2
APPLICATION NO. : 11/963663
DATED : February 12, 2013
INVENTOR(S) : Karen L. Fearon et al.

It is certified that error appears in the above-identified patent and that said Letters Patent is hereby corrected as shown below:

ON THE TITLE PAGE, ITEM (56) OTHER PUBLICATIONS:

Page two Column 2, line 19, please replace "Administation" with --Administration--

Page two Column 2, line 39, please replace "*P NAS*" with --*PNAS*--

Page three Column 1, line 11, please replace "Sulphydryl" with --Sulfhydryl--

Page three Column 1, line 46, please replace "Contens)" with --Contents).--

Page five Column 1, line 11, please replace "Non-Nucleotied-Based" with --Non-Nucleotide-Based--

Page five Column 1, line 15, please replace "Practioners" with --Practitioners--

Page five Column 2, line 3, please replace "53:93-" with --53(45S):93- --

IN THE SPECIFICATION:

Column 8, line 4-5, please replace "Hemophilus influenza" with --Haemophilus influenzae--

Column 9, line 41, please replace "speherical" with --spherical--

Column 9, line 52, please replace "erodable" with --erodible--

Column 20, line 37, please replace "7247" with --7237--

Column 21, line 28, please replace "oxopyrolo" with --oxopyrrolo--

Column 22, line 63, please replace "Protein" with --protein--

Signed and Sealed this
Twenty-fourth Day of June, 2014

Michelle K. Lee
*Deputy Director of the United States Patent and Trademark Office*

Column 22, line 64, please replace "Antigens" with --antigens--

Column 22, line 64, please replace "Grass" with --grass--

Column 22, line 64, please replace "Pollen" with --pollen--

Column 22, line 64, please replace "Administration" with --administration--

Column 22, line 64, please replace "In Vivo" with --in vivo--

Column 22, line 65, please replace "Reported" with --reported--

Column 24, line 1, please replace "β-lactoglobin" with --β-lactoglobulin--

Column 24, line 67 (TABLE 1), please replace "Dermatis," with --Dermatitis,--

Column 24, line 68 (TABLE 1), please replace "topomyosin" with --tropomyosin--

Column 25, line 57 (TABLE 1), please replace "Penicillinium" with --Penicillium--

Column 25, line 57, please replace "Hemophilus influenza," with --Haemophilus influenzae,--

Column 25, line 60, please replace "*species*" with --species--

Column 27, line 24, please replace "Viruses" with --viruses--

Column 27, line 24, please replace "Well-" with --well- --

Column 27, line 25, please replace "Known" with --known--

Column 27, line 25, please replace "Art" with --art--

Column 27, line 25, please replace "Many" with --many--

Column 27, line 25, please replace "Commercially" with --commercially--

Column 27, line 25, please replace "Available" with --available--

Column 31, line 64, please replace "inter alia" with --*inter alia*--

Column 32, line 64, please replace "tetraminobenzene," with --tetraaminobenzene,--

Column 32, line 64-65, please replace "heptaminobetacyclodextrin," with --heptaaminobetacyclodextrin,--

CERTIFICATE OF CORRECTION (continued)
U.S. Pat. No. 8,372,413 B2

Column 32, line 65, please replace "tetraminopentaerythritol," with --tetraaminopentaerythritol,--

Column 33, line 43, please replace "$(CH_2CH_2O)_n CH_2CH_2—O—(CH_2)_m CO_2R^2$" with --$(CH_2CH_2O)_n CH_2CH_2O(CH_2)_m CO_2R^2$--

Column 33, line 47, please replace "haloaceyl," with --haloacetyl,--

Column 33, line 47, please replace "maleiamide," with --maleimide,--

Column 34, line 40-51, please replace "polyisohexlcyanoacrylate" with --polyisohexylcyanoacrylate--

Column 36, line 1, please replace "polyvinylpirrolidone" with --polyvinylpyrrolidone--

Column 42, line 45, please replace "decease" with --decrease--

Column 45, line 42, please replace "Swiftwater, Pa." with --Swiftwater, PA--

Column 57, line 56, please replace "Kaysville, Utah" with --Kaysville, UT--

Column 58, line 66, please replace "(0.1%, chloroform, 25° C.)" with --(0.1%, chloroform, 25° C)--

Column 59, line 6, please replace "40° C." with --40° C--

SEQUENCE LISTING

<160> NUMBER OF SEQ ID NOS: 133

<210> SEQ ID NO 1
<211> LENGTH: 24
<212> TYPE: DNA
<213> ORGANISM: Artificial Sequence
<220> FEATURE:
<223> OTHER INFORMATION: Polynucleotide containing CG

<400> SEQUENCE: 1
tcgtcgaacg ttcgttaacg ttcg                                          24

<210> SEQ ID NO 2
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 2
tgactgtgaa cgutcgagat ga                                            22

<210> SEQ ID NO 3
<211> LENGTH: 24
<212> TYPE: DNA
<213> ORGANISM: Artificial Sequence
<220> FEATURE:
<223> OTHER INFORMATION: Polynucleotide containing CG

<400> SEQUENCE: 3
tcgtcgaucg utcgttaacg utcg                                          24

<210> SEQ ID NO 4
<211> LENGTH: 24
<212> TYPE: DNA
<213> ORGANISM: Artificial Sequence
<220> FEATURE:
<223> OTHER INFORMATION: Polynucleotide containing CG

<400> SEQUENCE: 4
tcgtcgaucg ttcgtuaacg utcg                                          24

<210> SEQ ID NO 5
<211> LENGTH: 24
<212> TYPE: DNA
<213> ORGANISM: Artificial Sequence
<220> FEATURE:
<223> OTHER INFORMATION: Polynucleotide containing CG

<400> SEQUENCE: 5
tcgtcguacg utcgttaacg utcg                                          24

<210> SEQ ID NO 6
<211> LENGTH: 24
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 8
<223> OTHER INFORMATION: n = 2-amino-adenine

<400> SEQUENCE: 6
tcgtcgancg utcgttaacg utcg                                          24

```
<210> SEQ ID NO 7
<211> LENGTH: 24
<212> TYPE: DNA
<213> ORGANISM: Artificial Sequence
<220> FEATURE:
<223> OTHER INFORMATION: Polynucleotide containing CG

<400> SEQUENCE: 7
tgatcgaacg ttcgttaacg ttcg                                              24

<210> SEQ ID NO 8
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 8
tgactgtgaa cgutcggtat ga                                                22

<210> SEQ ID NO 9
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 9
tgactgtgac cgttcggtat ga                                                22

<210> SEQ ID NO 10
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 10
tgactgtgat cggtcggtat ga                                                22

<210> SEQ ID NO 11
<211> LENGTH: 16
<212> TYPE: DNA
<213> ORGANISM: Artificial Sequence
<220> FEATURE:
<223> OTHER INFORMATION: Polynucleotide containing CG

<400> SEQUENCE: 11
tcgtcgaacg ttcgtt                                                       16

<210> SEQ ID NO 12
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 12
tcgtcgtgaa cgttcgagat ga                                                22

<210> SEQ ID NO 13
<211> LENGTH: 22
<212> TYPE: DNA
<213> ORGANISM: Artificial Sequence
<220> FEATURE:
<223> OTHER INFORMATION: Polynucleotide containing CG
```

```
<400> SEQUENCE: 13
tcgtcggtat cggtcggtat ga                                           22

<210> SEQ ID NO 14
<211> LENGTH: 18
<212> TYPE: DNA
<213> ORGANISM: Artificial Sequence
<220> FEATURE:
<223> OTHER INFORMATION: Polynucleotide containing CG

<400> SEQUENCE: 14
cttcgaacgt tcgagatg                                                18

<210> SEQ ID NO 15
<211> LENGTH: 18
<212> TYPE: DNA
<213> ORGANISM: Artificial Sequence
<220> FEATURE:
<223> OTHER INFORMATION: Polynucleotide containing CG

<400> SEQUENCE: 15
ctgtgatcgt tcgagatg                                                18

<210> SEQ ID NO 16
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 16
tgactgtgaa cggtcggtat ga                                           22

<210> SEQ ID NO 17
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 17
tcgtcggtac cgttcggtat ga                                           22

<210> SEQ ID NO 18
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 18
tcgtcggaac cgttcggaat ga                                           22

<210> SEQ ID NO 19
<211> LENGTH: 19
<212> TYPE: DNA
<213> ORGANISM: Artificial Sequence
<220> FEATURE:
<223> OTHER INFORMATION: Polynucleotide containing CG

<400> SEQUENCE: 19
tcgtcgaacg ttcgagatg                                               19

<210> SEQ ID NO 20
<211> LENGTH: 20
<212> TYPE: DNA
```

<213> ORGANISM: Artificial Sequence
<220> FEATURE:
<223> OTHER INFORMATION: Polynucleotide containing CG

<400> SEQUENCE: 20
tcgtcgtaac gttcgagatg                               20

<210> SEQ ID NO 21
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 21
tgactgtgac cgttcggaat ga                            22

<210> SEQ ID NO 22
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 22
tcgtcgaacg ttcgaacgtt cg                            22

<210> SEQ ID NO 23
<211> LENGTH: 19
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 2, 5
<223> OTHER INFORMATION: n = 5-bromocytocine

<400> SEQUENCE: 23
tngtngaacg ttcgagatg                                19

<210> SEQ ID NO 24
<211> LENGTH: 19
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 5
<223> OTHER INFORMATION: n = 5-bromocytosine

<400> SEQUENCE: 24
tcgtngaacg ttcgagatg                                19

<210> SEQ ID NO 25
<211> LENGTH: 20
<212> TYPE: DNA
<213> ORGANISM: Artificial Sequence
<220> FEATURE:
<223> OTHER INFORMATION: Polynucleotide containing CG

<400> SEQUENCE: 25
tcgtcgaccg ttcggaatga                               20

<210> SEQ ID NO 26
<211> LENGTH: 20
<212> TYPE: DNA

<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 2, 5
<223> OTHER INFORMATION: n = 5-bromocytosine

<400> SEQUENCE: 26
tngtngaccg ttcggaatga                                       20

<210> SEQ ID NO 27
<211> LENGTH: 20
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 5
<223> OTHER INFORMATION: n = 5-bromocytosine

<400> SEQUENCE: 27
tcgtngaccg ttcggaatga                                       20

<210> SEQ ID NO 28
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 28
ttcgaacgtt cgttaacgtt cg                                    22

<210> SEQ ID NO 29
<211> LENGTH: 18
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 4
<223> OTHER INFORMATION: n = 5-bromocytosine

<400> SEQUENCE: 29
cttngaacgt tcgagatg                                         18

<210> SEQ ID NO 30
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 30
tgatcgtcga acgttcgaga tg                                    22

<210> SEQ ID NO 31
<211> LENGTH: 22
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 11
<223> OTHER INFORMATION: n = 5-bromocytosine

```
<400> SEQUENCE: 31
tgactgtgaa ngutcgagat ga                                            22

<210> SEQ ID NO 32
<211> LENGTH: 24
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 9, 19
<223> OTHER INFORMATION: n = 5-bromocytosine

<400> SEQUENCE: 32
tcgtcgaang ttcgttaang ttcg                                          24

<210> SEQ ID NO 33
<211> LENGTH: 22
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 11
<223> OTHER INFORMATION: n = 5-bromocytosine

<400> SEQUENCE: 33
tgactgtgaa ngutcggtat ga                                            22

<210> SEQ ID NO 34
<211> LENGTH: 22
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 11
<223> OTHER INFORMATION: n = 5-bromocytosine

<400> SEQUENCE: 34
tgactgtgaa ngutcggaat ga                                            22

<210> SEQ ID NO 35
<211> LENGTH: 22
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 11
<223> OTHER INFORMATION: n = 5-bromocytosine

<400> SEQUENCE: 35
tcgtcggaaa ngutcggaat ga                                            22

<210> SEQ ID NO 36
<211> LENGTH: 20
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 5, 9
<223> OTHER INFORMATION: n = 5-bromocytosine
```

```
<400> SEQUENCE: 36
tcgtngaang utcggaatga                                          20

<210> SEQ ID NO 37
<211> LENGTH: 22
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 11
<223> OTHER INFORMATION: n = 5-bromocytosine

<400> SEQUENCE: 37
tgactgtgaa ngttcgagat ga                                       22

<210> SEQ ID NO 38
<211> LENGTH: 22
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 11, 15
<223> OTHER INFORMATION: n = 5-bromocytosine

<400> SEQUENCE: 38
tgactgtgaa ngttngagat ga                                       22

<210> SEQ ID NO 39
<211> LENGTH: 22
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 11
<223> OTHER INFORMATION: n = 5-bromocytosine

<400> SEQUENCE: 39
tgactgtgaa ngttccagat ga                                       22

<210> SEQ ID NO 40
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 40
tgactgtgaa cgtucgagat ga                                       22

<210> SEQ ID NO 41
<211> LENGTH: 22
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 13
<223> OTHER INFORMATION: n = 5-bromouracil

<400> SEQUENCE: 41
tgactgtgaa cgntcgagat ga                                       22
```

```
<210> SEQ ID NO 42
<211> LENGTH: 22
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 11
<223> OTHER INFORMATION: n = 5-bromocytosine

<400> SEQUENCE: 42
tgactgtgaa ngttcgtuat ga                                              22

<210> SEQ ID NO 43
<211> LENGTH: 22
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 11
<223> OTHER INFORMATION: n = 5-bromocytosine

<400> SEQUENCE: 43
tgactgtgaa ngttcggtat ga                                              22

<210> SEQ ID NO 44
<211> LENGTH: 18
<212> TYPE: DNA
<213> ORGANISM: Artificial Sequence
<220> FEATURE:
<223> OTHER INFORMATION: Polynucleotide containing CG

<400> SEQUENCE: 44
ctgtgaacgt tcgagatg                                                   18

<210> SEQ ID NO 45
<211> LENGTH: 22
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 2, 5
<223> OTHER INFORMATION: n = 5-bromocytosine

<400> SEQUENCE: 45
tngtngtgaa cgttcgagat ga                                              22

<210> SEQ ID NO 46
<211> LENGTH: 22
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 5
<223> OTHER INFORMATION: n = 5-bromocytosine

<400> SEQUENCE: 46
tcgtngtgaa cgttcgagat ga                                              22

<210> SEQ ID NO 47
<211> LENGTH: 22
<212> TYPE: DNA
```

```
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 13
<223> OTHER INFORMATION: n = 4-thio-thymine

<400> SEQUENCE: 47
tgactgtgaa cgntcgagat ga                                              22

<210> SEQ ID NO 48
<211> LENGTH: 22
<212> TYPE: DNA
<213> ORGANISM: Artificial Sequence
<220> FEATURE:
<223> OTHER INFORMATION: Polynucleotide containing C(6-thio-guanine)
<220> FEATURE:
<221> NAME/KEY: misc_feature
<222> LOCATION: 12, 16
<223> OTHER INFORMATION: n = 6-thio-guanine

<400> SEQUENCE: 48
tgactgtgaa cnttcnagat ga                                              22

<210> SEQ ID NO 49
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 49
tgactgtgaa cgttcgtuat ga                                              22

<210> SEQ ID NO 50
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 50
tgactgtgaa cgttcgttat ga                                              22

<210> SEQ ID NO 51
<211> LENGTH: 24
<212> TYPE: DNA
<213> ORGANISM: Artificial Sequence
<220> FEATURE:
<223> OTHER INFORMATION: Polynucleotide containing CG

<400> SEQUENCE: 51
tcgttcaacg ttcgttaacg ttcg                                            24

<210> SEQ ID NO 52
<211> LENGTH: 24
<212> TYPE: DNA
<213> ORGANISM: Artificial Sequence
<220> FEATURE:
<223> OTHER INFORMATION: Polynucleotide containing CG

<400> SEQUENCE: 52
tgattcaacg ttcgttaacg ttcg                                            24

<210> SEQ ID NO 53
<211> LENGTH: 18
<212> TYPE: DNA
```

```
<213> ORGANISM: Artificial Sequence
<220> FEATURE:
<223> OTHER INFORMATION: Polynucleotide containing CG

<400> SEQUENCE: 53
ctgtcaacgt tcgagatg                                                 18

<210> SEQ ID NO 54
<211> LENGTH: 14
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 2, 5
<223> OTHER INFORMATION: n = 5-bromocytosine

<400> SEQUENCE: 54
tnctncaccg ttcg                                                     14

<210> SEQ ID NO 55
<211> LENGTH: 20
<212> TYPE: DNA
<213> ORGANISM: Artificial Sequence
<220> FEATURE:
<223> OTHER INFORMATION: Polynucleotide containing CG

<400> SEQUENCE: 55
tcgtcggaac gttcgagatg                                               20

<210> SEQ ID NO 56
<211> LENGTH: 19
<212> TYPE: DNA
<213> ORGANISM: Artificial Sequence
<220> FEATURE:
<223> OTHER INFORMATION: Polynucleotide containing CG

<400> SEQUENCE: 56
tcgtcggacg ttcgagatg                                                19

<210> SEQ ID NO 57
<211> LENGTH: 19
<212> TYPE: DNA
<213> ORGANISM: Artificial Sequence
<220> FEATURE:
<223> OTHER INFORMATION: Polynucleotide containing CG

<400> SEQUENCE: 57
tcgtcgtacg ttcgagatg                                                19

<210> SEQ ID NO 58
<211> LENGTH: 19
<212> TYPE: DNA
<213> ORGANISM: Artificial Sequence
<220> FEATURE:
<223> OTHER INFORMATION: Polynucleotide containing CG

<400> SEQUENCE: 58
tcgtcgttcg ttcgagatg                                                19

<210> SEQ ID NO 59
<211> LENGTH: 22
<212> TYPE: DNA
<213> ORGANISM: Artificial Sequence
<220> FEATURE:
<223> OTHER INFORMATION: Polynucleotide containing CG
```

```
<400> SEQUENCE: 59
tgactgtgaa cgttcgagat ga                                              22

<210> SEQ ID NO 60
<211> LENGTH: 22
<212> TYPE: DNA
<213> ORGANISM: Artificial Sequence
<220> FEATURE:
<223> OTHER INFORMATION: Polynucleotide not containing CG

<400> SEQUENCE: 60
tgactgtgaa ccttagagat ga                                              22

<210> SEQ ID NO 61
<211> LENGTH: 22
<212> TYPE: DNA
<213> ORGANISM: Artificial Sequence
<220> FEATURE:
<223> OTHER INFORMATION: Polynucleotide not containing CG

<400> SEQUENCE: 61
tgactgtgaa ggttagagat ga                                              22

<210> SEQ ID NO 62
<211> LENGTH: 10
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 1
<223> OTHER INFORMATION: n= t, g, c, or 5-bromocytosine
<220> FEATURE:
<221> NAME/KEY: misc_feature
<222> LOCATION: 4
<223> OTHER INFORMATION: n= t or m

<400> SEQUENCE: 62 ndancgktcg                                                            10

<210> SEQ ID NO 63
<211> LENGTH: 10
<212> TYPE: DNA
<213> ORGANISM: Artificial Sequence
<220> FEATURE:
<223> OTHER INFORMATION: Polynucleotide containing CG

<400> SEQUENCE: 63
tgaacgttcg                                                            10

<210> SEQ ID NO 64
<211> LENGTH: 10
<212> TYPE: DNA
<213> ORGANISM: Artificial Sequence
<220> FEATURE:
<223> OTHER INFORMATION: Polynucleotide containing CG

<400> SEQUENCE: 64
ggaacgttcg                                                            10

<210> SEQ ID NO 65
<211> LENGTH: 10
<212> TYPE: DNA
<213> ORGANISM: Artificial Sequence
<220> FEATURE:
<223> OTHER INFORMATION: Polynucleotide containing (5-bromocystosine)G
<220> FEATURE:
```

```
<221> NAME/KEY: misc_feature
<222> LOCATION: 1
<223> OTHER INFORMATION: n = t, g, c or 5-bromocytosine
<220> FEATURE:
<221> NAME/KEY: misc_feature
<222> LOCATION: 4
<223> OTHER INFORMATION: n = t or m
<220> FEATURE:
<221> NAME/KEY: misc_feature
<222> LOCATION: 5
<223> OTHER INFORMATION: n = 5-bromocytosine

<400> SEQUENCE: 65 ndanngktcg                                                              10

<210> SEQ ID NO 66
<211> LENGTH: 10
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 5
<223> OTHER INFORMATION: n = 5-bromocytosine

<400> SEQUENCE: 66 tgaangttcg                                                              10

<210> SEQ ID NO 67
<211> LENGTH: 10
<212> TYPE: DNA
<213> ORGANISM: Artificial Sequence
<220> FEATURE:
<223> OTHER INFORMATION: Polynucleotide containing CG

<400> SEQUENCE: 67
tgaacgutcg                                                              10

<210> SEQ ID NO 68
<211> LENGTH: 10
<212> TYPE: DNA
<213> ORGANISM: Artificial Sequence
<220> FEATURE:
<223> OTHER INFORMATION: Polynucleotide containing CG

<400> SEQUENCE: 68
tgaccgttcg                                                              10

<210> SEQ ID NO 69
<211> LENGTH: 10
<212> TYPE: DNA
<213> ORGANISM: Artificial Sequence
<220> FEATURE:
<223> OTHER INFORMATION: Polynucleotide containing CG

<400> SEQUENCE: 69
tgatcggtcg                                                              10

<210> SEQ ID NO 70
<211> LENGTH: 10
<212> TYPE: DNA
<213> ORGANISM: Artificial Sequence
<220> FEATURE:
<223> OTHER INFORMATION: Polynucleotide containing CG

<400> SEQUENCE: 70
tgatcgttcg                                                              10
```

```
<210> SEQ ID NO 71
<211> LENGTH: 10
<212> TYPE: DNA
<213> ORGANISM: Artificial Sequence
<220> FEATURE:
<223> OTHER INFORMATION: Polynucleotide containing CG

<400> SEQUENCE: 71
tgaacggtcg                                                          10

<210> SEQ ID NO 72
<211> LENGTH: 10
<212> TYPE: DNA
<213> ORGANISM: Artificial Sequence
<220> FEATURE:
<223> OTHER INFORMATION: Polynucleotide containing CG

<400> SEQUENCE: 72
gtaacgttcg                                                          10

<210> SEQ ID NO 73
<211> LENGTH: 10
<212> TYPE: DNA
<213> ORGANISM: Artificial Sequence
<220> FEATURE:
<223> OTHER INFORMATION: Polynucleotide containing CG

<400> SEQUENCE: 73
gtatcggtcg                                                          10

<210> SEQ ID NO 74
<211> LENGTH: 10
<212> TYPE: DNA
<213> ORGANISM: Artificial Sequence
<220> FEATURE:
<223> OTHER INFORMATION: Polynucleotide containing CG

<400> SEQUENCE: 74
gtaccgttcg                                                          10

<210> SEQ ID NO 75
<211> LENGTH: 10
<212> TYPE: DNA
<213> ORGANISM: Artificial Sequence
<220> FEATURE:
<223> OTHER INFORMATION: Polynucleotide containing CG

<400> SEQUENCE: 75
gaaccgttcg                                                          10

<210> SEQ ID NO 76
<211> LENGTH: 10
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 1
<223> OTHER INFORMATION: n = 5-bromocytosine

<400> SEQUENCE: 76 ngaccgttcg                                                          10

<210> SEQ ID NO 77
<211> LENGTH: 10
<212> TYPE: DNA
```

```
<213> ORGANISM: Artificial Sequence
<220> FEATURE:
<223> OTHER INFORMATION: Polynucleotide containing CG

<400> SEQUENCE: 77
cgaacgttcg                                                          10

<210> SEQ ID NO 78
<211> LENGTH: 10
<212> TYPE: DNA
<213> ORGANISM: Artificial Sequence
<220> FEATURE:
<223> OTHER INFORMATION: Polynucleotide containing CG

<400> SEQUENCE: 78
cgaccgttcg                                                          10

<210> SEQ ID NO 79
<211> LENGTH: 10
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 1
<223> OTHER INFORMATION: n = 5-bromocytosine

<400> SEQUENCE: 79 ngaacgttcg                                                          10

<210> SEQ ID NO 80
<211> LENGTH: 10
<212> TYPE: DNA
<213> ORGANISM: Artificial Sequence
<220> FEATURE:
<223> OTHER INFORMATION: Polynucleotide containing CG

<400> SEQUENCE: 80
ttaacgutcg                                                          10

<210> SEQ ID NO 81
<211> LENGTH: 10
<212> TYPE: DNA
<213> ORGANISM: Artificial Sequence
<220> FEATURE:
<223> OTHER INFORMATION: Polynucleotide containing CG

<400> SEQUENCE: 81
tuaacgutcg                                                          10

<210> SEQ ID NO 82
<211> LENGTH: 10
<212> TYPE: DNA
<213> ORGANISM: Artificial Sequence
<220> FEATURE:
<223> OTHER INFORMATION: Polynucleotide containing CG

<400> SEQUENCE: 82
ttaacgttcg                                                          10

<210> SEQ ID NO 83
<211> LENGTH: 10
<212> TYPE: DNA
<213> ORGANISM: Artificial Sequence
<220> FEATURE:
<223> OTHER INFORMATION: Polynucleotide containing (5-bromocytosine)G
<220> FEATURE:
```

```
<221> NAME/KEY: misc_feature
<222> LOCATION: 5
<223> OTHER INFORMATION: n = 5-bromocytosine

<400> SEQUENCE: 83 tgaangutcg                                                              10

<210> SEQ ID NO 84
<211> LENGTH: 10
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 5
<223> OTHER INFORMATION: n = 5-bromocytosine

<400> SEQUENCE: 84 tgacngttcg                                                              10

<210> SEQ ID NO 85
<211> LENGTH: 10
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 5
<223> OTHER INFORMATION: n = 5-bromocytosine

<400> SEQUENCE: 85 tgatnggtcg                                                              10

<210> SEQ ID NO 86
<211> LENGTH: 10
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 5
<223> OTHER INFORMATION: n = 5-bromocytosine

<400> SEQUENCE: 86 gtatnggtcg                                                              10

<210> SEQ ID NO 87
<211> LENGTH: 10
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 5
<223> OTHER INFORMATION: n = 5-bromocytosine

<400> SEQUENCE: 87 gtacngttcg                                                              10

<210> SEQ ID NO 88
<211> LENGTH: 10
<212> TYPE: DNA
<213> ORGANISM: Artificial Sequence
<220> FEATURE:
<223> OTHER INFORMATION: Polynucleotide containing (5-bromocytosine)G
<220> FEATURE:
```

```
<221> NAME/KEY: misc_feature
<222> LOCATION: 5
<223> OTHER INFORMATION: n = 5-bromocytosine

<400> SEQUENCE: 88 gaacngttcg                                                              10

<210> SEQ ID NO 89
<211> LENGTH: 10
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 5
<223> OTHER INFORMATION: n = 5-bromocytosine

<400> SEQUENCE: 89 gaaangutcg                                                              10

<210> SEQ ID NO 90
<211> LENGTH: 10
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 1, 5
<223> OTHER INFORMATION: n = 5-bromocytosine

<400> SEQUENCE: 90 ngacngttcg                                                              10

<210> SEQ ID NO 91
<211> LENGTH: 10
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 5
<223> OTHER INFORMATION: n = 5-bromocytosine

<400> SEQUENCE: 91 cgaangttcg                                                              10

<210> SEQ ID NO 92
<211> LENGTH: 10
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 1, 5
<223> OTHER INFORMATION: n = 5-bromocytosine

<400> SEQUENCE: 92 ngaangttcg                                                              10

<210> SEQ ID NO 93
<211> LENGTH: 10
<212> TYPE: DNA
<213> ORGANISM: Artificial Sequence
<220> FEATURE:
<223> OTHER INFORMATION: Polynucleotide containing (5-bromocytosine)G
<220> FEATURE:
```

```
<221> NAME/KEY: misc_feature
<222> LOCATION: 1, 5
<223> OTHER INFORMATION: n = 5-bromocytosine

<400> SEQUENCE: 93 ngaangutcg                                                              10

<210> SEQ ID NO 94
<211> LENGTH: 10
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 5
<223> OTHER INFORMATION: n = 5-bromocytosine

<400> SEQUENCE: 94 ttaangutcg                                                              10

<210> SEQ ID NO 95
<211> LENGTH: 10
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 5
<223> OTHER INFORMATION: n = 5-bromocytosine

<400> SEQUENCE: 95 tuaangutcg                                                              10

<210> SEQ ID NO 96
<211> LENGTH: 10
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 5
<223> OTHER INFORMATION: n = 5-bromocytosine

<400> SEQUENCE: 96 ttaangttcg                                                              10

<210> SEQ ID NO 97
<211> LENGTH: 13
<212> TYPE: DNA
<213> ORGANISM: Artificial Sequence
<220> FEATURE:
<223> OTHER INFORMATION: Polynucleotide containing CG

<400> SEQUENCE: 97
tcgcgaacgt tcg                                                          13

<210> SEQ ID NO 98
<211> LENGTH: 14
<212> TYPE: DNA
<213> ORGANISM: Artificial Sequence
<220> FEATURE:
<223> OTHER INFORMATION: Polynucleotide containing CG

<400> SEQUENCE: 98
tcgtcgaacg ttcg                                                         14
```

```
<210> SEQ ID NO 99
<211> LENGTH: 13
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 2
<223> OTHER INFORMATION: n = 5-bromocytosine

<400> SEQUENCE: 99
tngcgaacgt tcg                                                          13

<210> SEQ ID NO 100
<211> LENGTH: 14
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 2, 5
<223> OTHER INFORMATION: n = 5-bromocytosine

<400> SEQUENCE: 100
tngtngaacg ttcg                                                         14

<210> SEQ ID NO 101
<211> LENGTH: 13
<212> TYPE: DNA
<213> ORGANISM: Artificial Sequence
<220> FEATURE:
<223> OTHER INFORMATION: Polynucleotide containing CG

<400> SEQUENCE: 101
tcgttaacgt tcg                                                          13

<210> SEQ ID NO 102
<211> LENGTH: 11
<212> TYPE: DNA
<213> ORGANISM: Artificial Sequence
<220> FEATURE:
<223> OTHER INFORMATION: Polynucleotide containing CG

<400> SEQUENCE: 102
tcgaacgttc g                                                            11

<210> SEQ ID NO 103
<211> LENGTH: 13
<212> TYPE: DNA
<213> ORGANISM: Artificial Sequence
<220> FEATURE:
<223> OTHER INFORMATION: Polynucleotide containing CG

<400> SEQUENCE: 103
tcgtgaacgt tcg                                                          13

<210> SEQ ID NO 104
<211> LENGTH: 13
<212> TYPE: DNA
<213> ORGANISM: Artificial Sequence
<220> FEATURE:
<223> OTHER INFORMATION: Polynucleotide containing CG

<400> SEQUENCE: 104
tcggtatcgg tcg                                                          13
```

```
<210> SEQ ID NO 105
<211> LENGTH: 13
<212> TYPE: DNA
<213> ORGANISM: Artificial Sequence
<220> FEATURE:
<223> OTHER INFORMATION: Polynucleotide containing CG

<400> SEQUENCE: 105
tcggtaccgt tcg                                                          13

<210> SEQ ID NO 106
<211> LENGTH: 13
<212> TYPE: DNA
<213> ORGANISM: Artificial Sequence
<220> FEATURE:
<223> OTHER INFORMATION: Polynucleotide containing CG

<400> SEQUENCE: 106
tcggaaccgt tcg                                                          13

<210> SEQ ID NO 107
<211> LENGTH: 12
<212> TYPE: DNA
<213> ORGANISM: Artificial Sequence
<220> FEATURE:
<223> OTHER INFORMATION: Polynucleotide containing CG

<400> SEQUENCE: 107
tcggaacgtt cg                                                           12

<210> SEQ ID NO 108
<211> LENGTH: 15
<212> TYPE: DNA
<213> ORGANISM: Artificial Sequence
<220> FEATURE:
<223> OTHER INFORMATION: Polynucleotide containing CG

<400> SEQUENCE: 108
tcgtcggaac gttcg                                                        15

<210> SEQ ID NO 109
<211> LENGTH: 12
<212> TYPE: DNA
<213> ORGANISM: Artificial Sequence
<220> FEATURE:
<223> OTHER INFORMATION: Polynucleotide containing CG

<400> SEQUENCE: 109
tcgtaacgtt cg                                                           12

<210> SEQ ID NO 110
<211> LENGTH: 11
<212> TYPE: DNA
<213> ORGANISM: Artificial Sequence
<220> FEATURE:
<223> OTHER INFORMATION: Polynucleotide containing CG

<400> SEQUENCE: 110
tcgaccgttc g                                                            11

<210> SEQ ID NO 111
<211> LENGTH: 14
<212> TYPE: DNA
<213> ORGANISM: Artificial Sequence
<220> FEATURE:
<223> OTHER INFORMATION: Polynucleotide containing CG
```

<400> SEQUENCE: 111
tcgtcgaccg ttcg                                                         14

<210> SEQ ID NO 112
<211> LENGTH: 13
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 2
<223> OTHER INFORMATION: n = 5-bromocytosine

<400> SEQUENCE: 112
tnctgaacgt tcg                                                          13

<210> SEQ ID NO 113
<211> LENGTH: 16
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 2, 5
<223> OTHER INFORMATION: n = 5-bromocytosine

<400> SEQUENCE: 113
tnctnctgaa cgttcg                                                       16

<210> SEQ ID NO 114
<211> LENGTH: 11
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 2
<223> OTHER INFORMATION: n = 5-bromocytosine

<400> SEQUENCE: 114
tncaacgttc g                                                            11

<210> SEQ ID NO 115
<211> LENGTH: 14
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 2, 5
<223> OTHER INFORMATION: n = 5-bromocytosine

<400> SEQUENCE: 115
tnctncaacg ttcg                                                         14

<210> SEQ ID NO 116
<211> LENGTH: 11
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 2
<223> OTHER INFORMATION: n = 5-bromocytosine

```
<400> SEQUENCE: 116
tngaccgttc g                                                        11

<210> SEQ ID NO 117
<211> LENGTH: 16
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 5
<223> OTHER INFORMATION: n = 5-bromocytosine

<400> SEQUENCE: 117
tcgtngtgaa cgttcg                                                   16

<210> SEQ ID NO 118
<211> LENGTH: 14
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 5
<223> OTHER INFORMATION: n = 5-bromocytosine

<400> SEQUENCE: 118
tcgtngaacg ttcg                                                     14

<210> SEQ ID NO 119
<211> LENGTH: 14
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 5
<223> OTHER INFORMATION: n = 5-bromocytosine

<400> SEQUENCE: 119
tcgtngaccg ttcg                                                     14

<210> SEQ ID NO 120
<211> LENGTH: 13
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 8
<223> OTHER INFORMATION: n = 5-bromocytosine

<400> SEQUENCE: 120
tcggaaangt tcg                                                      13

<210> SEQ ID NO 121
<211> LENGTH: 11
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 6
<223> OTHER INFORMATION: n = 5-bromocytosine
```

```
<400> SEQUENCE: 121
tcgaangttc g                                                              11

<210> SEQ ID NO 122
<211> LENGTH: 11
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 2, 6
<223> OTHER INFORMATION: n = 5-bromocytosine

<400> SEQUENCE: 122
tngaangutc g                                                              11

<210> SEQ ID NO 123
<211> LENGTH: 11
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 2, 6
<223> OTHER INFORMATION: n = 5-bromocytosine

<400> SEQUENCE: 123
tngaangttc g                                                              11

<210> SEQ ID NO 124
<211> LENGTH: 14
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 5, 9
<223> OTHER INFORMATION: n = 5-bromocytosine

<400> SEQUENCE: 124
tcgtngaang utcg                                                           14

<210> SEQ ID NO 125
<211> LENGTH: 14
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 5, 9
<223> OTHER INFORMATION: n = 5-bromocytosine

<400> SEQUENCE: 125
tcgtngaang ttcg                                                           14

<210> SEQ ID NO 126
<211> LENGTH: 16
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: (4)...(6)
<223> OTHER INFORMATION: tcg may or may not be present
<220> FEATURE:
```

```
<221> NAME/KEY: misc_feature
<222> LOCATION: (7)...(8)
<223> OTHER INFORMATION: n= any base
<220> FEATURE:
<221> NAME/KEY: misc_feature
<222> LOCATION: 7
<223> OTHER INFORMATION: n may or may not be present
<220> FEATURE:
<221> NAME/KEY: misc_feature
<222> LOCATION: 8
<223> OTHER INFORMATION: n may or may not be present
<220> FEATURE:
<221> NAME/KEY: misc_feature
<222> LOCATION: 10
<223> OTHER INFORMATION: n = t or m

<400> SEQUENCE: 126
tcgtcgnnan cgktcg                                                   16

<210> SEQ ID NO 127
<211> LENGTH: 16
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 2, 5
<223> OTHER INFORMATION: n = 5-bromocytosine
<220> FEATURE:
<221> NAME/KEY: misc_feature
<222> LOCATION: (7)...(8)
<223> OTHER INFORMATION: n = any base
<220> FEATURE:
<221> NAME/KEY: misc_feature
<222> LOCATION: 7
<223> OTHER INFORMATION: n may or may not be present
<220> FEATURE:
<221> NAME/KEY: misc_feature
<222> LOCATION: 8
<223> OTHER INFORMATION: n may or may not be present
<220> FEATURE:
<221> NAME/KEY: misc_feature
<222> LOCATION: 10
<223> OTHER INFORMATION: n = t or m
<220> FEATURE:
<221> NAME/KEY: misc_feature
<222> LOCATION: (4)...(6)
<223> OTHER INFORMATION: tng may or may not be present

<400> SEQUENCE: 127
tngtngnnan cgktcg                                                   16

<210> SEQ ID NO 128
<211> LENGTH: 16
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 5
<223> OTHER INFORMATION: n = 5-bromocytosine
<220> FEATURE:
<221> NAME/KEY: misc_feature
<222> LOCATION: (7)...(8)
<223> OTHER INFORMATION: n = any base
<220> FEATURE:
<221> NAME/KEY: misc_feature
<222> LOCATION: 7
<223> OTHER INFORMATION: n may or may not be present
<220> FEATURE:
<221> NAME/KEY: misc_feature
<222> LOCATION: 8
<223> OTHER INFORMATION: n may or may not be present
<220> FEATURE:
```

```
<221> NAME/KEY: misc_feature
<222> LOCATION: 10
<223> OTHER INFORMATION: n = t or m

<400> SEQUENCE: 128
tcgtngnnan cgktcg                                                              16

<210> SEQ ID NO 129
<211> LENGTH: 16
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: (7)...(8)
<223> OTHER INFORMATION: n = any base
<220> FEATURE:
<221> NAME/KEY: misc_feature
<222> LOCATION: 7
<223> OTHER INFORMATION: n may or may not be present
<220> FEATURE:
<221> NAME/KEY: misc_feature
<222> LOCATION: 8
<223> OTHER INFORMATION: n may or may not be present
<220> FEATURE:
<221> NAME/KEY: misc_feature
<222> LOCATION: 10
<223> OTHER INFORMATION: n = t or m
<220> FEATURE:
<221> NAME/KEY: misc_feature
<222> LOCATION: 11
<223> OTHER INFORMATION: n = 5-bromocytosine
<220> FEATURE:
<221> NAME/KEY: misc_feature
<222> LOCATION: (4)...(6)
<223> OTHER INFORMATION: tcg may or may not be present

<400> SEQUENCE: 129
tcgtcgnnan ngktcg                                                              16

<210> SEQ ID NO 130
<211> LENGTH: 16
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: (4)...(6)
<223> OTHER INFORMATION: tng may or may not be present
<220> FEATURE:
<221> NAME/KEY: misc_feature
<222> LOCATION: 2, 5, 11
<223> OTHER INFORMATION: n = 5-bromocytosine
<220> FEATURE:
<221> NAME/KEY: misc_feature
<222> LOCATION: 10
<223> OTHER INFORMATION: n = t or m
<220> FEATURE:
<221> NAME/KEY: misc_feature
<222> LOCATION: 7
<223> OTHER INFORMATION: n may or may not be present
<220> FEATURE:
<221> NAME/KEY: misc_feature
<222> LOCATION: 8
<223> OTHER INFORMATION: n may or may not be present
<220> FEATURE:
<221> NAME/KEY: misc_feature
<222> LOCATION: (7)...(8)
<223> OTHER INFORMATION: n = any base

<400> SEQUENCE: 130
tngtngnnan ngktcg                                                              16
```

```
<210> SEQ ID NO 131
<211> LENGTH: 16
<212> TYPE: DNA
<213> ORGANISM: Artificial Sequence
<220> FEATURE:
<223> OTHER INFORMATION: Polynucleotide containing (5-bromocytosine)G
<220> FEATURE:
<221> NAME/KEY: misc_feature
<222> LOCATION: 5, 11
<223> OTHER INFORMATION: n = 5-bromocytosine
<220> FEATURE:
<221> NAME/KEY: misc_feature
<222> LOCATION: (7)...(8)
<223> OTHER INFORMATION: n = any base
<220> FEATURE:
<221> NAME/KEY: misc_feature
<222> LOCATION: 7
<223> OTHER INFORMATION: n may or may not be present
<220> FEATURE:
<221> NAME/KEY: misc_feature
<222> LOCATION: 8
<223> OTHER INFORMATION: n may or may not be present
<220> FEATURE:
<221> NAME/KEY: misc_feature
<222> LOCATION: 10
<223> OTHER INFORMATION: n = t or m

<400> SEQUENCE: 131
tcgtngnnan ngktcg                                                    16

<210> SEQ ID NO 132
<211> LENGTH: 21
<212> TYPE: DNA
<213> ORGANISM: Artificial Sequence
<220> FEATURE:
<223> OTHER INFORMATION: Polynucleotide containing CG

<400> SEQUENCE: 132
tcgtcgaacg ttcgagatga t                                              21

<210> SEQ ID NO 133
<211> LENGTH: 10
<212> TYPE: DNA
<213> ORGANISM: Artificial Sequence
<220> FEATURE:
<223> OTHER INFORMATION: Polynucleotide containing CG
<220> FEATURE:
<221> NAME/KEY: misc_feature
<222> LOCATION: 1
<223> OTHER INFORMATION: n= t, c, or 5-bromocytosine
<220> FEATURE:
<221> NAME/KEY: misc_feature
<222> LOCATION: 4
<223> OTHER INFORMATION: n= t or m

<400> SEQUENCE: 133 ndancgktcg                                                           10
```